(12) United States Patent
Lanzavecchia et al.

(10) Patent No.: US 10,889,632 B2
(45) Date of Patent: *Jan. 12, 2021

(54) HUMAN CYTOMEGALOVIRUS NEUTRALIZING ANTIBODIES AND USE THEREOF

(71) Applicant: Institute for Research in Biomedicine, Bellinzona (CH)

(72) Inventors: Antonio Lanzavecchia, Bellinzona (CH); Annalisa Macagno, Bellinzona (CH)

(73) Assignee: Institute for Research in Biomedicine, Bellinzona (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/527,836

(22) Filed: Jul. 31, 2019

(65) Prior Publication Data

US 2020/0017575 A1  Jan. 16, 2020

Related U.S. Application Data

(60) Continuation of application No. 16/025,296, filed on Jul. 2, 2018, now Pat. No. 10,414,817, which is a division of application No. 15/716,818, filed on Sep. 27, 2017, now Pat. No. 10,040,845, which is a division of application No. 15/637,513, filed on Jun. 29, 2017, now Pat. No. 9,803,000, which is a division of application No. 15/284,799, filed on Oct. 4, 2016, now Pat. No. 9,725,502, which is a division of application No. 15/156,786, filed on May 17, 2016, now Pat. No. 9,491,906, which is a division of application No. 14/973,409, filed on Dec. 17, 2015, now Pat. No. 9,371,372, which is a division of application No. 14/815,162, filed on Jul. 31, 2015, now Pat. No. 9,249,213, which is a division of application No. 14/138,531, filed on Dec. 23, 2013, now Pat. No. 9,127,049, which is a division of application No. 13/863,782, filed on Apr. 16, 2013, now Pat. No. 8,765,132, which is a division of application No. 13/608,726, filed on Sep. 10, 2012, now Pat. No. 8,435,524, which is a division of application No. 13/338,934, filed on Dec. 28, 2011, now Pat. No. 8,287,870, which is a division of application No. 12/503,822, filed on Jul. 15, 2009, now Pat. No. 8,124,093.

(60) Provisional application No. 61/081,334, filed on Jul. 16, 2008.

(51) Int. Cl.
| A61K 38/00 | (2006.01) |
| C07K 14/005 | (2006.01) |
| A61K 39/42 | (2006.01) |
| A01D 34/71 | (2006.01) |
| C07K 16/08 | (2006.01) |
| A61K 39/00 | (2006.01) |
| A01D 34/63 | (2006.01) |
| A01D 101/00 | (2006.01) |

(52) U.S. Cl.
CPC ............ *C07K 16/088* (2013.01); *A01D 34/71* (2013.01); *A61K 38/00* (2013.01); *A61K 39/00* (2013.01); *A61K 39/42* (2013.01); *C07K 14/005* (2013.01); *A01D 34/63* (2013.01); *A01D 2101/00* (2013.01); *A61K 2039/505* (2013.01); *A61K 2039/507* (2013.01); *C07K 2317/21* (2013.01); *C07K 2317/34* (2013.01); *C07K 2317/41* (2013.01); *C07K 2317/54* (2013.01); *C07K 2317/55* (2013.01); *C07K 2317/56* (2013.01); *C07K 2317/565* (2013.01); *C07K 2317/622* (2013.01); *C07K 2317/76* (2013.01); *C07K 2317/92* (2013.01); *C12N 2710/16122* (2013.01)

(58) Field of Classification Search
None
See application file for complete search history.

(56) References Cited

U.S. PATENT DOCUMENTS

| 4,294,817 A | 10/1981 | Burgett et al. |
| 4,313,927 A | 2/1982 | Fridlender |
| 4,334,016 A | 6/1982 | Furukawa |
| 4,743,562 A | 5/1988 | Rasmussen et al. |
| 4,783,399 A | 11/1988 | Oldstone et al. |
| 4,804,627 A | 2/1989 | Hammerling et al. |

(Continued)

FOREIGN PATENT DOCUMENTS

| EP | 122841 A1 | 10/1984 |
| EP | 128522 B1 | 12/1984 |

(Continued)

OTHER PUBLICATIONS

Adler, Barbara et al., "Role of human cytomegalovirus UL131A in cell type-specific virus entry and release," Journal of General Virology, vol. 87:2451-2460 (2006).

(Continued)

*Primary Examiner* — Benjamin P Blumel
(74) *Attorney, Agent, or Firm* — Nelson Mullins Riley & Scarborough LLP; Jane E. Remillard, Esq.; Jeanne M. DiGiorgio, Esq.

(57) ABSTRACT

The invention relates to neutralizing antibodies, and antibody fragments thereof, having high potency in neutralizing hCMV, wherein said antibodies and antibody fragments are specific for one, or a combination of two or more, hCMV gene UL products. The invention also relates to immortalized B cells that produce, and to epitopes that bind to, such antibodies and antibody fragments. In addition, the invention relates to the use of the antibodies, antibody fragments, and epitopes in screening methods as well as in the diagnosis, prevention, and therapy of disease.

6 Claims, 3 Drawing Sheets

Specification includes a Sequence Listing.

(56) References Cited

U.S. PATENT DOCUMENTS

| | | |
|---|---|---|
| 4,808,518 A | 2/1989 | Dorsett et al. |
| 5,043,281 A | 8/1991 | Masuho et al. |
| 5,126,130 A | 6/1992 | Lussenhop et al. |
| 5,180,813 A | 1/1993 | Stinski |
| 5,194,654 A | 3/1993 | Hostetler et al. |
| 5,750,106 A | 5/1998 | Dstberg |
| 6,120,989 A | 9/2000 | Vomhagen et al. |
| 6,828,113 B2 | 12/2004 | Initkin |
| 7,947,274 B2 | 5/2011 | Lanzavecchia et al. |
| 7,955,599 B2 | 6/2011 | Lanzavecchia et al. |
| 7,976,845 B2 | 7/2011 | Khanna |
| 8,124,093 B2 | 2/2012 | Lanzavecchia et al. |
| 8,287,870 B2 | 10/2012 | Lanzavecchia et al. |
| 8,298,538 B2 | 10/2012 | Lanzavecchia et al. |
| 8,298,539 B2 | 10/2012 | Lanzavecchia et al. |
| 8,309,089 B2 | 11/2012 | Lanzavecchia et al. |
| 8,435,524 B2 | 5/2013 | Lanzavecchia et al. |
| 8,545,848 B2 | 10/2013 | Lanzavecchia et al. |
| 8,603,480 B2 | 12/2013 | Lanzavecchia et al. |
| 8,765,132 B2 | 7/2014 | Lanzavecchia et al. |
| 9,127,049 B2 | 9/2015 | Lanzavecchia et al. |
| 9,149,524 B2 | 10/2015 | Lanzavecchia et al. |
| 9,217,028 B2 | 12/2015 | Lanzavecchia et al. |
| 9,221,897 B2 | 12/2015 | Lanzavecchia et al. |
| 9,249,213 B2 | 2/2016 | Lanzavecchia et al. |
| 9,365,636 B1 | 6/2016 | Lanzavecchia et al. |
| 9,371,372 B2 | 6/2016 | Lanzavecchia |
| 9,491,906 B2 | 11/2016 | Lanzavecchia et al. |
| 9,527,902 B2 | 12/2016 | Lanzavecchia et al. |
| 9,611,316 B2 | 4/2017 | Lanzavecchia et al. |
| 9,725,502 B2 | 8/2017 | Lanzavecchia et al. |
| 9,796,771 B2 | 10/2017 | Lanzavecchia et al. |
| 9,796,772 B2 | 10/2017 | Lanzavecchia et al. |
| 9,803,000 B1 | 10/2017 | Lanzavecchia et al. |
| 10,040,845 B2 | 8/2018 | Lanzavecchia et al. |
| 10,414,817 B2 | 9/2019 | Lanzavecchia et al. |
| 2003/0223996 A1 | 12/2003 | Ruben et al. |
| 2004/0082033 A1 | 4/2004 | Smith et al. |
| 2004/0110188 A1 | 6/2004 | Hahn |
| 2005/0266243 A1 | 12/2005 | Fukuda et al. |
| 2006/0216302 A1 | 9/2006 | Root-Bernstein |
| 2007/0031851 A1 | 2/2007 | Velculescu et al. |
| 2008/0014208 A1 | 1/2008 | Reiter et al. |
| 2008/0107620 A1 | 5/2008 | Khanna |
| 2008/0187545 A1 | 8/2008 | Shenk et al. |
| 2008/0206784 A1 | 8/2008 | Shiotsuka et al. |
| 2008/0213265 A1 | 9/2008 | Lanzavecchia et al. |
| 2008/0248042 A1 | 10/2008 | De Re et al. |
| 2009/0004198 A1 | 1/2009 | Nakajima et al. |
| 2009/0081230 A1 | 3/2009 | Lanzavecchia et al. |
| 2009/0162378 A1 | 6/2009 | Lai et al. |
| 2010/0092481 A1 | 4/2010 | Lanzavecchia et al. |
| 2011/0150905 A1 | 6/2011 | Papadopoulos et al. |
| 2011/0268746 A1 | 11/2011 | Lanzavecchia et al. |
| 2012/0076801 A1 | 3/2012 | Lanzavecchia et al. |
| 2012/0076802 A1 | 3/2012 | Lanzavecchia et al. |
| 2013/0022618 A1 | 1/2013 | Lanzavecchia et al. |
| 2013/0101604 A1 | 4/2013 | Lanzavecchia et al. |
| 2013/0171169 A1 | 7/2013 | Lanzavecchia et al. |
| 2014/0205615 A1 | 7/2014 | Lanzavecchia et al. |
| 2016/0096880 A1 | 4/2016 | Lanzavecchia et al. |
| 2016/0280769 A1 | 9/2016 | Lanzavecchia et al. |
| 2016/0289302 A1 | 10/2016 | Lanzavecchia et al. |
| 2017/0081391 A1 | 3/2017 | Lanzavecchia et al. |
| 2017/0129939 A1 | 5/2017 | Lanzavecchia et al. |
| 2017/0129940 A1 | 5/2017 | Lanzavecchia et al. |
| 2018/0086819 A1 | 3/2018 | Lanzavecchia et al. |
| 2018/0371062 A1 | 12/2018 | Lanzavecchia et al. |

FOREIGN PATENT DOCUMENTS

| | | |
|---|---|---|
| EP | 162533 A2 | 11/1985 |
| EP | 165830 A1 | 12/1985 |
| EP | 198086 B1 | 10/1986 |
| EP | 248909 B1 | 12/1987 |
| EP | 277071 A2 | 8/1988 |
| EP | 0314161 A1 | 5/1989 |
| EP | 484765 A2 | 5/1992 |
| EP | 527785 B1 | 2/1993 |
| EP | 534102 B1 | 3/1993 |
| EP | 564735 B1 | 10/1993 |
| EP | 680333 B1 | 11/1995 |
| EP | 683675 A1 | 11/1995 |
| EP | 802979 B1 | 10/1997 |
| EP | 832253 B1 | 4/1998 |
| EP | 835122 A1 | 4/1998 |
| EP | 837928 B1 | 4/1998 |
| EP | 882132 B1 | 12/1998 |
| EP | 926155 A2 | 6/1999 |
| EP | 960336 B1 | 12/1999 |
| EP | 964686 A1 | 12/1999 |
| EP | 973536 A1 | 1/2000 |
| EP | 996730 A1 | 5/2000 |
| EP | 1003841 A1 | 5/2000 |
| EP | 1034289 A1 | 9/2000 |
| EP | 1061943 B1 | 12/2000 |
| EP | 1304574 B1 | 4/2003 |
| JP | 5-3794 | 1/1993 |
| JP | 5-260961 B2 | 8/2013 |
| JP | 5807050 B2 | 11/2015 |
| RU | 2239453 C2 | 11/2004 |
| WO | 88/03952 A2 | 6/1988 |
| WO | 90/01497 A1 | 2/1990 |
| WO | 91/04277 A1 | 4/1991 |
| WO | 91/05876 A1 | 5/1991 |
| WO | 93/21952 A1 | 11/1993 |
| WO | 94/09136 A1 | 4/1994 |
| WO | 94/16730 A1 | 8/1994 |
| WO | 94/25490 A1 | 11/1994 |
| WO | 96/37211 A1 | 11/1996 |
| WO | 98/06408 A1 | 2/1998 |
| WO | 98/33510 A1 | 8/1998 |
| WO | 98/33892 A1 | 8/1998 |
| WO | 99/04010 A1 | 1/1999 |
| WO | 99/25858 A1 | 5/1999 |
| WO | 99/45952 A2 | 9/1999 |
| WO | 00/00223 A2 | 1/2000 |
| WO | 00/16061 A2 | 3/2000 |
| WO | 2002-066629 A2 | 8/2002 |
| WO | 03/080672 A1 | 10/2003 |
| WO | 03/085121 A2 | 10/2003 |
| WO | 2004/076645 A2 | 9/2004 |
| WO | 2004/076677 A2 | 9/2004 |
| WO | 2006002177 A2 | 1/2006 |
| WO | 2006006853 A2 | 1/2006 |
| WO | 2006/068953 A2 | 6/2006 |
| WO | 2006137931 A2 | 12/2006 |
| WO | 2007068758 A1 | 6/2007 |
| WO | 2007094423 A1 | 8/2007 |
| WO | 07/146024 A2 | 12/2007 |
| WO | 2007146024 A2 | 12/2007 |
| WO | 2008071806 A1 | 6/2008 |
| WO | 2008084410 A2 | 7/2008 |
| WO | 2008120203 A2 | 10/2008 |
| WO | 2009024445 A1 | 2/2009 |
| WO | 2009085383 A1 | 7/2009 |
| WO | 2010/007533 A2 | 1/2010 |
| WO | 2010007463 A1 | 1/2010 |

OTHER PUBLICATIONS

Andreoni, K.A. et al., "Human CMV/IGIV (CytoGam) neutralizes human cytomegalovirus (HCMV) infectivity and prevents intracellular signal transduction after HCMV exposure," Transplant Infectious Disease, vol. 3(52):25-30 (2001).

Arizono et al., Pharmacokinetics of a new human monoclonal antibody against cytomegalovirus. Third communication: correspondence of the idiotype activityand virus neutralization activity of the new monoclonal antibody, regavirumab in rat serum andits pharmacokinetics in rats and monkeys, 1994, Arzneimit-telforschung, vol. 44, No. 7, abstract.

(56) References Cited

OTHER PUBLICATIONS

Baba, Timothy W. et al., "Human neutralizing monoclonal antibodies of the IgG1 subtype protect against mucosal simian-human immunodeficiency virus infection," Nature Medicine, vol. 6(2):200-206 (2000).

Borucki, M. et al., "A phase II, double-masked, randomized, placebo-controlled evaluation of a human monoclonal anti-Cytomegalovirus antibody (MSL-109) in combination with standard therapy versus standard therapy alone in the treatment of AIDS patients with Cytomegalovirus retinitis," Antiviral Research, vol. 64:103-111 (2004).

Britt, W. J., et al., "Cell surface expression of human cytomegalovirus (HCMV) gp55-116 (gB): use of HCMV recombinant vaccinia virus-infected cells in analysis of the human neutralizing antibody response," J. Virol., vol. 64:1079-1085. (1990).

Britt, W. J., et al., "Oligomerization of the human cytomegalovirus major envelope glycoprotein complex gB (gp55-116)," J. Virol., vol. 66: 6747-6754 (1992).

Brown, M et al: "Tolerance of single, but not multiple, amino acid replacements in antibody VH CDR 2: a means of minimizing B cell wastage from somatic hypermutation?" The Journal of Immunology, vol. 156 (9):3285-3291 (1996).

Clackson, Tim et al., "Making antibody fragments using phage display libraries," Nature, vol. 352:624-628 (1991).

Drosten, Christian et al., "Identification of a Novel Coronavirus in Patients with Severe Acute Respiratory Syndrome," The New England Journal of Medicine, vol. 348:1967-1976 (2003).

European Communication for Application No. 08737590.3, 5 pages, dated Aug. 13, 2012.

European Search Report for Application No. 12156048.6, 18 pages, dated Oct. 22, 2012.

Foung, Steven K.H. et al., "Human Monoclonal Antibodies to Human Cytomegalovirus," The Journal of Infectious Diseases, vol. 159 (3):436-443 (1989).

Funaro, Ada et al., "Generation of potent neutralizing human monoclonal antibodies against cytomegalovirus infection from immune B cells," BMC Biotechnologies, vol. 8:85 doi:10.1186/1472-6750-8-85 (2008).

Gerna, G. et al., "Dendritic-cell infection by human cytomegalovirus is restricted to strains carrying functional UL131-128 genes and mediates efficient viral antigen presentation to CD8+ T Cells," J. Gen. Virology, vol. 86:275-284 (2005).

Gerna, G. et al., "Lack of transmission to polymorphonuclear leukocytes and human umbilical vein endothelial cells are as a marker of attenuation of human cytomegalovirus," J. Med. Virology, vol. 66:335-339 (2002).

Gerna, Giuseppe et al., "Human cytomegalovirus serum neutralizing antibodies block virus infection of endothelial/epithelial cells, but not fibroblasts, early during primary infection," Journal of General Virology, vol. 89:853-865 (2008).

Giusti, A.M et al: "Somatic diversification of S107 from an antiphosphocholine to an anti-DNA autoantibody is due to a single base change in its heavy chain variable region", Proc. Nati. Acad. Sci., vol. 84:2926-2930 (1987).

Goldsby, Richard A. et al., Immunology, Fifth Edition, W.H. Freeman and Company, New York, pp. 83-85 (2003).

Hahn, G. et al., "Human cytomegalovirus UL-131-1289, genes are indispensible for virus growth in endothelial cells and virus tansfer to leukocytes," J. Virology, vol. 78(18):10023-10033 (2004).

Hamilton, Anita A. et al., "A Humanized Antibody against Human Cytomegalovirus (CMV) gpUL75 (gH) for Prophylaxis or Treatment of CMV Infections," JID, vol. 176:59-68 (1997).

International Preliminary Report on Patentability for Application No. PCT/IB2008/001111, dated Jul. 7, 2009.

International Preliminary Report on Patentability for Application No. PCT/IB2009/006641, dated Jan. 18, 2011.

International Search Report and Written Opinion for Application No. PCT/IB2008/002683, dated Mar. 30, 2009.

International Search Report for Application No. PCT/IB2008/001111, dated Nov. 3, 2008.

International Search Report for Application No. PCT/IB2009/006641, dated Jun. 24, 2010.

Invitation to Pay Additional Fees with Partial International Search for Application No. PCT/IB2008/006641, dated Mar. 11, 2010.

Invitrogen, "Mammalian Cell Culture," retrieved online at: http://www.invitrogen.com/site/usien/home/Products-and-Services/Applicati- - -ons/Cell-Culture.html (2010).

Jarvis, Michael A. et al., "Human Cytomegalovirus Tropism for Endothelial Cells: Not All Endothelial Cells Are Created Equal," Journal of Virology, vol. 81(5):2095-2101 (2007).

Kinzler and Compton, Characterization of Human Cytomegalovirus Glycoprotein-Induced Cell-Cell Fusion, 2005, Journal of Virology, vol. 79, No. 12, pp. 7827-7837.

Lantto, Johan et al., "A divalent antibody format is required for neutralization of human cytomegalovirus via antigenic domain 2 on glycoprotein B," Journal of General Virology, vol. 83:2001-2005 (2002).

Lantto, Johan et al., "Binding Characteristics Determine the Neutralizing Potential of Antibody Fragments Specific for Antigenic Domain 2 on Glycoprotein B of Human Cytomegalovirus," Virology, vol. 305:201-209 (2003).

Lanzavecchia, Antonio, "Monoclonal antibody production by EBV transformation of B cells," not yet published U.S. Appl. No. 11/719,835, filed Feb. 26, 2004; Institute for Research in Biomedicine.

Macagno, Annalisa et al., "Isolation of Human Monoclonal Antibodies That Potently Neutralize Human cytomegalovirus Infection by Targeting Different Epitopes on the gH/gL/UL128-131A Complex," Journal of Virology, vol. 84(2):1005-1013 (2010).

Mach, M. et al., "Complex Formation by Human Cytomegalovirus Glycoproteins M (gpUL100) and N (glUL73)," Journal of Virology, vol. 74(24):11881-11892 (2000).

Masuho, Y. et al., "Human monclonal antibodies neutralizing human cytomegalovirus," Journal of General Virology, vol. 68:1457-1461 (1987).

Mazeron, M.G. et al., "Monoclonal antibody E-13 (M-810) to human cytomegalovirus recognizes an epitope encoded by exon 2 of the major immediate early gene," Journal of General Virology, vol. 73:2699-2703 (1992).

McLean, G. et al., "Recognition of human cytomegalovirus by human primary immunoglobulins identifies an innate roundation to an adaptive immune response", J. Immunol., vol. 174:4768-4778 (2005).

Mulder, A. et al., "A human monoclonal antibody, produced following in vitro immunization, recognizing an epitope shared by HLA-A2 subtypes and HLA-A28," Tissue Antigens, vol. 42:27-34 (1993).

National BioResource Project (NBRP)::*E. coli* Strain, "About Cloning Vector Collection," retreived online at: http://www.shigen.nig.act/ecoli/strain/cvector/cvectorExplanation.jsp (2009).

Niedbala, Wanda G. et al., "A Comparison of Three Methods for Production of Human Hybridomas Secreting Autoantibodies," Hybridoma, vol. 17(3):299-304 (1998).

Nigro, G. et al., "Passive immunization during pregnancy for congenital cytomegalovirus infection," New England J. Medicine, vol. 353:1350-1362 (2005).

Ohlin, Mats et al., "Cytomegalovirus Glycoprotein B-Specific Antibody Analysis Using Electrochemiluminescence Detection-Based Techniques," Clinical and Diagnostic Laboratory Immunology, vol. 4(1):107-111 (1997).

Ohlin, Mats et al., "Fine Specificity of the Human Immune Response to the Major Neutralization Epitopes Expressed pn Cytomegalovirus gp58/116 (gB), as Determined with Human Monoclonal Antibodies," Journal of Virology, vol. 67 (2):703-710 (1993).

Park, Jae-Won et al., "Little Role of Anti-gB Antibodies in Neutralizing Activity of Patient's Sera with Human Cytomegalovirus (HCMV) Infection," J. Korean Med. Sci., vol. 15:133-138 (2000).

Patrone, M. et al., "Human cytomegalovirus UL130 protein promotes endothelial cell infection through a producer cell modification of the virion," J. Virology, vol. 79:8361-8373 (2005).

Plachter et al., "Cell types involved in replication and distribution of human cytomegalovirus," Adv Virus Res, vol. 46:195-261 (1996).

(56) References Cited

OTHER PUBLICATIONS

Portolano, Stefano et al., "Lack of Promiscuity in Autoantigen-Specific H and L Chain Combinations as Revealed by Human H and L Chain 'Roulette'," The Journal of Immunology, vol. 150(3):880-887 (1993).
Rudikoff, Stuart et al., "Single amino acid substitution altering nitrogen-binding specificity," Proc. Natl. Acad. Sci. USA, vol. 79:1979-1983 (1982).
Ryckman, Brent J. et al., "Characterization of the Human Cytomegalovirus gH/gL/UL128-131 Complex That Mediates Entry into Epithelial and Endothelial Cells," Journal of Virology, vol. 82(1):60-70 (2008).
Schildbach, J. et al., "Contribution of a single heavy chain residue to specificity of an anti-digoxin monoclonal antibody," Protein Science, vol. 3:737-749 (1994).
Schildbach, J. et al: "Heavy Chain Position 50 Is a Determinant of Affinity and Specificity for the Anti-digoxin Antibody2 6-10". The Journal of Biological Chemistry, vol. 268(29): Issue of Oct. 15: 21739-21747 (1993).
Schoppel, K. et al., "Antibodies Specific for the Antigenic Domain 1 of Glycoprotein B (gpUL55) of Human Cytomegalovirus Bind to Different Substructures," Virology, vol. 216:133-146 (1996).
Schoppel, K., et al., "Antibodies specific for the antigenic domain 1 (AD-1) ofglycoprotein B (gpUL55) of human cytomegalovirus bind to different substructures," Virology, vol. 216:133-145 (1996).
Shimamura, Masako et al., "Human Cytomegalovirus Infection Elicits a Glycoprotein M (gM)/gN-Specific Virus-Neutralizing Antibody Response," Journal of Virology, vol. 80(9):4591-4600 (2006).
Summons to Attend Oral Proceedings, European Application No. 09745098.5, dated Sep. 27, 2016, 5 pages.
Takekoshi, M. et al., "Human monoclonal anti-HCMV neutralizing antibody from phage display libraries," Journal of Virological Methods, vol. 74:89-98 (1998).
Tamura, Midori et al., "Structural Correlates of an Anticarcinoma Antibody: Identification of Specificity-Determining Residues (SDRs) and Devleopment of a Minimally Immunogenic Antibody Variant by Retention of SDRs Only," The Journal of Immunology, vol. 164:1432-1441 (2000).
Vajdos, Felix F. et al., "Comprehensive Functional Maps of the Antigen-binding Site of an Anti-ErbB2 Antibody Obtained with Shotgun Scanning Mutagenesis," J. Mol. Biol., vol. 320:415-428 (2002).
Wang et al., "Fc-Glycosylation of IgG1 is Modulated by B-cell Stimuli," Molecular and Cellular Proteomics, vol. 10, pp. 1-12. (2011).
Wang, Dai et al., "Human Cytomegalovirus UL131 Open Reading Frame Is Required for Epithelial Cell Tropism," Journal of Virology, vol. 79(16):10330-10338 (2005).
Wang, Dai et al., "Human cytomegalovirus virion protein complex required for epithelial and endothelial cell tropism," PNAS, vol. 102(50):18153-18158 (2005).
Wen, Y et al., "Human cytomegalovirus gH/gL/UL128/UL130/UL131A complex elicits potently neutralizing antibodies in mice," Vaccine, vol. 32(30):3796-3804 (2014).
Written Opinion for Application No. PCT/IB2008/002683, dated Jul. 7, 2009.
Xiang J, et al.: "Study of B72.3 combining sites by molecular modeling and site directed mutagenesis,". Protein Eng., vol. 13(5):339-44 (2000).
U.S. Appl. No. 13/618,264, filed Sep. 14, 2012, Antonio Lanzavecchia.
U.S. Appl. No. 13/087,814, filed Apr. 15, 2011, Antonio Lanzavecchia.
U.S. Appl. No. 12/174,568, filed Jul. 16, 2008, Antonio Lanzavecchia.
U.S. Appl. No. 14/938,438, filed Nov. 11, 2015, Antonio Lanzavecchia.
U.S. Appl. No. 11/969,104, filed Jan. 3, 2008, Antonio Lanzavecchia.
U.S. Appl. No. 13/092,364, filed Apr. 22, 2011, Antonio Lanzavecchia.
U.S. Appl. No. 13/619,305, filed Sep. 14, 2012, Antonio Lanzavecchia.
U.S. Appl. No. 14/041,799, filed Sep. 30, 2013, Antonio Lanzavecchia.
U.S. Appl. No. 13/863,782, filed Apr. 16, 2013, Antonio Lanzavecchia.
U.S. Appl. No. 13/608,726, filed Sep. 10, 2012, Antonio Lanzavecchia.
U.S. Appl. No. 13/338,905, filed Dec. 28, 2011, Antonio Lanzavecchia.
U.S. Appl. No. 13/338,934, filed Dec. 28, 2011, Antonio Lanzavecchia.
U.S. Appl. No. 12/503,822, filed Jul. 15, 2009, Antonio Lanzavecchia.
U.S. Appl. No. 14/138,531, filed Dec. 23, 2013, Antonio Lanzavecchia.
U.S. Appl. No. 14/815,162, filed Jul. 31, 2015, Antonio Lanzavecchia.
U.S. Appl. No. 14/973,409, filed Dec. 17, 2015, Antonio Lanzavecchia.
U.S. Appl. No. 15/156,786, filed May 17, 2016, Antonio Lanzavecchia.
U.S. Appl. No. 15/284,799, filed Oct. 4, 2016, Antonio Lanzavecchia.
U.S. Appl. No. 15/637,513, filed Jun. 29, 2017, Antonio Lanzavecchia.
U.S. Appl. No. 15/716,818, filed Sep. 27, 2017, Antonio Lanzavecchia.
U.S. Appl. No. 16/025,296, filed Jul. 2, 2018, Antonio Lanzavecchia.
U.S. Appl. No. 13/003,603, filed May 27, 2011, Antonio Lanzavecchia.
U.S. Appl. No. 14/096,283, filed Dec. 4, 2013, Antonio Lanzavecchia.
U.S. Appl. No. 14/949,161, filed Nov. 23, 2015, Antonio Lanzavecchia.
U.S. Appl. No. 15/154,178, filed May 13, 2016, Antonio Lanzavecchia.
U.S. Appl. No. 15/154,178, filed Nov. 22, 2016, Antonio Lanzavecchia.
U.S. Appl. No. 15/358,868, filed Nov. 22, 2016, Antonio Lanzavecchia.
U.S. Appl. No. 13/618,264, filed Aug. 13, 2015, B. Blumel.
U.S. Appl. No. 13/618,264, filed Mar. 5, 2015, B. Blumel.
U.S. Appl. No. 13/618,264, filed Aug. 28, 2014, B. Blumel.
U.S. Appl. No. 13/618,264, filed Feb. 25, 2014, B. Blumel.
U.S. Appl. No. 13/618,264, filed Jul. 31, 2013, B. Blumel.
U.S. Appl. No. 13/618,264, filed Apr. 12, 2013, B. Blumel.
U.S. Appl. No. 13/087,814, filed Jun. 29, 2012, B. Blumel.
U.S. Appl. No. 13/087,814, filed Apr. 6, 2012, B. Blumel.
U.S. Appl. No. 13/087,814, filed Mar. 2, 2012, B. Blumel.
U.S. Appl. No. 12/174,568, filed Feb. 28, 2011, B. Blumel.
U.S. Appl. No. 12/174,568, filed Aug. 13, 2010, B. Blumel.
U.S. Appl. No. 12/174,568, filed Sep. 4, 2009, B. Blumel.
U.S. Appl. No. 12/174,568, filed Apr. 28, 2009, B. Blumel.
U.S. Appl. No. 14/938,438, filed Jan. 30, 2017, B. Blumel.
U.S. Appl. No. 14/938,438, filed Oct. 18, 2016, B. Blumel.
U.S. Appl. No. 14/938,438, filed Jul. 15, 2016, B. Blumel.
U.S. Appl. No. 11/969,104, filed Feb. 28, 2011, B. Blumel.
U.S. Appl. No. 11/969,104, filed Aug. 16, 2010, B. Blumel.
U.S. Appl. No. 11/969,104, filed Feb. 5, 2010, B. Blumel.
U.S. Appl. No. 11/969,104, filed Apr. 3, 2009, B. Blumel.
U.S. Appl. No. 11/969,104, filed Nov. 17, 2008, B. Blumel.
U.S. Appl. No. 13/092,364, filed Jul. 06, 2012, B. Blumel.
U.S. Appl. No. 13/092,364, filed Apr. 20, 2012, B. Blumel.
U.S. Appl. No. 13/092,364, filed Mar. 15, 2012, B. Blumel.
U.S. Appl. No. 13/619,305, filed Jun. 6, 2013, B. Blumel.
U.S. Appl. No. 13/619,305, filed Mar. 5, 2013, B. Blumel.
U.S. Appl. No. 14/041,799, filed May 27, 2015, B. Blumel.
U.S. Appl. No. 14/041,799, filed Feb. 24, 2015, B. Blumel.
U.S. Appl. No. 14/041,799, filed Aug. 14, 2014, B. Blumel.

(56) References Cited

OTHER PUBLICATIONS

U.S. Appl. No. 13/863,782, filed May 22, 2014, B. Blumel.
U.S. Appl. No. 13/863,782, filed Sep. 18, 2013, B. Blumel.
U.S. Appl. No. 13/608,726, filed Jan. 11, 2013, B. Blumel.
U.S. Appl. No. 13/338,934, filed Sep. 20, 2012, B. Blumel.
U.S. Appl. No. 13/338,934, filed Jun. 28, 2012, B. Blumel.
U.S. Appl. No. 13/338,934, filed Jun. 6, 2012, B. Blumel.
U.S. Appl. No. 13/338,934, filed May 2, 2012, B. Blumel.
U.S. Appl. No. 13/338,934, filed Mar. 19, 2012, B. Blumel.
U.S. Appl. No. 12/503,822, filed Sep. 19, 2011, B. Blumel.
U.S. Appl. No. 12/503,822, filed May 13, 2011, B. Blumel.
U.S. Appl. No. 14/138,531, filed May 4, 2015, B. Blumel.
U.S. Appl. No. 14/138,531, filed Feb. 24, 2015, B. Blumel.
U.S. Appl. No. 14/138,531, filed Aug. 14, 2014, B. Blumel.
U.S. Appl. No. 14/815,162, filed Sep. 18, 2015, B. Blumel.
U.S. Appl. No. 13/338,905, filed Jun. 28, 2012, B. Blumel.
U.S. Appl. No. 13/338,905, filed May 2, 2012, B. Blumel.
U.S. Appl. No. 13/003,603, filed Aug. 8, 2013, B. Blumel.
U.S. Appl. No. 13/003,603, filed Apr. 30, 2013, B. Blumel.
U.S. Appl. No. 13/003,603, filed Jan. 18, 2013, B. Blumel.
U.S. Appl. No. 14/096,283, filed Sep. 17, 2015, B. Blumel.
U.S. Appl. No. 14/096,283, filed Jul. 15, 2015, B. Blumel.
U.S. Appl. No. 14/096,283, filed Feb. 26, 2015, B. Blumel.
U.S. Appl. No. 14/096,283, filed Aug. 20, 2014, B. Blumel.
U.S. Appl. No. 14/973,409, filed Feb. 24, 2016, B. Blumel.
U.S. Appl. No. 14/973,409, filed Jan. 13, 2016, B. Blumel.
U.S. Appl. No. 15/156,786, filed Jul. 19, 2016, B. Blumel.
U.S. Appl. No. 14/949,161, filed Apr. 14, 2016, B. Blumel.
U.S. Appl. No. 14/949,161, filed Mar. 1, 2016, B. Blumel.
U.S. Appl. No. 15/154,178, filed Aug. 19, 2016, B. Blumel.
U.S. Appl. No. 15/154,178, filed Jul. 8, 2016, B. Blumel.
U.S. Appl. No. 15/284,799, filed Apr. 3, 2017, B. Blumel.
U.S. Appl. No. 15/284,799, filed Dec. 23, 2016, B. Blumel.
U.S. Appl. No. 15/637,513, filed Sep. 14, 2017, B. Blumel.
U.S. Appl. No. 15/637,513, filed Aug. 23, 2017, B. Blumel.
U.S. Appl. No. 15/716,818, filed Apr. 17, 2018, B. Blumel.
U.S. Appl. No. 15/716,818, filed Dec. 26, 2017, B. Blumel.
U.S. Appl. No. 15/358,845, filed Jul. 11, 2017, B. Blumel.
U.S. Appl. No. 15/358,845, filed May 19, 2017, B. Blumel.
U.S. Appl. No. 15/358,845, filed Feb. 10, 2017, B. Blumel.
U.S. Appl. No. 15/358,868, filed Jul. 11, 2017, B. Blumel.
U.S. Appl. No. 15/358,868, filed May 19, 2017, B. Blumel.
U.S. Appl. No. 15/358,868, filed Feb. 9, 2017, B. Blumel.
U.S. Appl. No. 16/025,296, filed May 8, 2019, B. Blumel.
U.S. Appl. No. 16/025,296, filed Jan. 28, 2019, B. Blumel.
U.S. Appl. No. 16/025,296, filed Sep. 28, 2019, B. Blumel.

A

B

HUMAN CYTOMEGALOVIRUS NEUTRALIZING ANTIBODIES AND USE THEREOF

RELATED APPLICATIONS

This application is a continuation of U.S. Ser. No. 16/025,296 (allowed), filed on Jul. 2, 2018, which is a divisional of U.S. Pat. No. 10,040,845, issued on Aug. 7, 2018, which is a divisional of U.S. Pat. No. 9,803,000, issued on Oct. 31, 2017, which is a divisional of U.S. Pat. No. 9,725,502, issued on Aug. 8, 2017, which is a divisional of U.S. Pat. No. 9,491,906, issued on Nov. 15, 2016, which is a divisional of U.S. Pat. No. 9,371,372, issued on Jun. 21, 2016, which is a divisional of U.S. Pat. No. 9,249,213, issued on Feb. 2, 2016, which is a divisional of U.S. Pat. No. 9,127,049, issued on Sep. 8, 2015, which is a divisional of U.S. Pat. No. 8,765,132, issued on Jul. 1, 2014, which is a divisional of U.S. Pat. No. 8,435,524, issued on May 7, 2013, which is a divisional of U.S. Pat. No. 8,287,870, issued on Oct. 16, 2012, which is a divisional of U.S. Pat. No. 8,124,093, issued on Feb. 28, 2012, which claims priority to U.S. Provisional Application No. 61/081,334, filed on Jul. 16, 2008, the contents of which are hereby incorporated by reference.

SEQUENCE LISTING

The instant application contains a Sequence Listing which has been submitted in ASCII format via EFS-Web, and is hereby incorporated by reference in its entirety. Said ASCII copy, created on Jul. 31, 2019, is named NVJ-003DV11CN_Sequence_Listing.txt and is 124,243 bytes in size.

BACKGROUND

Human cytomegalovirus (hCMV) is a widely distributed pathogen that may cause severe pathology in immunosuppressed adults and upon infection of the fetus and has been implicated in chronic diseases such as atherosclerosis. hCMV infects multiple cell types including fibroblasts, endothelial, epithelial and hematopoietic cells [1]. In vitro propagated attenuated strains of hCMV, which are being developed as candidate vaccines, have lost the tropism for endothelial cells, while retaining the capacity to infect fibroblasts [2]. Two viral glycoprotein complexes are believed to control the cellular tropism of hCMV. A complex of glycoproteins such as gH, gL and gO appears to be required for infection of fibroblasts, while a complex of gH, gL and proteins encoded by the UL131-UL128 genes is implicated in infection of endothelial cells, epithelial cells and dendritic cells [2-8].

Hyperimmune globulins are already commercialized for the prophylaxis of hCMV disease associated with transplantation and recent evidence indicates that they have therapeutic effect in pregnant women [9]. This therapeutic approach is limited by the low amount of neutralizing antibody that can be transferred and for this reason the availability of human antibodies (such as human monoclonal antibodies) with high neutralizing capacity would be highly desirable. Although some antibodies to gH, gB and UL128 and UL130 gene products have demonstrated in vitro neutralizing activities [7, 10, 11] and an antibody to gH was evaluated in clinical trials (that were discontinued due to lack of therapeutic effects), the neutralizing potency of the antibodies isolated so far is modest. Neutralization by these antibodies was observed at antibody concentrations ranging from 0.5 to 20 µg/ml. Further, the current methods typically measure the neutralizing potency of anti-hCMV antibodies using fibroblasts as target cells. However, hCMV is also known to cause pathology by infecting other cell types such as endothelial, epithelial cells and leukocytes. Known antibodies to UL128 and UL130 show very low potency in neutralizing infection of endothelial cells [7] and there do not appear to be any monoclonal antibodies available that would be capable of neutralizing infection of non-fibroblast target cells with high potency.

There is therefore a need for antibodies that neutralize hCMV infection, particularly hCMV infection of non-fibroblast target cells, with high potency, as well as the elucidation of the target(s) to which such antibodies bind.

SUMMARY OF INVENTION

The invention is based, in part, on the discovery of novel antibodies that neutralize hCMV infection with high potency as well as novel epitopes to which the antibodies of the invention bind. Accordingly, in one aspect, the invention comprises an antibody and antigen binding fragments thereof that have high potency in neutralizing hCMV.

In one embodiment of the invention, the invention comprises a monoclonal antibody, or an antigen binding fragment thereof, that binds to an epitope in the hCMV UL128 protein, wherein the antibody neutralizes hCMV infection. In another embodiment of the invention, the invention comprises an antibody, or an antigen binding fragment thereof, that binds to an epitope formed by the hCMV proteins gH, gL, UL128 and UL130, the hCMV proteins UL128, UL130 and UL131A, or the hCMV proteins UL130 and UL131A, wherein the antibody neutralizes hCMV infection.

In yet another embodiment of the invention, the invention comprises an antibody, or an antigen binding fragment thereof, comprising at least one complementarity determining region ("CDR") sequence having at least 95% sequence identity to any one of SEQ ID NOs: 188-193, 204, 205, 210, 174-177, 149, 178, 65-70, 81-86, 97-102, 129-134, 145-150, 113, 161-164, 1-6, 17-22, 33-38, 49-54, or 114-118, wherein the antibody neutralizes hCMV infection.

In yet another embodiment of the invention, the invention comprises a heavy chain CDR1 selected from the group consisting of SEQ ID NOs: 188, 174, 65, 81, 97, 129, 145, 113, 1, 17, 33, and 49; a heavy chain CDR2 selected from the group consisting of SEQ ID NOs: 189, 204, 175, 66, 82, 98, 130, 146, 161, 2, 2, 18, 34, 50, and 114; and a heavy chain CDR3 selected from the group consisting of SEQ ID NOs: 190, 205, 210, 176, 67, 83, 99, 131, 147, 162, 3, 19, 35, 51, and 115, wherein the antibody neutralizes hCMV infection. In yet another embodiment of the invention, the invention comprises an antibody, or an antigen binding fragment thereof, comprising a light chain CDR1 selected from the group consisting of SEQ ID NOs: 191, 177, 68, 84, 100, 132, 148, 163, 4, 20, 36, 52, and 116; a light chain CDR2 selected from the group consisting of SEQ ID NOs: 192, 149, 69, 85, 101, 133, 5, 21, 37, 53, and 117; and a light chain CDR3 selected from the group consisting of SEQ ID NOs: 193, 178, 70, 86, 102, 134, 150, 164, 6, 22, 38, 54, and 118, wherein the antibody neutralizes hCMV infection.

In still another embodiment of the invention, the invention comprises an antibody, or an antigen binding fragment thereof, wherein the antibody comprises a heavy chain variable region comprising the amino acid sequence of SEQ ID NO: 200 and a light chain variable region comprising the amino acid sequence of SEQ ID NO: 201; or a heavy chain variable region comprising the amino acid sequence of SEQ ID NO: 200 and a light chain variable region comprising the amino acid sequence of SEQ ID NO: 213; or a heavy chain variable region comprising the amino acid sequence of SEQ ID NO: 208 and a light chain variable region comprising the amino acid sequence of SEQ ID NO: 201; or a heavy chain variable region comprising the amino acid sequence of SEQ ID NO: 208 and a light chain variable region comprising the amino acid sequence of SEQ ID NO: 213; or a heavy chain variable region comprising the amino acid sequence of SEQ ID NO: 212 and a light chain variable region comprising the amino acid sequence of SEQ ID NO: 201; or a heavy chain variable region comprising the amino acid sequence of SEQ ID NO: 212 and a light chain variable region comprising the amino acid sequence of SEQ ID NO: 213; or a heavy chain variable region comprising the amino acid sequence of SEQ ID NO: 184 and a light chain variable region comprising the amino acid sequence of SEQ ID NO: 185; or a heavy chain variable region comprising the amino acid sequence of SEQ ID NO: 77 and a light chain variable region comprising the amino acid sequence of SEQ ID NO: 78; or a heavy chain variable region comprising the amino acid sequence of SEQ ID NO: 93 and a light chain variable region comprising the amino acid sequence of SEQ ID NO: 94; or a heavy chain variable region comprising the amino acid sequence of SEQ ID NO: 109 and a light chain variable region comprising the amino acid sequence of SEQ ID NO: 110; or a heavy chain variable region comprising the amino acid sequence of SEQ ID NO: 141 and a light chain variable region comprising the amino acid sequence of SEQ ID NO: 142; or a heavy chain variable region comprising the amino acid sequence of SEQ ID NO: 157 and a light chain variable region comprising the amino acid sequence of SEQ ID NO: 158; or a heavy chain variable region comprising the amino acid sequence of SEQ ID NO: 170 and a light chain variable region comprising the amino acid sequence of SEQ ID NO: 171; or a heavy chain variable region comprising the amino acid sequence of SEQ ID NO: 13 and a light chain variable region comprising the amino acid sequence of SEQ ID NO: 14; or a heavy chain variable region comprising the amino acid sequence of SEQ ID NO: 29 and a light chain variable region comprising the amino acid sequence of SEQ ID NO: 30; or a heavy chain variable region comprising the amino acid sequence of SEQ ID NO: 45 and a light chain variable region comprising the amino acid sequence of SEQ ID NO: 46; or a heavy chain variable region comprising the amino acid sequence of SEQ ID NO: 61 and a light chain variable region comprising the amino acid sequence of SEQ ID NO: 62; or a heavy chain variable region comprising the amino acid sequence of SEQ ID NO: 125 and a light chain variable region comprising the amino acid sequence of SEQ ID NO: 126, and wherein the antibody neutralizes hCMV infection.

In a further embodiment of the invention, the invention comprises an antibody, or an antigen binding fragment thereof, that neutralizes infection of endothelial cells, epithelial cells, retinal cells, myeloid cells, dendritic cells, fibroblasts, or mesenchymal stromal cells by a clinical isolate of hCMV, wherein the concentration of antibody required for 90% neutralisation of hCMV is 1.2 µg/ml or less. In another embodiment of the invention, the invention comprises an antibody, or an antigen binding fragment thereof, that neutralizes infection of endothelial cells, epithelial cells, retinal cells, myeloid cells, dendritic cells, fibroblasts, or mesenchymal stromal cells by a clinical isolate of hCMV, wherein the concentration of antibody required for 90% neutralisation of hCMV is 10 µg/ml or less, and wherein the antibody is not MSL-109 or 8F9.

In yet another embodiment of the invention, the invention comprises an antibody, or an antigen binding fragment thereof, comprising at least one CDR sequence having at least 95% sequence identity to any one of SEQ ID NOs: 216-221, 232-235, 149, 236, 246-251, 278-283, 296-301, 312, 316-321, 332, 336-341, 352, 360, 361 or 262-267, wherein the antibody neutralizes hCMV infection.

In yet another embodiment of the invention, the invention comprises an antibody, or an antigen binding fragment thereof, comprising a heavy chain CDR1 selected from the group consisting of SEQ ID NOs: 216, 232, 246, 278, 296, 316, 336, 352, 360 and 262; a heavy chain CDR2 selected from the group consisting of SEQ ID NOs: 217, 233, 247, 279, 297, 312, 317, 337 and 263; and a heavy chain CDR3 selected from the group consisting of SEQ ID NOs: 218, 234, 248, 280, 298, 318, 332, 338, and 264, wherein the antibody neutralizes hCMV infection.

In yet another embodiment of the invention, the invention comprises an antibody, or an antigen binding fragment thereof, comprising a light chain CDR1 selected from the group consisting of SEQ ID NOs: 219, 235, 249, 281, 299, 319, 339 and 265; a light chain CDR2 selected from the group consisting of SEQ ID NOs: 220, 149, 250, 282, 300, 320, 340 and 266; and a light chain CDR3 selected from the group consisting of SEQ ID NOs: 221, 236, 251, 283, 301, 321, 341, 361 and 267, wherein the antibody neutralizes hCMV infection.

In still another embodiment of the invention, the invention comprises an antibody, or an antigen binding fragment thereof, wherein the antibody comprises a heavy chain variable region comprising the amino acid sequence of SEQ ID NO: 228 and a light chain variable region comprising the amino acid sequence of SEQ ID NO: 229; or a heavy chain variable region comprising the amino acid sequence of SEQ ID NO: 242 and a light chain variable region comprising the amino acid sequence of SEQ ID NO: 243; or a heavy chain variable region comprising the amino acid sequence of SEQ ID NO: 258 and a light chain variable region comprising the amino acid sequence of SEQ ID NO: 259; or a heavy chain variable region comprising the amino acid sequence of SEQ ID NO: 290, and a light chain variable region comprising the amino acid sequence of SEQ ID NO: 291; or a heavy chain variable region comprising the amino acid sequence of SEQ ID NO: 294, and a light chain variable region comprising the amino acid sequence of SEQ ID NO: 291; or a heavy chain variable region comprising the amino acid sequence of SEQ ID NO: 308, and a light chain variable region comprising the amino acid sequence of SEQ ID NO: 309; or a heavy chain variable region comprising the amino acid sequence of SEQ ID NO: 314, and a light chain variable region comprising the amino acid sequence of SEQ ID NO: 309; or a heavy chain variable region comprising the amino acid sequence of SEQ ID NO: 328, and a light chain variable region comprising the amino acid sequence of SEQ ID NO: 329; or a heavy chain variable region comprising the amino acid sequence of SEQ ID NO: 334, and a light chain variable region comprising the amino acid sequence of SEQ ID NO: 329; or a heavy chain variable region comprising the amino acid sequence of SEQ ID NO: 348 and a light chain variable region comprising the amino acid sequence of SEQ ID NO: 349; or a heavy chain variable region comprising the amino acid sequence of SEQ ID NO: 357 and a light chain variable region comprising the amino acid sequence of SEQ ID NO: 291; or a heavy chain variable region comprising the amino acid sequence of SEQ ID NO: 367 and a light chain variable region comprising the amino acid sequence of SEQ ID NO: 368; or a heavy chain variable region comprising the amino acid sequence of SEQ ID NO: 274 and a light chain variable region comprising the amino acid sequence of SEQ ID NO: 275, and wherein the antibody neutralizes hCMV infection.

The invention further comprises an antibody, or an antigen binding fragment thereof, produced by immortalised B cell clone 8I21, 2C12, 8C15, 4N10, 11B12, 3G16, 4H9, 6B4, 10C6, or 6L3 deposited with the Advanced Biotechnology Center (ABC), Largo Rossana Benzi 10, 16132 Genoa (Italy), under the terms of the Budapest Treaty, on Jul. 9, 2008 (under Accession Numbers PD 08005, PD 08007, PD 08006, PD 08009, PD 08011, PD 08012, PD 08013, PD 08004, PD 08014, and PD 08010, respectively) and by immortalized B cell clone 7H3 deposited on Jul. 16, 2008 under Accession Number PD 08017. Antibodies and antigen binding fragments thereof, with the same amino acid sequence as those expressed from the aforementioned deposited immortalised B cells are also considered to be within the scope of the invention.

In another aspect, the invention comprises a nucleic acid molecule comprising a polynucleotide encoding an antibody or antibody fragment of the invention that neutralizes hCMV infection. In yet another aspect, the invention comprises a cell expressing an antibody of the invention. In still another aspect, the invention comprises an isolated or purified immunogenic polypeptide comprising an epitope that binds to an antibody of the invention.

The invention further comprises a pharmaceutical composition comprising an antibody of the invention or an antigen binding fragment thereof, a nucleic acid molecule of the invention, or an immunogenic polypeptide of the invention, and a pharmaceutically acceptable diluent or carrier. The invention also comprises a pharmaceutical composition comprising a first antibody or an antigen binding fragment thereof, and a second antibody, or an antigen binding fragment thereof, wherein the first antibody is an antibody of the invention, and the second antibody is an antibody that neutralizes hCMV infection.

Use of an antibody of the invention, or an antigen binding fragment thereof, a nucleic acid of the invention, an immunogenic polypeptide of the invention, or a pharmaceutical composition of the invention (i) in the manufacture of a medicament for the treatment of hCMV infection, (ii) in a vaccine, or (iii) in diagnosis of hCMV infection is also contemplated to be within the scope of the invention. Further, use of an antibody of the invention, or an antigen binding fragment thereof, for monitoring the quality of anti-hCMV vaccines by checking that the antigen of said vaccine contains the specific epitope in the correct conformation is also contemplated to be within the scope of the invention.

In a further aspect, the invention comprises an epitope which specifically binds to an antibody of any one of the invention, or an antigen binding fragment thereof, for use (i) in therapy, (ii) in the manufacture of a medicament for treating hCMV infection, (iii) as a vaccine, or (iv) in screening for ligands able to neutralise hCMV infection.

DETAILED DESCRIPTION OF THE INVENTION

Figure 1:
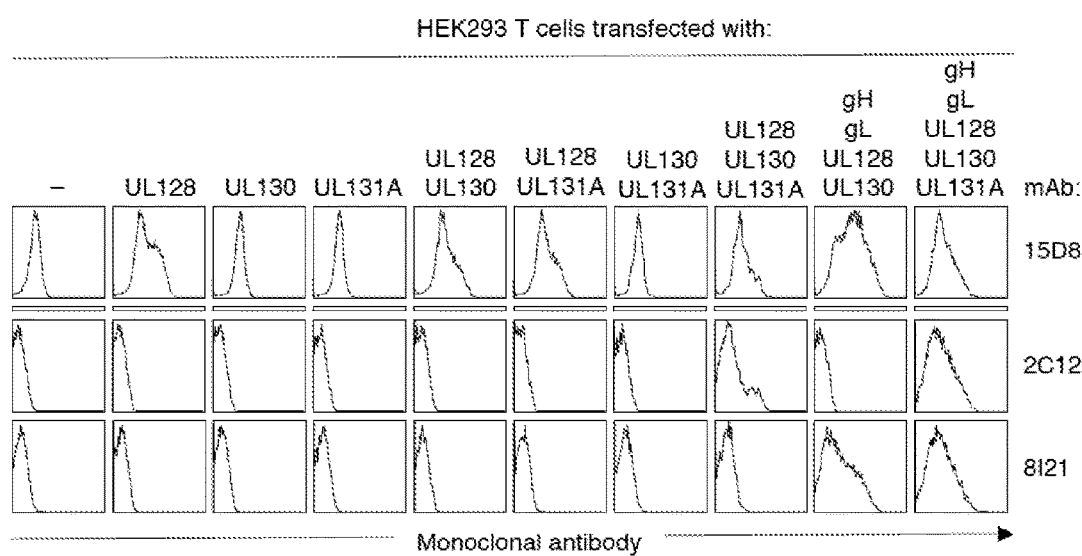
FIG. 1 shows staining of HEK293T cells transfected with hCMV UL128, UL130, UL131A, gH and gL genes, alone or in different combinations, by representative monoclonal antibodies (15D8, 2C12 and 8I21).

The invention is based, in part, on the discovery of novel antibodies that neutralize hCMV infection with high potency as well as novel epitopes to which the antibodies of the invention bind. Such antibodies are desirable, as only low concentrations are required in order to neutralize a given amount of virus. This facilitates higher levels of protection whilst administering lower amounts of antibody. Accordingly, in one aspect, the invention comprises a neutralizing antibody and antigen binding fragments thereof having high potency in neutralizing hCMV infection. Human monoclonal antibodies and the immortalised B cell clones that secrete such antibodies are also included within the scope of the invention.

As used herein, the terms "fragment," "antigen binding fragment" and "antibody fragment" are used interchangeably to refer to any fragment of an antibody of the invention that retains the antigen-binding activity of the antibodies. Exemplary antibody fragments include, but are not limited to, a single chain antibody, Fab, Fab', F(ab')2, Fv or scFv.

As used herein, the term "high potency" is used to refer to an antibody of the invention or an antigen binding fragment thereof that neutralizes hCMV infection with an $IC_{90}$ of less than about 2 µg/ml, (i.e. the concentration of antibody required for 90% neutralisation of a clinical isolate of hCMV is about 2 µg/ml or less, for example 1.9, 1.8, 1.75, 1.7, 1.6, 1.5, 1.4, 1.3, 1.25, 1.2, 1.15, 1.1, or 1.05 µg/ml or less). In one embodiment, the antibody of the present invention, or antigen binding fragment thereof, has an $IC_{90}$ of 1 µg/ml or less (i.e. 0.95, 0.9, 0.85, 0.8, 0.75, 0.7, 0.6, 0.5, 0.4, 0.3, 0.2, 0.1, 0.05, 0.01 µg/ml or less). In another embodiment, the antibody of the present invention, or antigen binding fragment thereof, has an $IC_{90}$ of 0.16 µg/ml or less (i.e. 0.15, 0.125, 0.1, 0.075, 0.05, 0.025, 0.02, 0.015, 0.0125, 0.01, 0.0075, 0.005, 0.004, 0.003, 0.002 µg/ml or less). In another embodiment, the antibody can neutralize hCMV infection at a concentration of 0.016 µg/ml or less (i.e. at 0.015, 0.013, 0.01, 0.008, 0.005, 0.003, 0.002, 0.001, 0.0005 µg/ml or less). This means that only very low concentrations of antibody are required for 90% neutralisation of a clinical isolate of hCMV in vitro compared to the concentration of known antibodies, e.g., MSL-109, 8F9 or 3E3, required for neutralisation of the same titre of hCMV. Potency can be measured using a standard neutralisation assay as known to one of skill in the art.

In one embodiment, the invention provides an antibody, for example, a monoclonal antibody or a human monoclonal antibody, or an antigen binding fragment thereof, that binds to an epitope in the hCMV UL128 protein and neutralizes hCMV infection with an $IC_{90}$ of less than about 2 µg/ml, for example 1.9, 1.8, 1.75, 1.7, 1.6, 1.5, 1.4, 1.3, 1.25, 1.2, 1.15, 1.1, 1.05, 1, 0.95, 0.9, 0.85, 0.8, 0.75, 0.7, 0.6, 0.5, 0.4, 0.3, 0.2, 0.15, 0.125, 0.1, 0.075, 0.05, 0.025, 0.02, 0.015, 0.0125, 0.01, 0.0075, 0.005, 0.004, 0.003, 0.002 0.001, 0.0005 µg/ml or less.

In another embodiment, the invention provides an antibody, or an antigen binding fragment thereof, that binds to an epitope formed by the hCMV proteins gH, gL, UL128 and UL130, and neutralizes hCMV infection with an $IC_{90}$ of less than about 2 µg/ml, for example 1.9, 1.8, 1.75, 1.7, 1.6, 1.5, 1.4, 1.3, 1.25, 1.2, 1.15, 1.1, 1.05, 1, 0.95, 0.9, 0.85, 0.8, 0.75, 0.7, 0.6, 0.5, 0.4, 0.3, 0.2, 0.15, 0.125, 0.1, 0.075, 0.05, 0.025, 0.02, 0.015, 0.0125, 0.01, 0.0075, 0.005, 0.004, 0.003, 0.002 0.001, 0.0005 µg/ml or less.

In another embodiment, the invention provides an antibody, or an antigen binding fragment thereof, that binds to an epitope formed by the hCMV proteins UL128, UL130, and UL131A, and neutralizes hCMV infection with an $IC_{90}$ of less than about 2 µg/ml, for example 1.9, 1.8, 1.75, 1.7, 1.6, 1.5, 1.4, 1.3, 1.25, 1.2, 1.15, 1.1, 1.05, 1, 0.95, 0.9, 0.85, 0.8, 0.75, 0.7, 0.6, 0.5, 0.4, 0.3, 0.2, 0.15, 0.125, 0.1, 0.075, 0.05, 0.025, 0.02, 0.015, 0.0125, 0.01, 0.0075, 0.005, 0.004, 0.003, 0.002 0.001, 0.0005 µg/ml or less.

In another embodiment, the invention provides an antibody, or an antigen binding fragment thereof, that binds to an epitope formed by the hCMV proteins UL130 and UL131A, and neutralizes hCMV infection with an $IC_{90}$ of less than about 2 µg/ml, for example 1.9, 1.8, 1.75, 1.7, 1.6, 1.5, 1.4, 1.3, 1.25, 1.2, 1.15, 1.1, 1.05, 1, 0.95, 0.9, 0.85, 0.8, 0.75, 0.7, 0.6, 0.5, 0.4, 0.3, 0.2, 0.15, 0.125, 0.1, 0.075, 0.05, 0.025, 0.02, 0.015, 0.0125, 0.01, 0.0075, 0.005, 0.004, 0.003, 0.002 0.001, 0.0005 µg/ml or less.

In yet another embodiment, the invention provides an antibody, or an antigen binding fragment thereof, that binds to an epitope in the hCMV gH protein and neutralizes hCMV infection with an $IC_{90}$ of less than about 2 µg/ml, for example 1.9, 1.8, 1.75, 1.7, 1.6, 1.5, 1.4, 1.3, 1.25, 1.2, 1.15, 1.1, 1.05, 1, 0.95, 0.9, 0.85, 0.8, 0.75, 0.7, 0.6, 0.5, 0.4, 0.3, 0.2, 0.15, 0.125, 0.1, 0.075, 0.05, 0.025, 0.02, 0.015, 0.0125, 0.01, 0.0075, 0.005, 0.004, 0.003, 0.002 0.001, 0.0005 µg/ml or less.

In yet another embodiment, the invention provides an antibody, or an antigen binding fragment thereof, that binds to an epitope in the hCMV gB protein and neutralizes hCMV infection with an $IC_{90}$ of less than about 2 µg/ml, for example 1.9, 1.8, 1.75, 1.7, 1.6, 1.5, 1.4, 1.3, 1.25, 1.2, 1.15, 1.1, 1.05, 1, 0.95, 0.9, 0.85, 0.8, 0.75, 0.7, 0.6, 0.5, 0.4, 0.3, 0.2, 0.15, 0.125, 0.1, 0.075, 0.05, 0.025, 0.02, 0.015, 0.0125, 0.01, 0.0075, 0.005, 0.004, 0.003, 0.002 0.001, 0.0005 µg/ml or less.

In another embodiment, the invention provides an antibody, or an antigen binding fragment thereof, that binds to an epitope formed by the hCMV proteins gM and gN and neutralizes hCMV infection with an $IC_{90}$ of less than about 2 µg/ml, for example 1.9, 1.8, 1.75, 1.7, 1.6, 1.5, 1.4, 1.3, 1.25, 1.2, 1.15, 1.1, 1.05, 1, 0.95, 0.9, 0.85, 0.8, 0.75, 0.7, 0.6, 0.5, 0.4, 0.3, 0.2, 0.15, 0.125, 0.1, 0.075, 0.05, 0.025, 0.02, 0.015, 0.0125, 0.01, 0.0075, 0.005, 0.004, 0.003, 0.002 0.001, 0.0005 µg/ml or less.

Antibodies of the Invention

The invention provides antibodies having particularly high potency in neutralizing hCMV. As used herein, an "antibody that neutralizes" is one that prevents, reduces, delays or interferes with the ability of a pathogen, e.g., hCMV, to initiate and/or perpetuate an infection in a host. The antibodies of the invention and antigen-binding fragments thereof are able to neutralize hCMV infection of several kinds of cells. In one embodiment, an antibody according to the invention neutralizes infection of epithelial cells, retinal cells, endothelial cells, myeloid cells and dendritic cells. The antibodies of the invention may also neutralize hCMV infection of fibroblasts and mesenchymal stromal cells. These antibodies can be used as prophylactic or therapeutic agents upon appropriate formulation, or as a diagnostic tool, as described herein.

The antibodies of the invention may be monoclonal antibodies, human antibodies, or recombinant antibodies. In one embodiment, the antibodies of the invention are monoclonal antibodies, e.g., human monoclonal antibodies. The invention also provides fragments of the antibodies of the invention, particularly fragments that retain the antigen-binding activity of the antibodies and neutralize hCMV infection. Although the specification, including the claims, may, in some places, refer explicitly to antibody fragment(s), variant(s) and/or derivative(s) of antibodies, it is understood that the term "antibody" or "antibody of the invention" includes all categories of antibodies, namely, antibody fragment(s), variant(s) and derivative(s) of antibodies.

In one embodiment, the antibodies of the invention and antigen binding fragments thereof bind to one or more hCMV proteins. The antibodies of the invention may bind to an epitope formed by a single hCMV protein or by a combination of two or more hCMV proteins. Exemplary hCMV proteins include, but are not limited to, products of viral genes UL55 (envelope glycoprotein B, "gB"), UL75 (envelope glycoprotein H, "gH"), UL100 (glycoprotein M, "gM"), UL73 (glycoprotein N, "gN"), UL115 (glycoprotein L, "gL"), UL74 (glycoprotein O, "gO"), UL128 (glycoprotein UL128, "UL128"), UL130 (glycoprotein UL130, "UL130") or UL131A (glycoprotein UL131A, "UL131A"). In one embodiment, the antibodies of the invention bind to an epitope formed by a single hCMV protein. In another embodiment, the antibodies bind to an epitope formed by the combination of 2, 3, or more hCMV proteins.

In an exemplary embodiment, the invention comprises an antibody, or an antibody fragment thereof, that binds to an epitope in the hCMV protein UL128, or to an epitope formed by the hCMV proteins UL130 and UL131A, or to an epitope formed by the hCMV proteins UL128, UL130 and UL131A, or to an epitope formed by the hCMV proteins gH, gL, UL128, and UL130, or to an epitope in the hCMV protein gH, or the hCMV protein gB or to an epitope formed by the hCMV proteins gM and gN.

In one embodiment, the invention comprises an antibody, or an antibody fragment thereof, that binds to an epitope in UL128. In another embodiment, the invention comprises an antibody, or an antibody fragment thereof, that binds to an epitope formed by UL130 and UL131A. As used herein, an epitope formed by UL130 and UL131A means that the epitope may be formed by both UL130 and UL131A protein or may be formed by one of the two proteins, the presence of the other protein being necessary for antibody binding. In yet another embodiment, the invention comprises an antibody, or an antibody fragment thereof, that binds to an epitope formed by UL128, UL130 and UL131A. As used herein, an epitope formed by UL128, UL130 and UL131A means that the epitope may be formed by all three proteins (UL128, UL130 and UL131A) or may be formed by one or more protein(s), the presence of the other protein(s) being necessary for antibody binding. In still another embodiment, the invention comprises an antibody, or an antibody fragment thereof, that binds to an epitope formed by gH, gL, UL128, and UL130. As used herein, an epitope formed by gH, gL, UL128, and UL130 means that the epitope may be formed by all four proteins (gH, gL, UL128, and UL130) or may be formed by one or more of the four protein(s), the presence of the other protein(s) being necessary for antibody binding. In another embodiment, the invention comprises an antibody, or an antibody fragment thereof, that binds to an epitope formed by gM and gN. As used herein, an epitope formed by gM and gN means that the epitope may be formed by both gM and gN or may be formed by one of the two proteins, the presence of the other protein being necessary for antibody binding.

The sequences of the heavy chains and light chains of several exemplary antibodies of the invention, each comprising three CDRs on the heavy chain and three CDRs on the light chain have been determined. The position of the CDR amino acids are defined according to the IMGT numbering system [12, 13, 14]. The sequences of the CDRs, heavy chains, light chains as well as the sequences of the nucleic acid molecules encoding the CDRs, heavy chains, light chains are disclosed in the sequence listing. Table 1 provides the SEQ ID NOs. for the sequences of the six CDRs of the exemplary antibodies of the invention. Tables 2 and 3 provide the SEQ ID NOs for the sequences of the heavy and light chains, respectively, of the exemplary antibodies of the invention, and Table 4 provides the SEQ ID NOs for the sequences of the nucleic acid molecules encoding the CDRs, heavy chains and light chains of the antibodies.

TABLE 1

| Antibody | SEQ ID NOs. for CDRH1, CDRH3, CDRH3 | SEQ ID NOs. for CDRL1, CDRL2, CDRL3 |
|---|---|---|
| 15D8 | 188, 189, 190 | 191, 192, 193 |
| 15D8 variant 1 | 188, 204, 205 | 191, 192, 193 |
| 15D8 variant 2 | 188, 189, 210 | 191, 192, 193 |
| 4N10 | 1, 2, 3 | 4, 5, 6 |
| 10F7 | 17, 18, 19 | 20, 21, 22 |
| 10P3 | 33, 34, 35 | 36, 37, 38 |
| 4I22 | 49, 50, 51 | 52, 53, 54 |
| 8L13 | 113, 114, 115 | 116, 117, 118 |
| 2C12 | 65, 66, 67 | 68, 69, 70 |
| 8C15 | 81, 82, 83 | 84, 85, 86 |
| 9I6 | 97, 98, 99 | 100, 101, 102 |
| 7B13 | 129, 130, 131 | 132, 133, 134 |
| 8J16 | 145, 146, 147 | 148, 149, 150 |
| 8I21 | 174, 175, 176 | 177, 149, 178 |
| 7I13 | 113, 161, 162 | 163, 149, 164 |
| 7H3 | 316, 317, 318 | 319, 320, 321 |
| 7H3 variant 1 | 316, 317, 332 | 319, 320, 321 |
| 6B4 | 336, 337, 338 | 339, 340, 341 |
| 5F1 | 278, 279, 280 | 281, 282, 283 |
| 10C6 | 352, 279, 280 | 281, 282, 283 |
| 4H9 | 296, 297, 298 | 299, 300, 301 |
| 4H9 variant 1 | 296, 312, 298 | 299, 300, 301 |
| 11B12 | 232, 233, 234 | 235, 149, 236 |
| 13H11 | 216, 217, 218 | 219, 220, 221 |
| 3G16 | 246, 247, 248 | 249, 250, 251 |
| 2B11 | 360, 279, 280 | 281, 282, 361 |
| 6L3 | 262, 263, 264 | 265, 266, 267 |

TABLE 2

| Antibody | SEQ ID NOs for Heavy Chains |
|---|---|
| 15D8 | 200 |
| 15D8 variant 1 | 208 |
| 15D8 variant 2 | 212 |
| 4N10 | 13 |
| 10F7 | 29 |
| 10P3 | 45 |
| 4I22 | 61 |
| 8L13 | 125 |
| 2C12 | 77 |
| 8C15 | 93 |

TABLE 2-continued

| Antibody | SEQ ID NOs for Heavy Chains |
|---|---|
| 9I6 | 109 |
| 7B13 | 141 |
| 8J16 | 157 |
| 8I21 | 184 |
| 7I13 | 170 |
| 7H3 | 328 |
| 7H3 variant 1 | 334 |
| 6B4 | 348 |
| 5F1 | 290 |
| 5F1 variant 1 | 294 |
| 10C6 | 357 |
| 4H9 | 308 |
| 4H9 variant 1 | 314 |
| 11B12 | 242 |
| 13H11 | 228 |
| 3G16 | 258 |
| 2B11 | 367 |
| 6L3 | 274 |

TABLE 3

| Antibody | SEQ ID NO for Light Chains |
|---|---|
| 15D8 | 201 |
| 15D8 variant 1 | 201 |
| 15D8 variant 2 | 213 |
| 4N10 | 14 |
| 10F7 | 30 |
| 10P3 | 46 |
| 4I22 | 62 |
| 8L13 | 126 |
| 2C12 | 78 |
| 8C15 | 94 |
| 9I6 | 110 |
| 7B13 | 142 |
| 8J16 | 158 |
| 8I21 | 185 |
| 7I13 | 171 |
| 7H3 | 329 |
| 7H3 variant 1 | 329 |
| 6B4 | 349 |
| 5F1 | 291 |
| 5F1 variant 1 | 291 |
| 10C6 | 291 |
| 4H9 | 309 |
| 4H9 variant 1 | 309 |
| 11B12 | 243 |
| 13H11 | 229 |
| 3G16 | 259 |
| 2B11 | 368 |
| 6L3 | 275 |

TABLE 4

| Antibody | SEQ ID NO for Nucleic Acids encoding CDRs, Heavy Chains, Light Chains and Variants (CDRH1, CDRH2, CDRH3, CDRL1, CDRL2, CDRL3 and variants; Heavy Chain and variants; and Light Chains and variants) |
|---|---|
| 15D8 | 194-199 and 206, 207, 211; 202 and 209, 214; 203 and 215 |
| 4N10 | 7-12; 15; 16 |
| 10F7 | 23-28; 31; 32 |
| 10P3 | 39-44; 47; 48 |
| 4I22 | 55-60; 63; 64 |
| 8L13 | 119-124; 127; 128 |
| 2C12 | 71-76; 79; 80 |
| 8C15 | 87-92; 95; 96 |
| 9I6 | 103-108, 111, 112 |
| 7B13 | 135-140; 143; 144 |
| 8J16 | 151-156; 159; 160 |
| 8I21 | 179-182, 155, 183; 186; 187 |
| 7I13 | 165, 166, 167, 168, 155, 169; 172; 173 |

TABLE 4-continued

| Antibody | SEQ ID NO for Nucleic Acids encoding CDRs, Heavy Chains, Light Chains and Variants (CDRH1, CDRH2, CDRH3, CDRL1, CDRL2, CDRL3 and variants; Heavy Chain and variants; and Light Chains and variants) |
|---|---|
| 7H3 | 322-327 and 333; 330 and 335; 331 |
| 6B4 | 342-347; 350; 351 |
| 5F1 | 284-289; 292 and 295; 293 |
| 10C6 | 353-355, 287, 288, 356; 358; 359 |
| 4H9 | 302-307 and 313; 310 and 315; 311 |
| 11B12 | 237-240, 155, 241; 244; 245 |
| 13H11 | 222-227; 230; 231 |
| 3G16 | 252-257; 260; 261 |
| 2B11 | 362-364; 287, 365, 366; 369; 370 |
| 6L3 | 268-273; 276; 277 |

In one embodiment, the antibodies or antibody fragments of the invention comprise one or more heavy or light chain CDRs of the exemplary antibodies of the invention. In an exemplary embodiment, the antibodies or antibody fragments of the invention comprise an amino acid sequence selected from the group consisting of SEQ ID NOs: 188-193, 204-205, 210, 1-6, 17-22, 33-38, 49-54, 113-118, 65-70, 81-86, 97-102, 129-134, 145-150, 174-178, and 161-164.

In another embodiment, the antibodies of the invention comprise a heavy chain comprising an amino acid sequence of one or more of SEQ ID NOs: 188-190, 204, 205, 210, 1-3, 17-19, 33-35, 49-51, 113-115, 65-67, 81-83, 97-99, 129-131, 145-147, 174-176, 161 or 162. For example, the antibodies of the invention comprise a heavy chain comprising SEQ ID NO: 188 for CDRH1, SEQ ID NO: 189 for CDRH2, SEQ ID NO: 190 for CDRH3; SEQ ID NO: 188 for CDRH1, SEQ ID NO; 204 for CDRH2, SEQ ID NO: 205 for CDRH3; SEQ ID NO; 188 for CDRH1, SEQ ID NO: 189 for CDRH2, SEQ ID NO: 210 for CDRH3; SEQ ID NO: 1 for CDRH1, SEQ ID NO: 2 for CDRH2, SEQ ID NO: 3 for CDRH3; SEQ ID NO; 17 for CDRH1, SEQ ID NO; 18 for CDRH2, SEQ ID NO: 19 for CDRH3; SEQ ID NO: 33 for CDRH1, SEQ ID NO: 34 for CDRH2, SEQ ID NO: 35 for CDRH3; SEQ ID NO 49 for CHRH1, SEQ ID NO: 50 for CHRH2, SEQ ID NO: 51 for CDRH3; SEQ ID NO: 113 for CDRH1, SEQ ID NO: 114 for CDRH2, SEQ ID NO: 115 for CDRH3; SEQ ID NO: 65 for CDRH1, SEQ ID NO: 66 for CDRH2, SEQ ID NO: 67 for CDRH3; SEQ ID NO: 81 for CDRH1, SEQ ID NO 82 for CDRH2, SEQ ID NO: 83 for CDRH3; SEQ ID NO: 97 for CDRH1, SEQ ID NO: 98 for CDRH2, SEQ ID NO: 99 for CDRH3; SEQ ID NO: 129 for CDRH1, SEQ ID NO: 130 for CDRH2, SEQ ID NO: 131 for CDRH3; SEQ ID NO: 145 for CDRH1, SEQ ID NO: 146 for CDRH2, SEQ ID NO: 147 for CDRH3; SEQ ID NO: 174 for CDRH1, SEQ ID NO: 175 for CDRH2, SEQ ID NO: 176 for CDRH3; and SEQ ID NO: 113 for CDRH1, SEQ ID NO: 161 for CDRH2, SEQ ID NO: 162 for CDRH3.

In yet another embodiment, the antibodies of the invention comprise a light chain comprising an amino acid sequence of one or more of SEQ ID NOs: 191-193, 4-6, 20-22, 36-38, 52-54, 116-118, 68-70, 84-86, 100-102, 132-134, 148-150, 177, 178, 163, or 164. For example, the antibodies of the invention comprise a light chain comprising SEQ ID NO: 191 for CDRL1, SEQ ID NO: 192 for CDRL2; SEQ ID NO: 193 for CDRL3; SEQ ID NO: 4 for CDRL1, SEQ ID NO: 5 for CDRL2 and SEQ ID NO: 6 for CDRL3; SEQ ID NO: 20 for CDRL1, SEQ ID NO: 21 for CDRL2, SEQ ID NO: 22 for CDRL3; SEQ ID NO; 36 for CDRL1, SEQ ID NO: 37 for CDRL2, SEQ ID NO: 38 for CDRL3; SEQ ID NO: 52 for CDRL1, SEQ ID NO: 53 for CDRL2, SEQ ID NO: 54 for CDRL3; SEQ ID NO: 116 for CDRL1, SEQ ID NO: 117 for CDRL2, SEQ ID NO: 118 for CDRL3; SEQ ID NO: 68 for CDRL1, SEQ ID NO: 69 for CDRL2, SEQ ID NO: 70 for CDRL3; SEQ ID NO 84 for CDRL1, SEQ ID NO: 85 for CDRL2, SEQ ID NO: 86 for CDRL3; SEQ ID NO: 100 for CDRL1, SEQ ID NO: 101 for CDRL2, SEQ ID NO: 102 for CDRL3; SEQ ID NO: 132 for CDRL1, SEQ ID NO: 133 for CDRL2, SEQ ID NO: 134 for CDRL3; SEQ ID NO: 148 for CDRL1, SEQ ID NO: 149 for CDRL2, SEQ ID NO: 150 for CDRL3; SEQ ID NO: 177 for CDRL1, SEQ ID NO: 149 for CDRL2, SEQ ID NO: 178 for CDRL3; SEQ ID NO: 163 for CDRL1, SEQ ID NO: 149 for CDRL2 and SEQ ID NO: 164 for CDRL3.

In still another embodiment, the antibodies of the invention comprise a heavy chain with an amino acid sequence that is at least 70% identical to those of SEQ ID NOs: 200, 208, 212, 13, 29, 45, 61, 125, 77, 93, 109, 141, 157, 184, or 170, and neutralize hCMV infection. In one embodiment, the antibody binds to an epitope in the hCMV UL128 protein and comprises a heavy chain having an amino acid sequence that is at least 70%, at least 75%, at least 80%, at least 85%, at least 90%, at least 95%, at least 98%, or at least 99% identical to the amino acid sequence of SEQ ID NO: 200, 208 or 212, and neutralizes hCMV infection. In one embodiment, an antibody according to the invention comprises a heavy chain having the sequence recited in SEQ ID NO: 200, 208 or 212, and neutralizes hCMV infection.

In another embodiment, the antibody binds to an epitope formed by the hCMV proteins UL130 and UL131A and comprises a heavy chain having an amino acid sequence that is at least 70%, at least 75%, at least 80%, at least 85%, at least 90%, at least 95%, at least 98%, or at least 99% identical to the amino acid sequence of SEQ ID NO: 13, 29, 45, 61 or 125, and neutralizes hCMV infection. In one embodiment, an antibody according to the invention comprises a heavy chain having the sequence recited in SEQ ID NO: 13, 29, 45, 61 or 125, and neutralizes hCMV infection.

In yet another embodiment, the antibody binds to an epitope formed by the hCMV proteins UL128, UL130 and UL131A and comprises a heavy chain having an amino acid sequence that is at least 70%, at least 75%, at least 80%, at least 85%, at least 90%, at least 95%, at least 98%, or at least 99% identical to the amino acid sequence of SEQ ID NO: 77, 93, 109, 141, 157, or 170, and neutralizes hCMV infection. In one embodiment, an antibody according to the invention comprises a heavy chain having the sequence recited in SEQ ID NO: 77, 93, 109, 141, 157, or 170, and neutralizes hCMV infection.

In a further embodiment, the antibody binds to an epitope formed by the hCMV proteins gH, gL, UL128 and UL130 and comprises a heavy chain having an amino acid sequence that is at least 70%, at least 75%, at least 80%, at least 85%, at least 90%, at least 95%, at least 98%, or at least 99% identical to the amino acid sequence of SEQ ID NO: 184, and neutralizes hCMV infection. In one embodiment, an antibody according to the invention comprises a heavy chain having the sequence recited in SEQ ID NO: 184, and neutralizes hCMV infection.

In yet another embodiment, the antibodies of the invention comprise a light chain with an amino acid sequence that is at least 70% identical to those of SEQ ID NOs: 201, 213, 14, 30, 46, 62, 126, 78, 94, 110, 142, 158, 185, or 171, and neutralize hCMV infection.

In one embodiment, the antibody binds to an epitope in the hCMV UL128 protein and comprises a light chain having an amino acid sequence that is at least 70%, at least 75%, at least 80%, at least 85%, at least 90%, at least 95%, at least 98%, or at least 99% identical to the amino acid sequence of SEQ ID NO: 201 or 213, and neutralizes hCMV infection. In one embodiment, an antibody according to the invention comprises a light chain having the sequence recited in SEQ ID NO: 201 or 213, and neutralizes hCMV infection.

In one embodiment, the antibody binds to an epitope formed by the hCMV proteins UL130 and UL131A and comprises a light chain having an amino acid sequence that is at least 70%, at least 75%, at least 80%, at least 85%, at least 90%, at least 95%, at least 98%, or at least 99% identical to the amino acid sequence of SEQ ID NO: 14, 30, 46, 62 or 126, and neutralizes hCMV infection. In one embodiment, an antibody according to the invention comprises a light chain having the sequence recited in SEQ ID NO: 14, 30, 46, 62 or 126, and neutralizes hCMV infection.

In another embodiment, the antibody binds to an epitope formed by the hCMV proteins UL128, UL130 and UL131A and comprises a light chain having an amino acid sequence that is at least 70%, at least 75%, at least 80%, at least 85%, at least 90%, at least 95%, at least 98%, or at least 99% identical to the amino acid sequence of SEQ ID NO: 78, 94, 110, 142, 158, or 171, and neutralizes hCMV infection. In one embodiment, an antibody according to the invention comprises a light chain having the sequence recited in SEQ ID NO: 78, 94, 110, 142, 158, or 171, and neutralizes hCMV infection.

In a further embodiment, the antibody binds to an epitope formed by the hCMV proteins gH, gL, UL128 and UL130 and comprises a light chain having an amino acid sequence that is at least 70%, at least 75%, at least 80%, at least 85%, at least 90%, at least 95%, at least 98%, or at least 99% identical to the amino acid sequence of SEQ ID NO: 185, and neutralizes hCMV infection. In one embodiment, an antibody according to the invention comprises a light chain having the sequence recited in SEQ ID NO: 185, and neutralizes hCMV infection.

In another embodiment, the antibodies or antibody fragments of the invention comprise one or more heavy or light chain CDRs of the exemplary antibodies of the invention. In an exemplary embodiment, the antibodies or antibody fragments of the invention comprise an amino acid sequence selected from the group consisting of SEQ ID NOs: 316-321, 332, 336-341, 278-283, 352, 296-301, 312, 232-236, 149, 216-221, 246-251, 360, 361 and 262-267, and neutralize hCMV infection.

In yet another embodiment, the antibodies of the invention comprise a heavy chain comprising an amino acid sequence of one or more of SEQ ID NOs: 316-318, 332, 336-338, 278-280, 352, 296-298, 312, 232-234, 216-218, 246-248, 360, 361 and 262-264. For example, the antibodies of the invention comprise a heavy chain comprising SEQ ID NO: 316 for CDRH1, SEQ ID NO: 317 for CDRH2, SEQ ID NO: 318 for CDRH3; SEQ ID NO: 316 for CDRH1, SEQ ID NO: 317 for CDRH2, and SEQ ID NO: 332 for CDRH3; SEQ ID NO: 336 for CDRH1, SEQ ID NO: 337 for CDRH2, SEQ ID NO: 338 for CDRH3; SEQ ID NO: 278 for CDRH1, SEQ ID NO: 279 for CDRH2, SEQ ID NO: 280 for CDRH3; SEQ ID NO: 352 for CDRH1, SEQ ID NO: 279 for CDRH2, SEQ ID NO: 280 for CDRH3; SEQ ID NO: 296 for CDRH1, SEQ ID NO: 297 for CDRH2, SEQ ID NO: 298 for CDRH3; SEQ ID NO: 296 for CDRH1, SEQ ID NO: 312 for CDRH2, SEQ ID NO: 298 for CDRH3; SEQ ID NO: 232 for CDRH1, SEQ ID NO: 233 for CDRH2, SEQ ID NO: 234 for CDRH3; SEQ ID NO: 216 for CDRH1, SEQ ID NO: 217 for CDRH2, SEQ ID NO: 218 for CDRH3; SEQ ID NO: 246 for CDRH1, SEQ ID NO: 247 for CDRH2, SEQ ID NO: 248 for CDRH3; and SEQ ID NO: 360 for CDRH1, SEQ ID NO: 279 for CDRH2, SEQ ID NO: 280 for CDRH3; and SEQ ID NO: 262 for CDRH1, SEQ ID NO: 263 for CDRH2, SEQ ID NO: 264 for CDRH3.

In still another embodiment, the antibodies of the invention comprise a light chain comprising an amino acid sequence of one or more of SEQ ID NOs: 319-321, 339-341, 281-283, 299-301, 149, 235, 236, 219-221, 249-251, 265-267. For example, the antibodies of the invention comprise a light chain comprising SEQ ID NO: 319 for CDRL1, SEQ ID NO: 320 for CDRL2, SEQ ID NO: 321 for CDRL3; SEQ ID NO: 339 for CDRL1, SEQ ID NO: 340 for CDRL2, SEQ ID NO: 341 for CDRL3; SEQ ID NO: 281 for CDRL1, SEQ ID NO: 282 for CDRL2, SEQ ID NO: 283 for CDRL3; SEQ ID NO: 299 for CDRL1, SEQ ID NO: 300 for CDRL2, SEQ ID NO: 301 for CDRL3; SEQ ID NO: 235 for CDRL1, SEQ ID NO: 149 for CDRL2, SEQ ID NO: 236 for CDRL3; SEQ ID NO: 219 for CDRL1, SEQ ID NO: 220 for CDRL2, SEQ ID NO: 221 for CDRL3; SEQ ID NO: 249 for CDRL1, SEQ ID NO: 250 for CDRL2, SEQ ID NO: 251 for CDRL3; and SEQ ID NO: 281 for CDRL1, SEQ ID NO: 282 for CDRL2, SEQ ID NO: 361 for CDRL3; and SEQ ID NO: 265 for CDRL1, SEQ ID NO: 266 for CDRL2, SEQ ID NO: 267 for CDRL3.

In a further embodiment, the antibodies of the invention comprise a heavy chain with an amino acid sequence that is at least 70% identical to those of SEQ ID NOs: 328, 334, 348, 290, 294, 357, 308, 314, 242, 228, 258, 367 or 274, and neutralizes hCMV infection.

In one embodiment, the antibody binds to an epitope in the hCMV gB protein and comprises a heavy chain having an amino acid sequence that is at least 70%, at least 75%, at least 80%, at least 85%, at least 90%, at least 95%, at least 98%, or at least 99% identical to the amino acid sequence of SEQ ID NO: 328, 334, 348, 290, 294, 308, 357, 314 or 367, and neutralizes hCMV infection. In one embodiment, an antibody according to the invention comprises a heavy chain having the sequence recited in SEQ ID NO: 328, 334, 348, 290, 294, 308, 357, 314 or 367 and neutralizes hCMV infection.

In another embodiment, the antibody binds to an epitope in the hCMV gH protein and comprises a heavy chain having an amino acid sequence that is at least 70%, at least 75%, at least 80%, at least 85%, at least 90%, at least 95%, at least 98%, or at least 99% identical to the amino acid sequence of SEQ ID NO: 242, 228, or 258, and neutralizes hCMV infection. In one embodiment, an antibody according to the invention comprises a heavy chain having the sequence recited in SEQ ID NO: 242, 228, or 258, and neutralizes hCMV infection.

In another embodiment, the antibody binds to an epitope formed by the hCMV proteins gM and gN and comprises a heavy chain having an amino acid sequence that is at least 70%, at least 75%, at least 80%, at least 85%, at least 90%, at least 95%, at least 98%, or at least 99% identical to the amino acid sequence of SEQ ID NO: 274, and neutralizes hCMV infection. In one embodiment, an antibody according to the invention comprises a heavy chain having the sequence recited in SEQ ID NO: 274, and neutralizes hCMV infection.

In yet another embodiment, the antibodies of the invention comprise a light chain with an amino acid sequence that is at least 70% identical to those of SEQ ID NOs: 329, 349, 291, 309, 243, 229, 259, 368 or 275, and neutralize hCMV infection.

In one embodiment, the antibody binds to an epitope in the hCMV gB protein and comprises a light chain having an amino acid sequence that is at least 70%, at least 75%, at least 80%, at least 85%, at least 90%, at least 95%, at least 98%, or at least 99% identical to the amino acid sequence of SEQ ID NO: 329, 349, 291, 309, or 368 and neutralizes hCMV infection. In one embodiment, an antibody according to the invention comprises a light chain having the sequence recited in SEQ ID NO: 329, 349, 291, 309 or 368, and neutralizes hCMV infection.

In another embodiment, the antibody binds to an epitope in the hCMV gH protein and comprises a light chain having an amino acid sequence that is at least 70%, at least 75%, at least 80%, at least 85%, at least 90%, at least 95%, at least 98%, or at least 99% identical to the amino acid sequence of SEQ ID NO: 243, 229, or 259, and neutralizes hCMV infection. In one embodiment, an antibody according to the invention comprises a light chain having the sequence recited in SEQ ID NO: 243, 229, or 259, and neutralizes hCMV infection.

In another embodiment, the antibody binds to an epitope formed by the hCMV proteins gM and gN and comprises a light chain having an amino acid sequence that is at least 70%, at least 75%, at least 80%, at least 85%, at least 90%, at least 95%, at least 98%, or at least 99% identical to the amino acid sequence of SEQ ID NO: 275, and neutralizes hCMV infection. In one embodiment, an antibody according to the invention comprises a light chain having the sequence recited in SEQ ID NO: 275, and neutralizes hCMV infection.

In one embodiment, the antibody of the invention is not MSL-109, 8F9, 3E3 or R551A. In another embodiment, the antibody of the invention is not 1F11, 2F4, 5A2 or 6G4, disclosed in U.S. application Ser. Nos. 11/969,104 and 12/174,568.

Exemplary antibodies of the invention include, but are not limited to, 15D8, 4N10, 10F7, 10P3, 4I22, 8L13, 2C12, 8C15, 9I6, 7B13, 8J16, 8I21, 7I13, 7H3, 6B4, 5F1, 10C6, 4H9, 2B11, 11B12, 13H11, 3G16 and 6L3.

Variants of 15D8 that neutralize hCMV infection consist of a heavy chain variant having amino acid sequence recited in SEQ ID NO: 208 ("15D8 variant 1"), and SEQ ID NO: 212 ("15D8 variant 2"), and a light chain having the amino acid sequence recited in SEQ ID NO: 213 (15D8 variant 2). The nucleic acid sequences encoding the variant heavy chain variants are recited in SEQ ID NO: 209 (15D8 variant 1) and SEQ ID NO: 214 (15D8 variant 2). The nucleic acid encoding the variant light chain is recited in SEQ ID NO: 215 (15D8 variant 2). Thus, antibodies comprising the 15D8 variant heavy chains (SEQ ID NO: 208, 212) and variant light chain (SEQ ID NO: 213) that neutralize hCMV infection are included within the scope of the invention.

As used herein, the term "15D8" is used to refer to any and/or all variants of 15D8 that neutralize hCMV infection, for example, those with heavy chains corresponding to SEQ ID NO: 208 and 212 and light chains corresponding to SEQ ID NO; 213.

A variant of 7H3 that neutralizes hCMV infection consists of a heavy chain having the amino acid sequence recited in SEQ ID NO: 334 ("7H3 variant 1"). The nucleic acid sequence encoding the variant heavy chain is recited in SEQ ID NO: 335. Thus, antibodies comprising the 7H3 variant heavy chain (SEQ ID NO: 334) that neutralize hCMV infection are included within the scope of the invention.

As used herein, the term "7H3" is used to refer to any and/or all variants of 7H3 that neutralize hCMV infection, for example, those with heavy chains corresponding to SEQ ID NO:334.

A variant of 5F1 that neutralizes hCMV infection consists of a heavy chain having the amino acid sequence recited in SEQ ID NO: 294 ("5F1 variant 1"). The nucleic acid sequence encoding the variant heavy chain is recited in SEQ ID NO: 295. Thus, antibodies comprising the 5F1 variant heavy chain (SEQ ID NO: 294) that neutralize hCMV infection are included within the scope of the invention.

As used herein, the term "5F1" is used to refer to any and/or all variants of 5F1 that neutralize hCMV infection, for example, those with heavy chains corresponding to SEQ ID NO:294.

A variant of 4H9 that neutralizes hCMV infection consists of a heavy chain having the amino acid sequence recited in SEQ ID NO: 314 ("4H9 variant 1"). The nucleic acid sequence encoding the variant heavy chain is recited in SEQ ID NO: 315. Thus, antibodies comprising the 4H9 variant heavy chain (SEQ ID NO: 314), that neutralize hCMV infection are included within the scope of the invention.

As used herein, the term "4H9" is used to refer to any and/or all variants of 4H9 that neutralize hCMV infection, for example, those with heavy chains corresponding to SEQ ID NO:314.

In one embodiment, an antibody of the invention, or antigen binding fragment thereof, comprises all of the CDRs of antibody 15D8 as listed in Table 1, and neutralizes hCMV infection in a human host. In another embodiment, an antibody of the invention, or antigen binding fragment thereof, comprises all of the CDRs of antibody 15D8 variant 1 as listed in Table 1, and neutralizes hCMV infection in a human host. In another embodiment, an antibody of the invention, or antigen binding fragment thereof, comprises all of the CDRs of antibody 15D8 variant 2 as listed in Table 1, and neutralizes hCMV infection in a human host. In yet another embodiment, an antibody of the invention, or antigen binding fragment thereof, comprises all of the CDRs of antibody 8I21 as listed in Table 1, and neutralizes hCMV infection in a human host.

In yet another embodiment, an antibody of the invention, or antigen binding fragment thereof, comprises all of the CDRs of antibody 4N10 as listed in Table 1, and neutralizes hCMV infection in a human host. In another embodiment, an antibody of the invention, or antigen binding fragment thereof, comprises all of the CDRs of antibody 10F7 as listed in Table 1, and neutralizes hCMV infection in a human host. In another embodiment, an antibody of the invention, or antigen binding fragment thereof, comprises all of the CDRs of antibody 10P3 as listed in Table 1, and neutralizes hCMV infection in a human host. In another embodiment, an antibody of the invention, or antigen binding fragment thereof, comprises all of the CDRs of antibody 4I22 as listed in Table 1, and neutralizes hCMV infection in a human host. In another embodiment, an antibody of the invention, or antigen binding fragment thereof, comprises all of the CDRs of antibody 8L13 as listed in Table 1, and neutralizes hCMV infection in a human host.

In yet another embodiment, an antibody of the invention, or antigen binding fragment thereof, comprises all of the CDRs of antibody 2C12 as listed in Table 1, and neutralizes hCMV infection in a human host. In another embodiment, an antibody of the invention, or antigen binding fragment thereof, comprises all of the CDRs of antibody 8C15 as listed in Table 1, and neutralizes hCMV infection in a human host. In another embodiment, an antibody of the invention, or antigen binding fragment thereof, comprises all of the CDRs of antibody 9I6 as listed in Table 1, and neutralizes hCMV infection in a human host. In another embodiment, an antibody of the invention, or antigen binding fragment thereof, comprises all of the CDRs of antibody 7B13 as listed in Table 1, and neutralizes hCMV infection in a human host. In another embodiment, an antibody of the invention, or antigen binding fragment thereof, comprises all of the CDRs of antibody 8J16 as listed in Table 1, and neutralizes hCMV infection in a human host. In another embodiment, an antibody of the invention, or antigen binding fragment thereof, comprises all of the CDRs of antibody 7I13 as listed in Table 1, and neutralizes hCMV infection in a human host.

In yet another embodiment, an antibody of the invention, or antigen binding fragment thereof, comprises all of the CDRs of antibody 7H3 as listed in Table 1, and neutralizes hCMV infection in a human host. In another embodiment, an antibody of the invention, or antigen binding fragment thereof, comprises all of the CDRs of antibody 7H3 variant 1 as listed in Table 1, and neutralizes hCMV infection in a human host. In another embodiment, an antibody of the invention, or antigen binding fragment thereof, comprises all of the CDRs of antibody 6B4 as listed in Table 1, and neutralizes hCMV infection in a human host. In another embodiment, an antibody of the invention, or antigen binding fragment thereof, comprises all of the CDRs of antibody 5F1 as listed in Table 1, and neutralizes hCMV infection in a human host. In another embodiment, an antibody of the invention, or antigen binding fragment thereof, comprises all of the CDRs of antibody 10C6 as listed in Table 1, and neutralizes hCMV infection in a human host. In another embodiment, an antibody of the invention, or antigen binding fragment thereof, comprises all of the CDRs of antibody 4H9 as listed in Table 1, and neutralizes hCMV infection in a human host. In another embodiment, an antibody of the invention, or antigen binding fragment thereof, comprises all of the CDRs of antibody 4H9 variant 1 as listed in Table 1, and neutralizes hCMV infection in a human host. In another embodiment, an antibody of the invention, or antigen binding fragment thereof, comprises all of the CDRs of antibody 2B11 as listed in Table 1, and neutralizes hCMV infection in a human host.

In yet another embodiment, an antibody of the invention, or antigen binding fragment thereof, comprises all of the CDRs of antibody 11B12 as listed in Table 1, and neutralizes hCMV infection in a human host. In another embodiment, an antibody of the invention, or antigen binding fragment thereof, comprises all of the CDRs of antibody 13H11 as listed in Table 1, and neutralizes hCMV infection in a human host. In another embodiment, an antibody of the invention, or antigen binding fragment thereof, comprises all of the CDRs of antibody 3G16 as listed in Table 1, and neutralizes hCMV infection in a human host. In yet another embodiment, an antibody of the invention, or antigen binding fragment thereof, comprises all of the CDRs of antibody 6L3 as listed in Table 1, and neutralizes hCMV infection in a human host.

The invention further comprises an antibody, or fragment thereof, that binds to an epitope capable of binding to an antibody of the invention, or an antibody that competes with an antibody of the invention.

Antibodies of the invention also include hybrid antibody molecules that comprise one or more CDRs from an antibody of the invention and one or more CDRs from another antibody to the same epitope. In one embodiment, such hybrid antibodies comprise three CDRs from an antibody of the invention and three CDRs from another antibody to the same epitope. Exemplary hybrid antibodies comprise i) the three light chain CDRs from an antibody of the invention and the three heavy chain CDRs from another antibody to the same epitope, or ii) the three heavy chain CDRs from an antibody of the invention and the three light chain CDRs from another antibody to the same epitope.

In another aspect, the invention also includes nucleic acid sequences encoding part or all of the light and heavy chains and CDRs of the antibodies of the present invention. In one embodiment, nucleic acid sequences according to the invention include nucleic acid sequences having at least 70%, at least 75%, at least 80%, at least 85%, at least 90%, at least 95%, at least 98%, or at least 99% identity to the nucleic acid encoding a heavy or light chain of an antibody of the invention. In another embodiment, a nucleic acid sequence of the invention has the sequence of a nucleic acid encoding a heavy or light chain CDR of an antibody of the invention. For example, a nucleic acid sequence according to the invention comprises a sequence that is at least 75% identical to the nucleic acid sequences of SEQ ID NOs: 7-12, 15, 16, 23-28, 31, 32, 39-44, 47, 48, 55-60, 63, 64, 71-76, 79, 80, 87-92, 95, 96, 103-108, 111, 112, 119-124, 127, 128, 135-140, 143, 144, 151-156, 159, 160, 165-169, 172, 173, 179-183, 186, 187, 194-199, 202, 203, 206, 207, 209, 211, 214, 215, 222-227, 230, 231, 237-241, 244, 245, 252-257, 260, 261, 268-273, 276, 277, 284-289, 292, 293, 295, 302-307, 310, 311, 313, 315, 322-327, 330, 331, 333, 335, 342-347, 350, 351, 353-356, 358, 359, 362-364, 365, 366, 369 and 370. In one embodiment, the nucleic acid sequence according to the invention comprises a sequence that is at least 80%, at least 85%, at least 90%, at least 95%, at least 97%, at least 98%, or at least 99% identical to the nucleic acid sequences of the above listed SEQ ID NOs.

Due to the redundancy of the genetic code, variants of these sequences will exist that encode the same amino acid sequences. These variants are included within the scope of the invention.

Variant antibodies that neutralize hCMV infection are also included within the scope of the invention. Thus, variants of the sequences recited in the application are also included within the scope of the invention. Such variants include natural variants generated by somatic mutation in vivo during the immune response or in vitro upon culture of immortalized B cell clones. Alternatively, variants may arise due to the degeneracy of the genetic code, as mentioned above or may be produced due to errors in transcription or translation.

Further variants of the antibody sequences having improved affinity and/or potency may be obtained using methods known in the art and are included within the scope of the invention. For example, amino acid substitutions may be used to obtain antibodies with further improved affinity. Alternatively, codon optimisation of the nucleotide sequence may be used to improve the efficiency of translation in expression systems for the production of the antibody. Further, polynucleotides comprising a sequence optimized for antibody specificity or neutralizing activity by the application of a directed evolution method to any of the nucleic acid sequences of the invention are also within the scope of the invention.

In one embodiment variant antibody sequences that neutralize hCMV infection may share 70% or more (i.e. 75%, 80%, 85%, 90%, 95%, 97%, 98%, 99% or more) amino acid sequence identity with the sequences recited in the application. In some embodiments such sequence identity is calculated with regard to the full length of the reference sequence (i.e. the sequence recited in the application). In some further embodiments, percentage identity, as referred to herein, is as determined using BLAST version 2.1.3 using the default parameters specified by the NCBI (the National Center for Biotechnology Information) [Blosum 62 matrix; gap open penalty=11 and gap extension penalty=1].

Further included within the scope of the invention are vectors, for example expression vectors, comprising a nucleic acid sequence according to the invention. Cells transformed with such vectors are also included within the scope of the invention. Examples of such cells include but are not limited to, eukaryotic cells, e.g. yeast cells, animal cells or plant cells. In one embodiment the cells are mammalian, e.g. human, CHO, HEK293T, PER.C6, NS0, myeloma or hybridoma cells.

The invention also relates to monoclonal antibodies that bind to an epitope capable of binding the antibodies of the invention, including, but not limited to, a monoclonal antibody selected from the group consisting of 15D8, 4N10, 10F7, 10P3, 4I22, 8L13, 2C12, 8C15, 9I6, 7B13, 8J16, 8I21, 7I13, 7H3, 6B4, 5F1, 10C6, 4H9, 11B12, 13H11, 3G16, 2B11 and 6L3.

Monoclonal and recombinant antibodies are particularly useful in identification and purification of the individual polypeptides or other antigens against which they are directed. The antibodies of the invention have additional utility in that they may be employed as reagents in immunoassays, radioimmunoassays (RIA) or enzyme-linked immunosorbent assays (ELISA). In these applications, the antibodies can be labelled with an analytically-detectable reagent such as a radioisotope, a fluorescent molecule or an enzyme. The antibodies may also be used for the molecular identification and characterisation (epitope mapping) of antigens.

Antibodies of the invention can be coupled to a drug for delivery to a treatment site or coupled to a detectable label to facilitate imaging of a site comprising cells of interest, such as cells infected with hCMV. Methods for coupling antibodies to drugs and detectable labels are well known in the art, as are methods for imaging using detectable labels. Labelled antibodies may be employed in a wide variety of assays, employing a wide variety of labels. Detection of the formation of an antibody-antigen complex between an antibody of the invention and an epitope of interest (an hCMV epitope) can be facilitated by attaching a detectable substance to the antibody. Suitable detection means include the use of labels such as radionuclides, enzymes, coenzymes, fluorescers, chemiluminescers, chromogens, enzyme substrates or co-factors, enzyme inhibitors, prosthetic group complexes, free radicals, particles, dyes, and the like. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material is luminol; examples of bioluminescent materials include luciferase, luciferin, and aequorin; and examples of suitable radioactive material include $^{125}$I, $^{131}$I, $^{35}$S, or $^{3}$H. Such labeled reagents may be used in a variety of well-known assays, such as radioimmunoassays, enzyme immunoassays, e.g., ELISA, fluorescent immunoassays, and the like. See for example, references 15-18.

An antibody according to the invention may be conjugated to a therapeutic moiety such as a cytotoxin, a therapeutic agent, or a radioactive metal ion or radioisotope. Examples of radioisotopes include, but are not limited to, I-131, I-123, I-125, Y-90, Re-188, Re-186, At-211, Cu-67, Bi-212, Bi-213, Pd-109, Tc-99, In-111, and the like. Such antibody conjugates can be used for modifying a given biological response; the drug moiety is not to be construed as limited to classical chemical therapeutic agents. For example, the drug moiety may be a protein or polypeptide possessing a desired biological activity. Such proteins may include, for example, a toxin such as abrin, ricin A, *pseudomonas* exotoxin, or diphtheria toxin.

Techniques for conjugating such therapeutic moiety to antibodies are well known. See, for example, Amon et al. (1985) "Monoclonal Antibodies for Immunotargeting of Drugs in Cancer Therapy," in *Monoclonal Antibodies and Cancer Therapy*, ed. Reisfeld et al. (Alan R. Liss, Inc.), pp. 243-256; ed. Hellstrom et al. (1987) "Antibodies for Drug Delivery," in *Controlled Drug Delivery*, ed. Robinson et al. (2d ed; Marcel Dekker, Inc.), pp. 623-653; Thorpe (1985) "Antibody Carriers of Cytotoxic Agents in Cancer Therapy: A Review," in *Monoclonal Antibodies '84: Biological and Clinical Applications*, ed. Pinchera et al. pp. 475-506 (Editrice Kurtis, Milano, Italy, 1985); "Analysis, Results, and Future Prospective of the Therapeutic Use of Radiolabeled Antibody in Cancer Therapy," in *Monoclonal Antibodies for Cancer Detection and Therapy*, ed. Baldwin et al. (Academic Press, New York, 1985), pp. 303-316; and Thorpe et al. (1982) *Immunol. Rev.* 62:119-158.

Alternatively, an antibody can be conjugated to a second antibody to form an antibody heteroconjugate as described in reference 19. In addition, linkers may be used between the labels and the antibodies of the invention [20]. Antibodies or, antigen-binding fragments thereof may be directly labelled with radioactive iodine, indium, yttrium, or other radioactive particle known in the art [21]. Treatment may consist of a combination of treatment with conjugated and non-conjugated antibodies administered simultaneously or subsequently [22, 23].

Antibodies of the invention may also be attached to a solid support.

Additionally, antibodies of the invention, or functional antibody fragments thereof, can be chemically modified by covalent conjugation to a polymer to, for example, increase their circulating half-life, for example. Examples of polymers, and methods to attach them to peptides, are shown in references 24-27. In some embodiments the polymers may be selected from polyoxyethylated polyols and polyethylene glycol (PEG). PEG is soluble in water at room temperature and has the general formula: $R(O-CH_2-CH_2)_nO-R$ where R can be hydrogen, or a protective group such as an alkyl or alkanol group. In one embodiment the protective group may have between 1 and 8 carbons. In a further embodiment the protective group is methyl. The symbol n is a positive integer. In one embodiment n is between 1 and 1,000. In another embodiment n is between 2 and 500. In one embodiment the PEG has an average molecular weight between 1,000 and 40,000. In a further embodiment the PEG has a molecular weight between 2,000 and 20,000. In yet a further embodiment the PEG has a molecular weight of between 3,000 and 12,000. In one embodiment PEG has at least one hydroxy group. In another embodiment the PEG has a terminal hydroxy group. In yet another embodiment it is the terminal hydroxy group which is activated to react with a free amino group on the inhibitor. However, it will be understood that the type and amount of the reactive groups may be varied to achieve a covalently conjugated PEG/antibody of the present invention.

Water-soluble polyoxyethylated polyols are also useful in the present invention. They include polyoxyethylated sorbitol, polyoxyethylated glucose, polyoxyethylated glycerol (POG), and the like. In one embodiment. POG is used.

Without being bound by any theory, because the glycerol backbone of polyoxyethylated glycerol is the same backbone occurring naturally in, for example, animals and humans in mono-, di-, triglycerides, this branching would not necessarily be seen as a foreign agent in the body. In some embodiments POG has a molecular weight in the same range as PEG. The structure for POG is shown in reference 28, and a discussion of POG/IL-2 conjugates is found in reference 24.

Another drug delivery system that can be used for increasing circulatory half-life is the liposome. Methods of preparing liposome delivery systems are discussed in references 29, 30 and 31. Other drug delivery systems are known in the art and are described in, for example, references 32 and 33.

Antibodies of the invention may be provided in purified form. Typically, the antibody will be present in a composition that is substantially free of other polypeptides e.g. where less than 90% (by weight), usually less than 60% and more usually less than 50% of the composition is made up of other polypeptides.

Antibodies of the invention may be immunogenic in non-human (or heterologous) hosts e.g. in mice. In particular, the antibodies may have an idiotope that is immunogenic in non-human hosts, but not in a human host. Antibodies of the invention for human use include those that cannot be easily isolated from hosts such as mice, goats, rabbits, rats, non-primate mammals, etc. and cannot generally be obtained by humanisation or from xeno-mice.

Antibodies of the invention can be of any isotype (e.g. IgA, IgG, IgM i.e. an α, γ or μ heavy chain), but will generally be IgG. Within the IgG isotype, antibodies may be IgG1, IgG2, IgG3 or IgG4 subclass. Antibodies of the invention may have a κ or a λ light chain.

Production of Antibodies

Monoclonal antibodies according to the invention can be made by any method known in the art. The general methodology for making monoclonal antibodies using hybridoma technology is well known [34, 35]. Preferably, the alternative EBV immortalisation method described in reference 36 is used.

Using the method described in reference 36, B cells producing the antibody of the invention can be transformed with EBV in the presence of a polyclonal B cell activator. Transformation with EBV is a standard technique and can easily be adapted to include polyclonal B cell activators.

Additional stimulants of cellular growth and differentiation may optionally be added during the transformation step to further enhance the efficiency. These stimulants may be cytokines such as IL-2 and IL-15. In one aspect, IL-2 is added during the immortalisation step to further improve the efficiency of immortalisation, but its use is not essential.

The immortalised B cells produced using these methods can then be cultured using methods known in the art and antibodies isolated therefrom.

The antibodies of the invention can also be made by culturing single plasma cells in microwell culture plates using the method described in UK Patent Application 0819376.5. Further, from single plasma cell cultures, RNA can be extracted and single cell PCR can be performed using methods known in the art. The VH and VL regions of the antibodies can be amplified by RT-PCR, sequenced and cloned into an expression vector that is then transfected into HEK293T cells or other host cells. The cloning of nucleic acid in expression vectors, the transfection of host cells, the culture of the transfected host cells and the isolation of the produced antibody can be done using any methods known to one of skill in the art.

Monoclonal antibodies may be further purified, if desired, using filtration, centrifugation and various chromatographic methods such as HPLC or affinity chromatography. Techniques for purification of monoclonal antibodies, including techniques for producing pharmaceutical-grade antibodies, are well known in the art.

Fragments of the monoclonal antibodies of the invention can be obtained from the monoclonal antibodies by methods that include digestion with enzymes, such as pepsin or papain, and/or by cleavage of disulfide bonds by chemical reduction. Alternatively, fragments of the monoclonal antibodies can be obtained by cloning and expression of part of the sequences of the heavy or light chains. Antibody "fragments" may include Fab, Fab', F(ab')$_2$ and Fv fragments. The invention also encompasses single-chain Fv fragments (scFv) derived from the heavy and light chains of a monoclonal antibody of the invention e.g. the invention includes a scFv comprising the CDRs from an antibody of the invention. Also included are heavy or light chain monomers and dimers as well as single chain antibodies, e.g. single chain Fv in which the heavy and light chain variable domains are joined by a peptide linker.

Standard techniques of molecular biology may be used to prepare DNA sequences coding for the antibodies or fragments of the antibodies of the present invention. Desired DNA sequences may be synthesised completely or in part using oligonucleotide synthesis techniques. Site-directed mutagenesis and polymerase chain reaction (PCR) techniques may be used as appropriate.

Any suitable host cell/vector system may be used for expression of the DNA sequences encoding the antibody molecules of the present invention or fragments thereof. Bacterial, for example E. coli, and other microbial systems may be used, in part, for expression of antibody fragments such as Fab and F(ab')$_2$ fragments, and especially Fv fragments and single chain antibody fragments, for example, single chain Fvs. Eukaryotic, e.g. mammalian, host cell expression systems may be used for production of larger antibody molecules, including complete antibody molecules. Suitable mammalian host cells include CHO, HEK293T, PER.C6, NS0, myeloma or hybridoma cells.

The present invention also provides a process for the production of an antibody molecule according to the present invention comprising culturing a host cell comprising a vector of the present invention under conditions suitable for leading to expression of protein from DNA encoding the antibody molecule of the present invention, and isolating the antibody molecule.

The antibody molecule may comprise only a heavy or light chain polypeptide, in which case only a heavy chain or light chain polypeptide coding sequence needs to be used to transfect the host cells. For production of products comprising both heavy and light chains, the cell line may be transfected with two vectors, a first vector encoding a light chain polypeptide and a second vector encoding a heavy chain polypeptide. Alternatively, a single vector may be used, the vector including sequences encoding light chain and heavy chain polypeptides.

Alternatively, antibodies according to the invention may be produced by i) expressing a nucleic acid sequence according to the invention in a cell, and ii) isolating the expressed antibody product. Additionally, the method may include iii) purifying the antibody.

Screening and Isolation of B Cells

Transformed B cells may be screened for those producing antibodies of the desired antigen specificity, and individual B cell clones may then be produced from the positive cells.

The screening step may be carried out by ELISA, by staining of tissues or cells (including transfected cells), a neutralisation assay or one of a number of other methods known in the art for identifying desired antigen specificity. The assay may select on the basis of simple antigen recognition, or may select on the additional basis of a desired function e.g. to select neutralizing antibodies rather than just antigen-binding antibodies, to select antibodies that can change characteristics of targeted cells, such as their signalling cascades, their shape, their growth rate, their capability of influencing other cells, their response to the influence by other cells or by other reagents or by a change in conditions, their differentiation status, etc.

The cloning step for separating individual clones from the mixture of positive cells may be carried out using limiting dilution, micromanipulation, single cell deposition by cell sorting or another method known in the art.

The immortalised B cell clones of the invention can be used in various ways e.g. as a source of monoclonal antibodies, as a source of nucleic acid (DNA or mRNA) encoding a monoclonal antibody of interest, for research, etc.

The invention provides a composition comprising immortalised B memory cells, wherein the cells produce antibodies with high neutralizing potency specific for hCMV, and wherein the antibodies are produced at ≥5 pg per cell per day. The invention also provides a composition comprising clones of an immortalised B memory cell, wherein the clones produce a monoclonal antibody with a high affinity specific for hCMV, and wherein the antibody is produced at ≥5 pg per cell per day. Preferably said clones produce a monoclonal antibody with a high potency in neutralizing hCMV infection.

Exemplary immortalised B cell clone according to the invention include, but are not limited to, 15D8, 4N10, 10F7, 10P3, 4I22, 8L13, 2C12, 8C15, 9I6, 7B13, 8J16, 8I21, 7I13, 7H3, 6B4, 5F1, 10C6, 4H9, 11B12, 13H11, 3G16, 2B11 and 6L3.

Epitopes

As mentioned above, the antibodies of the invention can be used to map the epitopes to which they bind. The inventors have discovered that the several antibodies neutralizing hCMV infection of endothelial cells, epithelial cells, retinal cells and dendritic cells, are directed towards epitopes in the hCMV UL128 protein, epitopes formed by the hCMV proteins UL130 and UL131A, epitopes formed by the hCMV proteins UL128, UL130 and UL131A, epitopes formed by the hCMV proteins gH, gL, UL128 and UL130, gB, gH, or epitopes formed by the hCMV proteins gM and gN. The epitopes to which the antibodies of the invention bind may be linear (continuous) or conformational (discontinuous) and formed by a single hCMV protein or by the combination of 2, 3 or more hCMV proteins.

The epitopes recognised by the antibodies of the present invention may have a number of uses. The epitope and mimotopes thereof in purified or synthetic form can be used to raise immune responses (i.e. as a vaccine, or for the production of antibodies for other uses) or for screening patient serum for antibodies that immunoreact with the epitope or mimotopes thereof. In one embodiment such an epitope or mimotope, or antigen comprising such an epitope or mimotope may be used as a vaccine for raising an immune response. The antibodies and antibody fragments of the invention can also be used in a method of monitoring the quality of vaccines. In particular the antibodies can be used to check that the antigen in a vaccine contains the specific immunogenic epitope in the correct conformation.

The epitope may also be useful in screening for ligands that bind to said epitope. Such ligands, include but are not limited to antibodies; including those from camels, sharks and other species, fragments of antibodies, peptides, phage display technology products, aptamers, adnectins or fragments of other viral or cellular proteins, may block the epitope and so prevent infection. Such ligands are encompassed within the scope of the invention.

Recombinant Expression

The immortalised B memory cells of the invention may also be used as a source of nucleic acid for the cloning of antibody genes for subsequent recombinant expression. Expression from recombinant sources is more common for pharmaceutical purposes than expression from B cells or hybridomas e.g. for reasons of stability, reproducibility, culture ease, etc.

Thus the invention provides a method for preparing a recombinant cell, comprising the steps of: (i) obtaining one or more nucleic acids (e.g. heavy and/or light chain genes) from the B cell clone that encodes the antibody of interest; and (ii) inserting the nucleic acid into an expression host in order to permit expression of the antibody of interest in that host.

Similarly, the invention provides a method for preparing a recombinant cell, comprising the steps of: (i) sequencing nucleic acid(s) from the B cell clone that encodes the antibody of interest; and (ii) using the sequence information from step (i) to prepare nucleic acid(s) for insertion into an expression host in order to permit expression of the antibody of interest in that host. The nucleic acid may, but need not, be manipulated between steps (i) and (ii) to introduce restriction sites, to change codon usage, and/or to optimise transcription and/or translation regulatory sequences.

The invention also provides a method of preparing a recombinant cell, comprising the step of transforming a host cell with one or more nucleic acids that encode a monoclonal antibody of interest, wherein the nucleic acids are nucleic acids that were derived from an immortalised B cell clone of the invention. Thus the procedures for first preparing the nucleic acid(s) and then using it to transform a host cell can be performed at different times by different people in different places (e.g. in different countries).

These recombinant cells of the invention can then be used for expression and culture purposes. They are particularly useful for expression of antibodies for large-scale pharmaceutical production. They can also be used as the active ingredient of a pharmaceutical composition. Any suitable culture techniques can be used, including but not limited to static culture, roller bottle culture, ascites fluid, hollow-fiber type bioreactor cartridge, modular minifermenter, stirred tank, microcarrier culture, ceramic core perfusion, etc.

Methods for obtaining and sequencing immunoglobulin genes from B cells are well known in the art (e.g. see reference 37).

The expression host is preferably a eukaryotic cell, including yeast and animal cells, particularly mammalian cells (e.g. CHO cells, NS0 cells, human cells such as PER.C6 [Crucell; reference 38] or HKB-11 [Bayer; references 39 & 40] cells, myeloma cells [41 & 42], etc.), as well as plant cells. Preferred expression hosts can glycosylate the antibody of the invention, particularly with carbohydrate structures that are not themselves immunogenic in humans. In one embodiment the expression host may be able to grow in serum-free media. In a further embodiment the expression host may be able to grow in culture without the presence of animal-derived products.

The expression host may be cultured to give a cell line.

The invention provides a method for preparing one or more nucleic acid molecules (e.g. heavy and light chain genes) that encode an antibody of interest, comprising the steps of: (i) preparing an immortalised B cell clone according to the invention; (ii) obtaining from the B cell clone nucleic acid that encodes the antibody of interest. The invention also provides a method for obtaining a nucleic acid sequence that encodes an antibody of interest, comprising the steps of: (i) preparing an immortalised B cell clone according to the invention; (ii) sequencing nucleic acid from the B cell clone that encodes the antibody of interest.

The invention also provides a method of preparing nucleic acid molecule(s) that encodes an antibody of interest, comprising the step of obtaining the nucleic acid from a B cell clone that was obtained from a transformed B cell of the invention. Thus the procedures for first obtaining the B cell clone and then preparing nucleic acid(s) from it can be performed at very different times by different people in different places (e.g. in different countries).

The invention provides a method for preparing an antibody (e.g. for pharmaceutical use), comprising the steps of: (i) obtaining and/or sequencing one or more nucleic acids (e.g. heavy and light chain genes) from the selected B cell clone expressing the antibody of interest; (ii) inserting the nucleic acid(s) into or using the nucleic acid(s) to prepare an expression host that can express the antibody of interest; (iii) culturing or sub-culturing the expression host under conditions where the antibody of interest is expressed; and, optionally, (iv) purifying the antibody of the interest.

The invention also provides a method of preparing an antibody comprising the steps of: culturing or sub-culturing an expression host cell population under conditions where the antibody of interest is expressed and, optionally, purifying the antibody of the interest, wherein said expression host cell population has been prepared by (i) providing nucleic acid(s) encoding a selected B cell the antibody of interest that is produced by a population of B memory lymphocytes prepared as described above, (ii) inserting the nucleic acid(s) into an expression host that can express the antibody of interest, and (iii) culturing or sub-culturing expression hosts comprising said inserted nucleic acids to produce said expression host cell population. Thus the procedures for first preparing the recombinant expression host and then culturing it to express antibody can be performed at very different times by different people in different places (e.g. in different countries).

Further, cell lines expressing exemplary antibodies of the invention, 4N10, 2C12, 8C15, 8I21, 6B4, 10C6, 4H9, 11B12, 3G16, and 6L3 were deposited with the Advanced Biotechnology Center (ABC), Largo Rossana Benzi 10, 16132 Genoa (Italy), under the terms of the Budapest Treaty, on Jul. 9, 2008, (under Accession Numbers PD 08009, PD 08007, PD 08006, PD 08005, PD 08004, PD 08014, PD 08013, PD 08011, PD 08012, and PD 08010, respectively) and an immortalized B cell line expressing 7H3 was deposited on Jul. 16, 2008 under Accession Number PD 08017. An antibody, or an antigen binding fragment thereof, expressed from the above cell lines as well as antibodies, and antigen binding fragments thereof, with the same amino acid sequence as those expressed from the above cell lines are also considered to be within the scope of the invention.

These deposits are provided for the convenience of those skilled in the art and are neither an admission that such deposits are required to practice the invention nor that equivalent embodiments are not within the skill of the art in view of the present disclosure. The public availability of these deposits is not a grant of a license to make, use or sell the deposited materials under this or any other patents. The nucleic acid sequences of the deposited materials are incorporated in the present disclosure by reference and are controlling if in conflict with any sequence described herein.

Pharmaceutical Compositions

The invention provides a pharmaceutical composition containing the antibodies and/or antibody fragments of the invention and/or nucleic acid encoding such antibodies and/or immortalised B cells that express such antibodies and/or the epitopes recognised by the antibodies of the invention. A pharmaceutical composition may also contain a pharmaceutically acceptable carrier to allow administration. The carrier should not itself induce the production of antibodies harmful to the individual receiving the composition and should not be toxic. Suitable carriers may be large, slowly metabolised macromolecules such as proteins, polypeptides, liposomes, polysaccharides, polylactic acids, polyglycolic acids, polymeric amino acids, amino acid copolymers and inactive virus particles.

Pharmaceutically acceptable salts can be used, for example mineral acid salts, such as hydrochlorides, hydrobromides, phosphates and sulphates, or salts of organic acids, such as acetates, propionates, malonates and benzoates.

Pharmaceutically acceptable carriers in therapeutic compositions may additionally contain liquids such as water, saline, glycerol and ethanol. Additionally, auxiliary substances, such as wetting or emulsifying agents or pH buffering substances, may be present in such compositions. Such carriers enable the pharmaceutical compositions to be formulated as tablets, pills, dragees, capsules, liquids, gels, syrups, slurries and suspensions, for ingestion by the patient.

Within the scope of the invention, forms of administration may include those forms suitable for parenteral administration, e.g. by injection or infusion, for example by bolus injection or continuous infusion. Where the product is for injection or infusion, it may take the form of a suspension, solution or emulsion in an oily or aqueous vehicle and it may contain formulatory agents, such as suspending, preservative, stabilising and/or dispersing agents. Alternatively, the antibody molecule may be in dry form, for reconstitution before use with an appropriate sterile liquid.

Once formulated, the compositions of the invention can be administered directly to the subject. In one embodiment the compositions are adapted for administration to human subjects.

The pharmaceutical compositions of this invention may be administered by any number of routes including, but not limited to, oral, intravenous, intramuscular, intra-arterial, intramedullary, intraperitoneal, intrathecal, intraventricular, transdermal, transcutaneous, topical, subcutaneous, intranasal, enteral, sublingual, intravaginal or rectal routes. Hyposprays may also be used to administer the pharmaceutical compositions of the invention. Typically, the therapeutic compositions may be prepared as injectables, either as liquid solutions or suspensions. Solid forms suitable for solution in, or suspension in, liquid vehicles prior to injection may also be prepared.

Direct delivery of the compositions will generally be accomplished by injection, subcutaneously, intraperitoneally, intravenously or intramuscularly, or delivered to the interstitial space of a tissue. The compositions can also be administered into a lesion. Dosage treatment may be a single dose schedule or a multiple dose schedule. Known antibody-based pharmaceuticals provide guidance relating to frequency of administration e.g. whether a pharmaceutical should be delivered daily, weekly, monthly, etc. Frequency and dosage may also depend on the severity of symptoms.

Compositions of the invention may be prepared in various forms. For example, the compositions may be prepared as injectables, either as liquid solutions or suspensions. Solid forms suitable for solution in, or suspension in, liquid vehicles prior to injection can also be prepared (e.g. a lyophilised composition, like Synagis™ and Herceptin™, for reconstitution with sterile water containing a preservative). The composition may be prepared for topical administration e.g. as an ointment, cream or powder. The composition may be prepared for oral administration e.g. as a tablet or capsule, as a spray, or as a syrup (optionally flavoured). The composition may be prepared for pulmonary administration e.g. as an inhaler, using a fine powder or a spray. The composition may be prepared as a suppository or pessary. The composition may be prepared for nasal, aural or ocular administration e.g. as drops. The composition may be in kit form, designed such that a combined composition is reconstituted just prior to administration to a patient. For example, a lyophilised antibody can be provided in kit form with sterile water or a sterile buffer.

It will be appreciated that the active ingredient in the composition will be an antibody molecule, an antibody fragment or variants and derivatives thereof. As such, it will be susceptible to degradation in the gastrointestinal tract. Thus, if the composition is to be administered by a route using the gastrointestinal tract, the composition will need to contain agents which protect the antibody from degradation but which release the antibody once it has been absorbed from the gastrointestinal tract.

A thorough discussion of pharmaceutically acceptable carriers is available in Gennaro (2000) *Remington: The Science and Practice of Pharmacy*, 20th edition, ISBN: 0683306472.

Pharmaceutical compositions of the invention generally have a pH between 5.5 and 8.5, in some embodiments this may be between 6 and 8, and in further embodiments about 7. The pH may be maintained by the use of a buffer. The composition may be sterile and/or pyrogen free. The composition may be isotonic with respect to humans. In one embodiment pharmaceutical compositions of the invention are supplied in hermetically-sealed containers.

Pharmaceutical compositions will include an effective amount of one or more antibodies of the invention and/or one or more immortalised B cells of the invention and/or a polypeptide comprising an epitope that binds an antibody of the invention i.e. an amount that is sufficient to treat, ameliorate, or prevent a desired disease or condition, or to exhibit a detectable therapeutic effect. Therapeutic effects also include reduction in physical symptoms. The precise effective amount for any particular subject will depend upon their size and health, the nature and extent of the condition, and the therapeutics or combination of therapeutics selected for administration. The effective amount for a given situation is determined by routine experimentation and is within the judgment of a clinician. For purposes of the present invention, an effective dose will generally be from about 0.01 mg/kg to about 50 mg/kg, or about 0.05 mg/kg to about 10 mg/kg of the compositions of the present invention in the individual to which it is administered. Known antibody-based pharmaceuticals provide guidance in this respect e.g. Herceptin™ is administered by intravenous infusion of a 21 mg/ml solution, with an initial loading dose of 4 mg/kg body weight and a weekly maintenance dose of 2 mg/kg body weight; Rituxan™ is administered weekly at 375 mg/m²; etc.

In one embodiment compositions can include more than one (e.g. 2, 3, 4, 5, etc.) antibody of the invention to provide an additive or synergistic therapeutic effect. In a further embodiment the composition may comprise one or more (e.g. 2, 3, 4, 5, etc.) antibody of the invention and one or more (e.g. 2, 3, 4, 5, etc.) additional antibodies that neutralize hCMV infection.

For example, one antibody may bind to an epitope in the hCMV UL128 protein, an epitope formed by the hCMV proteins UL130 and UL131A, an epitope formed by the hCMV proteins UL128, UL130 and UL131A, an epitope formed by the hCMV proteins gH, gL, UL128 and UL130, an epitope in the hCMV gB protein, an epitope in the hCMV gH protein, or an epitope formed by the hCMV proteins gM and gN, while another may bind to a different epitope in the hCMV UL128 protein, an epitope formed by UL130 and UL131A, an epitope formed by UL128, UL130 and UL131A, an epitope formed by gH, gL, UL128 and UL130, gB, gH, gL, gM, gN, gO, or an epitope formed by gM and gN. Without being bound to any theory, one antibody may be targeted to the mechanism that mediates infection of fibroblasts, while the other antibody may be targeted to the mechanism that mediates infection of endothelial cells. For optimal clinical effect it may well be advantageous to address both mechanisms of hCMV infection and maintenance.

In one embodiment, the invention provides a pharmaceutical composition comprising two or more antibodies, wherein the first antibody is specific for a first UL128 epitope, and the second antibody is specific for a second UL128 epitope, a combination of UL130 and UL131A, a combination of UL128, UL130 and UL131A, a combination of gH, gL, UL128 and UL130, gB, gH, gL, gM, gN, gO, or a combination of gM and gN.

In another embodiment, the invention provides a pharmaceutical composition comprising two or more antibodies, wherein the first antibody is specific for a first epitope on a combination of UL130 and 131A, and the second antibody is specific for UL128, a second epitope on a combination of UL130 and 131A, a combination of UL128, UL130 and UL131A, a combination of gH, gL, UL128 and UL130, gB, gH, gL, gM, gN, gO, or a combination of gM and gN.

In yet another embodiment, the invention provides a pharmaceutical composition comprising two or more antibodies, wherein the first antibody is specific for a first epitope on a combination of UL128, UL130 and 131A, and the second antibody is specific for UL128, a combination of UL130 and UL131A, a second epitope on a combination of UL128, UL130 and 131A, a combination of gH, gL, UL128 and UL130, gB, gH, gL, gM, gN, gO, or a combination of gM and gN.

In still another embodiment, the invention provides a pharmaceutical composition comprising two or more antibodies, wherein the first antibody is specific for a first epitope on a combination of gH, gL, UL128, UL130 and UL131A, and the second antibody is specific for UL128, a combination of UL130 and UL131A, a combination of UL128, UL130 and 131A, a second epitope on a combination of gH, gL, UL128 and UL130, gB, gH, gL, gM, gN, gO, or a combination of gM and gN.

In a further embodiment, the invention provides a pharmaceutical composition comprising two or more antibodies, wherein the first antibody is specific for a first gB epitope, and the second antibody is specific for UL128, a combination of UL130 and UL131A, a combination of UL128, UL130 and UL131A, a combination of gH, gL, UL128 and UL130, a second gB epitope, gH, gL, gM, gN, gO, or a combination of gM and gN.

In another embodiment, the invention provides a pharmaceutical composition comprising two or more antibodies, wherein the first antibody is specific for a first gH epitope, and the second antibody is specific for UL128, a combination of UL130 and UL131A, a combination of UL128, UL130 and UL131A, a combination of gH, gL, UL128 and UL130, gB, a second gH epitope, gL, gM, gN, gO, or a combination of gM and gN.

In yet another embodiment, the invention provides a pharmaceutical composition comprising two or more antibodies, wherein the first antibody is specific for a first epitope on a combination of gM and gN, and the second antibody is specific for UL128, a combination of UL130 and UL131A, a combination of UL128, UL130 and UL131A, a combination of gH, gL, UL128 and UL130, gB, gH, gL, gM, gN, gO, or a second epitope on a combination of gM and gN.

Exemplary antibodies of the invention for use in a pharmaceutical composition that bind to an epitope in the hCMV UL128 protein include, but are not limited to, 15D8. Exemplary antibodies of the invention for use in a pharmaceutical composition that bind an epitope formed by the hCMV proteins UL130 and UL131A include, but are not limited to, 4N10, 10F7, 10P3, 4I22, 8L13, 1F11, 2F4 and 5A2 (see U.S. application Ser. No. 11/969,104, filed Jan. 3, 2008). Exemplary antibodies of the invention for use in a pharmaceutical composition that bind an epitope formed by the hCMV proteins UL128, UL130 and UL131A include, but are not limited to, 2C12, 7B13, 7I13, 8C15, 8J16, 9I6, and 6G4 (see U.S. application Ser. No. 12/174,568, filed Jul. 16, 2008). Exemplary antibodies of the invention for use in a pharmaceutical composition that bind an epitope formed by the hCMV proteins gH, gL, UL128 and UL130 include, but are not limited to, 8I21. Exemplary antibodies of the invention for use in a pharmaceutical composition that bind to an epitope in the hCMV gB protein include, but are not limited to, 7H3, 10C6, 5F1, 6B4, 4H9 and 2B11. Exemplary antibodies of the invention for use in a pharmaceutical composition that bind to an epitope in the hCMV gH protein include, but are not limited to, 11B12, 13H11, and 3G16. Exemplary antibodies of the invention for use in a pharmaceutical composition that bind an epitope formed by the hCMV proteins gM and gN include, but are not limited to, 6L3. The invention further provides a pharmaceutical composition comprising two or more antibodies, wherein the first antibody is an antibody or antibody fragment of the invention and the second antibody is an antibody now known in the art, or later discovered, that neutralises hCMV infection. Examples of such antibodies include, but are not limited to MSL-109, 8F9 or 3E3.

In one embodiment, the invention provides a pharmaceutical composition comprising the antibody 15D8 or an antigen binding fragment thereof, and a pharmaceutically acceptable carrier. In another embodiment, the invention provides a pharmaceutical composition comprising the antibody 15D8 variant for an antigen binding fragment thereof, and a pharmaceutically acceptable carrier. In another embodiment, the invention provides a pharmaceutical composition comprising the antibody 15D8 variant 2 or an antigen binding fragment thereof, and a pharmaceutically acceptable carrier. In another embodiment, the invention provides a pharmaceutical composition comprising the antibody 8I21 or an antigen binding fragment thereof, and a pharmaceutically acceptable carrier.

In yet another embodiment, the invention provides a pharmaceutical composition comprising the antibody 2C12 or an antigen binding fragment thereof, and a pharmaceutically acceptable carrier. In another embodiment, the invention provides a pharmaceutical composition comprising the antibody 8C15 or an antigen binding fragment thereof, and a pharmaceutically acceptable carrier. In another embodiment, the invention provides a pharmaceutical composition comprising the antibody 9I6 or an antigen binding fragment thereof, and a pharmaceutically acceptable carrier. In another embodiment, the invention provides a pharmaceutical composition comprising the antibody 7B13 or an antigen binding fragment thereof, and a pharmaceutically acceptable carrier. In another embodiment, the invention provides a pharmaceutical composition comprising the antibody 8J16 or an antigen binding fragment thereof, and a pharmaceutically acceptable carrier. In another embodiment, the invention provides a pharmaceutical composition comprising the antibody 7I13 or an antigen binding fragment thereof, and a pharmaceutically acceptable carrier.

In yet another embodiment, the invention provides a pharmaceutical composition comprising the antibody 4N10 or an antigen binding fragment thereof, and a pharmaceutically acceptable carrier. In another embodiment, the invention provides a pharmaceutical composition comprising the antibody 10F7 or an antigen binding fragment thereof, and a pharmaceutically acceptable carrier. In another embodiment, the invention provides a pharmaceutical composition comprising the antibody 10P3 or an antigen binding fragment thereof, and a pharmaceutically acceptable carrier. In another embodiment, the invention provides a pharmaceutical composition comprising the antibody 4I22 or an antigen binding fragment thereof, and a pharmaceutically acceptable carrier. In another embodiment, the invention provides a pharmaceutical composition comprising the antibody 8L13 or an antigen binding fragment thereof, and a pharmaceutically acceptable carrier.

In yet another embodiment, the invention provides a pharmaceutical composition comprising the antibody 7H3 or an antigen binding fragment thereof, and a pharmaceutically acceptable carrier. In another embodiment, the invention provides a pharmaceutical composition comprising the antibody 7H3 variant 1 or an antigen binding fragment thereof, and a pharmaceutically acceptable carrier. In another embodiment, the invention provides a pharmaceutical composition comprising the antibody 10C6 or an antigen binding fragment thereof, and a pharmaceutically acceptable carrier. In another embodiment, the invention provides a pharmaceutical composition comprising the antibody 5F1 or an antigen binding fragment thereof, and a pharmaceutically acceptable carrier. In another embodiment, the invention provides a pharmaceutical composition comprising the antibody 6B4 or an antigen binding fragment thereof, and a pharmaceutically acceptable carrier. In another embodiment, the invention provides a pharmaceutical composition comprising the antibody 4H9 or an antigen binding fragment thereof, and a pharmaceutically acceptable carrier. In another embodiment, the invention provides a pharmaceutical composition comprising the antibody 4H9 variant 1 or an antigen binding fragment thereof, and a pharmaceutically acceptable carrier. In another embodiment, the invention provides a pharmaceutical composition comprising the antibody 2B11 or an antigen binding fragment thereof, and a pharmaceutically acceptable carrier.

In yet another embodiment, the invention provides a pharmaceutical composition comprising the antibody 13H11 or an antigen binding fragment thereof, and a pharmaceutically acceptable carrier. In another embodiment, the invention provides a pharmaceutical composition comprising the antibody 11B12 or an antigen binding fragment thereof, and a pharmaceutically acceptable carrier. In another embodiment, the invention provides a pharmaceutical composition comprising the antibody 3G16 or an antigen binding fragment thereof, and a pharmaceutically acceptable carrier. In another embodiment, the invention provides a pharmaceutical composition comprising the antibody 6L3 or an antigen binding fragment thereof, and a pharmaceutically acceptable carrier.

In one embodiment, the pharmaceutical compositions of the invention may comprise the above antibodies or antigen binding fragments thereof, as the sole active ingredient. In another embodiment, the pharmaceutical composition may comprise 2 or more, e.g., 2, 3, 4, 5, 6, 7, 8, or more of the above antibodies or antigen binding fragment thereof. As discussed herein, the pharmaceutical compositions of the invention may also comprise one or more antibodies, or antigen binding fragment thereof, and a second antibody, or antigen binding fragment thereof, that neutralises hCMV infection.

Antibodies of the invention may be administered (either combined or separately) with other therapeutics e.g. with chemotherapeutic compounds, with radiotherapy, etc. Preferred therapeutic compounds include anti-viral compounds such as ganciclovir, foscarnet and cidofovir. Such combination therapy provides an additive or synergistic improvement in therapeutic efficacy relative to the individual therapeutic agents when administered alone. The term "synergy" is used to describe a combined effect of two or more active agents that is greater than the sum of the individual effects of each respective active agent. Thus, where the combined effect of two or more agents results in "synergistic inhibition" of an activity or process, it is intended that the inhibition of the activity or process is greater than the sum of the inhibitory effects of each respective active agent. The term "synergistic therapeutic effect" refers to a therapeutic effect observed with a combination of two or more therapies wherein the therapeutic effect (as measured by any of a number of parameters) is greater than the sum of the individual therapeutic effects observed with the respective individual therapies.

Antibodies may be administered to those patients who have previously shown no response to treatment for hCMV infection, i.e. have been shown to be refractive to anti-hCMV treatment. Such treatment may include previous treatment with an anti-viral agent. This may be due to, for example, infection with an anti-viral resistant strain of hCMV.

In compositions of the invention that include antibodies of the invention, the antibodies may make up at least 50% by weight (e.g. 60%, 70%, 75%, 80%, 85%, 90%, 95%, 97%, 98%, 99% or more) of the total protein in the composition. The antibodies are thus in purified form.

The invention provides a method of preparing a pharmaceutical, comprising the steps of: (i) preparing an antibody of the invention; and (ii) admixing the purified antibody with one or more pharmaceutically-acceptable carriers.

The invention also provides a method of preparing a pharmaceutical, comprising the step of admixing an antibody with one or more pharmaceutically-acceptable carriers, wherein the antibody is a monoclonal antibody that was obtained from a transformed B cell of the invention. Thus the procedures for first obtaining the monoclonal antibody and then preparing the pharmaceutical can be performed at very different times by different people in different places (e.g. in different countries).

As an alternative to delivering antibodies or B cells for therapeutic purposes, it is possible to deliver nucleic acid (typically DNA) that encodes the monoclonal antibody (or active fragment thereof) of interest to a subject, such that the nucleic acid can be expressed in the subject in situ to provide a desired therapeutic effect. Suitable gene therapy and nucleic acid delivery vectors are known in the art.

Compositions of the invention may be immunogenic compositions, and in some embodiments may be vaccine compositions comprising an antigen comprising an epitope in the hCMV UL128 protein, formed by the hCMV proteins UL130 and 131A, formed by the hCMV proteins UL128, UL130 and UL131A, formed by the hCMV proteins gH, gL, UL128 and UL130, in the hCMV gB protein, in the hCMV gH protein, or formed by the hCMV proteins gM and gN. Alternative compositions may comprise (i) an antigen comprising an epitope formed by a combination of hCMV proteins UL128, UL130 and UL131A, and (ii) an antigen comprising an epitope found on gB, gH, gL, gM, gN, gO, UL128, UL130 or UL131A, or a combination thereof. Vaccines according to the invention may either be prophylactic (i.e. to prevent infection) or therapeutic (i.e. to treat infection).

Compositions may include an antimicrobial, particularly if packaged in a multiple dose format. They may comprise a detergent e.g., a Tween (polysorbate), such as Tween 80. Detergents are generally present at low levels e.g. <0.01%. Compositions may also include sodium salts (e.g. sodium chloride) to give tonicity. A concentration of 10±2 mg/ml NaCl is typical.

Compositions may comprise a sugar alcohol (e.g. mannitol) or a disaccharide (e.g. sucrose or trehalose) e.g. at around 15-30 mg/ml (e.g. 25 mg/ml), particularly if they are to be lyophilised or if they include material which has been reconstituted from lyophilised material. The pH of a composition for lyophilisation may be adjusted to around 6.1 prior to lyophilisation.

The compositions of the invention may also comprise one or more immunoregulatory agents. In one embodiment, one or more of the immunoregulatory agents include(s) an adjuvant.

The epitope compositions of the invention may elicit both a cell mediated immune response as well as a humoral immune response in order to effectively address a hCMV infection. This immune response may induce long lasting (e.g. neutralizing) antibodies and a cell mediated immunity that can quickly respond upon exposure to hCMV.

Medical Treatments and Uses

The antibodies, antibody fragments of the invention or derivatives and variants thereof may be used for the treatment of hCMV infection, for the prevention of hCMV infection or for the diagnosis of hCMV infection.

Methods of diagnosis may include contacting an antibody or an antibody fragment with a sample. Such samples may be tissue samples taken from, for example, salivary glands, lung, liver, pancreas, kidney, ear, eye, placenta, alimentary tract, heart, ovaries, pituitary, adrenals, thyroid, brain or skin. The methods of diagnosis may also include the detection of an antigen/antibody complex.

The invention therefore provides (i) an antibody, an antibody fragment, or variants and derivatives thereof according to the invention, (ii) an immortalised B cell clone according to the invention, (iii) an epitope capable of binding an antibody of the invention or (iv) a ligand, preferably an antibody, capable of binding an epitope that binds an antibody of the invention for use in therapy.

Also provided is a method of treating a patient comprising administering to that patient (i) an antibody, an antibody fragment, or variants and derivatives thereof according to the invention, or, a ligand, preferably an antibody, capable of binding an epitope that binds an antibody of the invention.

The invention also provides the use of (i) an antibody, an antibody fragment, or variants and derivatives thereof according to the invention, (ii) an immortalised B cell clone according to the invention, (iii) an epitope capable of binding an antibody of the invention, or (iv) a ligand, preferably an antibody, that binds to an epitope capable of binding an antibody of the invention, in the manufacture of a medicament for the prevention or treatment of hCMV infection.

The invention provides a composition for use as a medicament for the prevention or treatment of an hCMV infection. It also provides the use of an antibody and/or a protein comprising an epitope to which such an antibody binds in the manufacture of a medicament for treatment of a patient and/or diagnosis in a patient. It also provides a method for treating a subject in need of treatment, comprising the step of administering a composition of the invention to the subject. In some embodiments the subject may be a human. One way of checking efficacy of therapeutic treatment involves monitoring disease symptoms after administration of the composition of the invention. Treatment can be a single dose schedule or a multiple dose schedule.

In one embodiment, an antibody of the invention, an antigen-binding fragment thereof, an epitope or a composition of the invention is administered to a subject in need of such prophylactic or therapeutic treatment. Such a subject includes, but is not limited to, one who is particularly at risk of, or susceptible to, hCMV infection. Exemplary subjects include, but are not limited to, immunocompromised subjects or hCMV-seronegative or hCMV recently infected pregnant women. Exemplary immunocompromised subjects include, but are not limited to, those afflicted with HIV or those undergoing immunosuppressive therapy.

Antibodies of the invention and antigen-biding fragments thereof can also be used in passive immunisation. Further, as described in the present invention, they may also be used in a kit for the diagnosis of hCMV infection.

Epitopes capable of binding an antibody of the invention, e.g., the monoclonal antibodies 15D8, 4N10, 10F7, 10P3, 4I22, 8L13, 2C12, 8C15, 9I6, 7B13, 8J16, 8I21, 7I13, 7H3, 6B4, 5F1, 10C6, 4H9, 2B11, 11B12, 13H11, 3G16, and 6L3, may be used in a kit for monitoring the efficacy of vaccination procedures by detecting the presence of protective anti-hCMV antibodies.

Antibodies, antibody fragment, or variants and derivatives thereof, as described in the present invention may also be used in a kit for monitoring vaccine manufacture with the desired immunogenicity.

The invention also provides a method of preparing a pharmaceutical, comprising the step of admixing a monoclonal antibody with one or more pharmaceutically-acceptable carriers, wherein the monoclonal antibody is a monoclonal antibody that was obtained from an expression host of the invention. Thus the procedures for first obtaining the monoclonal antibody (e.g. expressing it and/or purifying it) and then admixing it with the pharmaceutical carrier(s) can be performed at very different times by different people in different places (e.g. in different countries).

Starting with a transformed B cell of the invention, various steps of culturing, sub-culturing, cloning, sub-cloning, sequencing, nucleic acid preparation etc. can be performed in order to perpetuate the antibody expressed by the transformed B cell, with optional optimisation at each step. In a preferred embodiment, the above methods further comprise techniques of optimisation (e.g. affinity maturation or optimisation) applied to the nucleic acids encoding the antibody. The invention encompasses all cells, nucleic acids, vectors, sequences, antibodies etc. used and prepared during such steps.

In all these methods, the nucleic acid used in the expression host may be manipulated to insert, delete or amend certain nucleic acid sequences. Changes from such manipulation include, but are not limited to, changes to introduce restriction sites, to amend codon usage, to add or optimise transcription and/or translation regulatory sequences, etc. It is also possible to change the nucleic acid to alter the encoded amino acids. For example, it may be useful to introduce one or more (e.g. 1, 2, 3, 4, 5, 6, 7, 8, 9, 10, etc.) amino acid substitutions, deletions and/or insertions into the antibody's amino acid sequence. Such point mutations can modify effector functions, antigen-binding affinity, post-translational modifications, immunogenicity, etc., can introduce amino acids for the attachment of covalent groups (e.g. labels) or can introduce tags (e.g. for purification purposes). Mutations can be introduced in specific sites or can be introduced at random, followed by selection (e.g. molecular evolution). For instance, one or more nucleic acids encoding any of the CDR regions, heavy chain variable regions or light chain variable regions of antibodies of the invention can be randomly or directionally mutated to introduce different properties in the encoded amino acids. Such changes can be the result of an iterative process wherein initial changes are retained and new changes at other nucleotide positions are introduced. Moreover, changes achieved in independent steps may be combined. Different properties introduced into the encoded amino acids may include, but are not limited to, enhanced affinity.

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x means, for example, x±10%.

The term "disease" as used herein is intended to be generally synonymous, and is used interchangeably with, the terms "disorder" and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

As used herein, reference to "treatment" of a patient is intended to include prevention and prophylaxis. The term "patient" means all mammals including humans. Examples of patients include humans, cows, dogs, cats, horses, goats, sheep, pigs, and rabbits. Generally, the patient is a human.

EXAMPLES

Exemplary embodiments of the present invention are provided in the following examples. The following examples are presented only by way of illustration and to assist one of ordinary skill in using the invention. The examples are not intended in any way to otherwise limit the scope of the invention.

Example 1: Cloning of B Cells and Screening for hCMV Neutralizing Activity

Donors with high hCMV neutralizing antibody titres in the serum were identified. Memory B cells were isolated and immortalised using EBV and CpG as described in reference 36. Briefly, memory B cells were isolated by negative selection using CD22 beads, followed by removal of IgM$^+$, IgD$^+$, IgA$^+$ B cells using specific antibodies and cell sorting. The sorted cells (IgG$^+$) were immortalized with EBV in the presence of CpG 2006 and irradiated allogeneic mononuclear cells. Replicate cultures each containing 50 memory B cells were set up in twenty 96 well U bottom plates. After two weeks the culture supernatants were collected and tested for their capacity to neutralize hCMV infection of either fibroblasts or epithelial cells in separate assays. B cell clones were isolated from positive polyclonal cultures as described in reference 36. IgG concentrations in the supernatant of selected clones were determined using an IgG-specific ELISA.

For the viral neutralization assay a titrated amount of a clinical hCMV isolate was mixed with an equal volume of culture supernatant or with dilutions of human sera containing neutralizing antibodies. After 1 hour incubation at room temperature the mixture was added to confluent monolayers of either endothelial cells (e.g. HUVEC cells or HMEC-1 cells), epithelial cells (e.g. ARPE retinal cells), fibroblasts (e.g. MRC-9 or mesenchymal stromal cells) or myeloid cells (e.g. monocyte-derived dendritic cells) in 96 well flat-bottom plates and incubated at 37° C. for two days. The supernatant was discarded, the cells were fixed with cold methanol and stained with a mixture of mouse monoclonal antibodies to hCMV early antigens, followed by a fluorescein-labeled goat anti mouse Ig. The plates were analyzed using a fluorescence microscope. In the absence of neutralizing antibodies the infected cells were 100-1,000/field, while in the presence of saturating concentrations of neutralizing antibodies the infection was completely inhibited. The neutralizing titer is indicated as the concentration of antibody (µg/ml) that gives a 50% or 90% reduction of hCMV infection.

Table 5A shows the neutralization of a hCMV clinical isolate (VR1814) on both a fibroblastic cell line (MRC-9) and a human retinal epithelial cell line (ARPE). Some antibodies neutralized hCMV infection of epithelial cells (ARPE) but they did not neutralize infection of fibroblasts (MRC-9). This agrees with previous data that different proteins are responsible for tropism towards a particular cell type [7]. Most of these antibodies, which are specific for one or more proteins of the gH/gL/UL128/UL130/UL131A protein complex, neutralized hCMV infection of epithelial cells at very low concentrations (50% reduction of hCMV infection at concentrations ranging from 0.01 µg/ml and 0.001 µg/ml). Other antibodies, which are specific for the hCMV protein gB, gH or a combination of gM and gN, neutralized hCMV infection of fibroblasts and epithelial cells with comparable potency. These results show that some of the hCMV neutralizing antibodies are equally potent on both fibroblasts and epithelial cells, while others show differential activity on the two cell types.

Based on the analysis shown in Table 5A, antibodies were grouped into Group 1 (neutralizing hCMV infection of both fibroblasts and epithelial cells) and Group 2 (neutralizing hCMV infection of epithelial cells). Table 5B shows an independent experiment performed using purified antibodies. The results show that Group 2 antibodies neutralized infection of epithelial cells with IC90 values (i.e. the concentration of antibody required to give 90% reduction of viral infection) ranging from 0.007 µg/ml to 0.003 µg/ml while Group 1 antibodies neutralized infection of both fibroblasts and epithelial cells with IC90 values ranging from 0.1 µg/ml to 30 µg/ml. Group 2 antibodies also neutralized infection of endothelial cells (HUVEC) and myeloid cells (monocyte-derived dendritic cells) (data not shown). Group 1 antibodies also neutralized infection of endothelial cells (HUVEC), myeloid cells (monocyte-derived dendritic cells) and bone marrow mesenchymal stromal cells, as shown for some representative antibodies in Table 5C. Antibodies of the invention also neutralized infection of endothelial cells (HUVEC) by different hCMV clinical isolates: VR6952 (from urine), VR3480B1 (from blood, ganciclovir-resistant) and VR4760 (from blood, ganciclovir and foscarnet-resistant) (data not shown).

It is anticipated that antibodies that neutralize infection of different cell types may be combined to bring about an additive or synergistic neutralization effect when the different cell types are present during infection. As one example, a neutralizing antibody, such as 15D8 which is potent in neutralizing infection of epithelial cells but does not neutralize infection of fibroblasts might be combined with 3G16 which does have virus neutralizing activity on fibroblasts. As another example, a neutralizing antibody, such as 9I6 which is potent in neutralizing infection of epithelial cells but does not neutralize infection of fibroblasts, might be combined with 6B4 which does have virus neutralizing activity on fibroblasts.

TABLE 5A

| mAb | Donor | Specificity[2] | 50% Neutralization[1] MRC-9 | 50% Neutralization[1] ARPE |
|---|---|---|---|---|
| 15D8 | GRA | UL128 | − | ++++ |
| 4N10 | GIO | UL130/UL131A | + | ++++ |
| 10F7 | PAP | UL130/UL131A | + | +++ |
| 10P3 | PEL | UL130/UL131A | − | ++++ |
| 4I22 | PEL | UL130/UL131A | − | +++ |
| 8L13 | PEL | UL130/UL131A | − | +++ |
| 2C12 | PAP | UL128/UL130/UL131A | + | +++ |
| 7B13 | PAP | UL128/UL130/UL131A | − | ++++ |
| 7I13 | PAP | UL128/UL130/UL131A | − | +++ |
| 8C15 | PAP | UL128/UL130/UL131A | − | ++++ |
| 8J16 | PAP | UL128/UL130/UL131A | − | ++++ |
| 9I6 | PEL | UL128/UL130/UL131A | − | ++++ |
| 8I21 | PEL | gH/gL/UL128/UL130 | − | +++ |
| 11B12 | PAP | gH | + | + |
| 13H11 | GRA | gH | + | +++ |
| 3G16 | PEL | gH | + | + |
| 7H3 | PEL | gB | + | − |
| 10C6 | PEL | gB | + | + |
| 5F1 | PEL | gB | + | + |
| 6B4 | PEL | gB | + | + |
| 4H9 | PEL | gB | + | + |
| 6L3 | PEL | gM/gN | Not done | + |

[1]Values indicating the concentration of antibody required to give a 50% reduction of hCMV infection of fibroblasts (e.g. MRC-9) or epithelial cells (e.g. ARPE retinal cells). Concentration as follows: ++++ < 0.001 µg/ml; +++ < 0.01 µg/ml; ++ < 0.1 µg/ml; + ≤ 2 µg/ml; − Not neutralizing at the highest concentration tested (2 µg/ml).
[2]Specificity as defined in Table 6.

TABLE 5B

| Group | mAb | Donor | Specificity[2] | 90% Neutralization[1] MRC-9 | 90% Neutralization[1] ARPE |
|---|---|---|---|---|---|
| 2 | 15D8 | GRA | UL128 | nn[3] | 0.008 |
| 2 | 4N10 | GIO | UL130/UL131A | nn | 0.02 |
| 2 | 10F7 | PAP | UL130/UL131A | nn | 0.002 |
| 2 | 10P3 | PEL | UL130/UL131A | nn | 0.0025 |
| 2 | 4I22 | PEL | UL130/UL131A | nn | 0.0015 |
| 2 | 8L13 | PEL | UL130/UL131A | nn | 0.001 |
| 2 | 2C12 | PAP | UL128/UL130/UL131A | nn | 0.006 |
| 2 | 7B13 | PAP | UL128/UL130/UL131A | nn | 0.003 |
| 2 | 7I13 | PAP | UL128/UL130/UL131A | nn | 0.008 |
| 2 | 8C15 | PAP | UL128/UL130/UL131A | nn | 0.0025 |
| 2 | 8J16 | PAP | UL128/UL130/UL131A | nn | 0.0008 |
| 2 | 9I6 | PEL | UL128/UL130/UL131A | nn | 0.0007 |
| 2 | 8I21 | PEL | gH/gL/UL128/UL130 | nn | 0.03 |
| 1 | 11B12 | PAP | gH | 3.5 | 1.2 |
| 1 | 13H11 | GRA | gH | 1.12 | 0.4 |
| 1 | 3G16 | PEL | gH | 1.0 | 0.3 |
| 1 | 7H3 | PEL | gB | 3 | 0.6 |
| 1 | 10C6 | PEL | gB | 0.75 | 0.2 |
| 1 | 5F1 | PEL | gB | 0.5 | 0.1 |
| 1 | 6B4 | PEL | gB | 1.0 | 0.15 |
| 1 | 4H9 | PEL | gB | 10 | 0.4 |
| 1 | 2B11 | PEL | gB | 0.75 | 0.2 |
| 1 | 6L3 | PEL | gM/gN | 30 | 10 |

[1]Values indicating the concentration of antibody in μg/ml required to give a 90% reduction of hCMV (VR1814) infection of fibroblasts (e.g. MRC-9) or epithelial cells (e.g. ARPE retinal cells).
[2]Specificity as defined in Table 6.
[3]nn, not neutralizing at the highest concentration tested (10 μg/ml).

TABLE 5C

| Group | mAb | Specificity | 50% Neutralization[1] HUVEC | Mo-DC | BM-MSC |
|---|---|---|---|---|---|
| 1 | 7H3 | gB | nd | 0.06 | 2 |
| 1 | 10C6 | gB | 0.19 | 0.02 | 0.3 |
| 1 | 5F1 | gB | 0.21 | 0.05 | 0.3 |
| 1 | 6B4 | gB | nd | 0.11 | 2 |

[1]Values indicating the concentration of antibody in μg/ml required to give a 50% reduction of hCMV (VR1814) infection of primary cells. HUVEC, human umbilical vein endothelial cells, Mo-DC, monocyte-derived dendritic cells, BM-MSC, mesenchymal bone-marrow stromal cells.

Example 2: Identification of the Target Antigens Recognized by the Monoclonal Antibodies To map the specificity of the hCMV neutralizing antibodies, HEK293T cells were transfected with one or more vectors encoding full length hCMV proteins UL128, UL130, UL131A, gH, gL, gB, gM, and gN. After 36 h, cells were fixed, permeabilized and stained with the human monoclonal antibodies followed by goat anti-human IgG. FIG. 1 shows the binding of representative antibodies to HEK293T cells expressing one or more hCMV proteins. Table 6 shows the staining pattern of all the different antibodies to hCMV gene-transfected HEK293T cells. With the exception of antibody 15D8, that stained UL128-transfected cells, all the other Group 2 antibodies did not stain single gene transfectants, suggesting that they may recognize epitopes that require co-expression of more than one gene product. Indeed, five antibodies (4N10, 10F7, 10P3, 4I22 and 8L13) stained cells co-expressing UL130 and UL131A, six antibodies (2C12, 7B13, 7I13, 8C15, 8J16 and 9I6) stained cells co-expressing UL128, UL130 and UL131A, and one antibody (8I21) stained cells transfected with UL128 and UL130 as well as with gH and gL. All these antibodies also stained HEK293T cells transfected with all genes forming the gH/gL/UL128-130 complex. Among the Group 1 antibodies, three (11B12, 13H11 and 3G16) stained cells expressing the hCMV protein gH, six (7H3, 10C6, 5F1, 6B4, 4H9 and 2B11) stained cells expressing the hCMV protein gB and one (6L3) stained cells coexpressing the hCMV proteins gM and gN.

TABLE 6

| HEK293T cells transfected with: | Monoclonal antibody Group 2 | | | | Monoclonal antibody Group 1 | | |
|---|---|---|---|---|---|---|---|
| | 15D8 | 4N10 10F7 10P3 4I22 8L13 | 2C12 7B13 7I13 8C15 8J16 9I6 | 8I21 | 11B12 13H11 3G16 | 7H3 10C6 5F1 6B4 4H9 2B11 | 6L3 |
| UL128 | + | − | − | − | − | − | nd[1] |
| UL130 | − | − | − | − | − | − | nd |
| UL131A | − | − | − | − | − | − | nd |
| UL128 + UL130 | + | − | − | − | − | − | nd |
| UL128 + UL131A | + | − | − | − | − | − | nd |
| UL130 + UL131A | − | + | − | − | − | − | nd |
| UL128 + UL130 + UL131A | + | + | + | − | − | − | − |
| gH | − | − | − | − | + | − | − |
| gH + gL | − | − | − | − | + | − | − |
| gH + UL128 + UL130 + UL131A | + | + | + | − | + | nd | nd |
| gL + UL128 + UL130 + UL131A | + | + | + | − | − | nd | nd |
| gH + gL + UL128 | + | − | − | + | + | nd | nd |
| gH + gL + UL130 | − | − | − | + | + | nd | nd |
| gH + gL + UL131A | − | − | − | − | + | nd | nd |

TABLE 6-continued

| | Monoclonal antibody | | | | | | |
|---|---|---|---|---|---|---|---|
| | Group 2 | | | | Group 1 | | |
| HEK293T cells transfected with: | 15D8 | 4N10 10F7 10P3 4I22 8L13 | 2C12 7B13 7I13 8C15 8J16 9I6 | 8I21 | 11B12 13H11 3G16 | 7H3 10C6 5F1 6B4 4H9 2B11 | 6L3 |
| gH + gL + UL128 + UL130 | + | – | – | + | + | nd | nd |
| gH + gL + UL128 + UL130 + UL131A | + | + | + | + | + | – | – |
| gB | – | – | – | nd | – | + | – |
| gM | nd | – | – | nd | nd | nd | – |
| gN | nd | – | – | nd | nd | nd | – |
| gM + gN | – | – | – | – | nd | nd | + |

[1]nd, not done.

To further explore the identity of the antigen sites to which the antibodies bind, cross-competition experiments were performed. Here, HEK293T cells were transfected with vectors encoding full length hCMV proteins gH, gL, UL128, UL130 and UL131A. The cells were then incubated with a 20-fold excess of a competitor hCMV neutralizing antibody before addition of a biotinylated antibody. This procedure was repeated several times with different competitor antibodies and biotinylated antibodies. In these experiments four antibodies described in patent application Ser. No. 11/969,104 (11F11, 2F4 and 5A2) and patent application Ser. No. 12/174,568 (6G4) were included. The data is shown in Table 7A, B.

TABLE 7A

| Competitor | | Inhibition of binding (%) | | | | | | |
|---|---|---|---|---|---|---|---|---|
| (20-fold excess) | Specificity[1] | 15D8-biotin | 4N10-biotin | 10F7-biotin | 4I22-biotin | 1F11-biotin | 2F4-biotin | 5A2-biotin |
| 15D8 | UL128 | 100 | 0 | 0 | 0 | 0 | 0 | 0 |
| 4N10 | UL130/UL131A | 0 | 100 | 0 | 0 | 0 | 0 | 100 |
| 10F7 | UL130/UL131A | 0 | 0 | 100 | 100 | 100 | 100 | 0 |
| 10P3 | UL130/UL131A | 0 | nd | nd | 0 | 0 | 0 | Nd |
| 4I22 | UL130/UL131A | nd | 0 | 100 | 100 | 100 | Nd | 0 |
| 8L13 | UL130/UL131A | nd | nd | 100 | nd | 100 | Nd | nd |
| 1F11 | UL130/UL131A | 0 | 0 | 100 | 100 | 100 | 100 | 0 |
| 2F4 | UL130/UL131A | nd | 0 | 100 | 100 | 100 | 100 | 0 |
| 5A2 | UL130/UL131A | nd | 100 | 0 | 0 | 0 | 50[2] | 100 |
| 2C12 | UL128/UL130/UL131A | 0 | 0 | 0 | 0 | 0 | 0 | 0 |
| 7B13 | UL128/UL130/UL131A | nd | nd | nd | nd | nd | nd | nd |
| 7I13 | UL128/UL130/UL131A | nd | nd | nd | nd | 0 | nd | nd |
| 8C15 | UL128/UL130/UL131A | nd | nd | nd | 0 | nd | nd | nd |
| 8J16 | UL128/UL130/UL131A | nd | nd | nd | 0 | 0 | 0 | nd |
| 9I6 | UL128/UL130/UL131A | nd | nd | Nd | 0 | 0 | 0 | nd |
| 6G4 | UL128/UL130/UL131A | 0 | 0 | 0 | 0 | 0 | 0 | 0 |
| 8I21 | gH/gL/UL128/UL130 | 0 | 90 | nd | 0 | 0 | 0 | 95 |

[1]Specificity as defined is Table 6.
[2]Competition below 100% may be due to partial overlap of epitopes or to steric hindrance or to lower affinity.

TABLE 7B

| Competitor | | Inhibition of binding (%) | | | | | |
|---|---|---|---|---|---|---|---|
| (20-fold excess) | Specificity[1] | 2C12-biotin | 8C15-biotin | 8J16-biotin | 9I6-biotin | 6G4-biotin | 8I21-biotin |
| 15D8 | UL128 | 0 | nd | nd | nd | 0 | 0 |
| 4N10 | UL130/UL131A | 0 | nd | nd | nd | 0 | 90[2] |
| 10F7 | UL130/UL131A | 0 | nd | nd | nd | 0 | 0 |
| 10P3 | UL130/UL131A | 0 | nd | nd | nd | 0 | 0 |
| 4I22 | UL130/UL131A | 0 | nd | 0 | nd | 0 | 0 |
| 8L13 | UL130/UL131A | nd | nd | nd | nd | nd | nd |
| 1F11 | UL130/UL131A | 0 | nd | nd | nd | 0 | 0 |
| 2F4 | UL130/UL131A | 0 | nd | 0 | 0 | 0 | 0 |
| 5A2 | UL130/UL131A | 0 | nd | 0 | 0 | 0 | 92 |
| 2C12 | UL128/UL130/UL131A | 100 | 100 | 100 | 100 | 100 | 0 |
| 7B13 | UL128/UL130/UL131A | 100 | 100 | 100 | 100 | 100 | 0 |

TABLE 7B-continued

| Competitor (20-fold excess) | Specificity[1] | Inhibition of binding (%) | | | | | |
|---|---|---|---|---|---|---|---|
| | | 2C12-biotin | 8C15-biotin | 8J16-biotin | 9I6-biotin | 6G4-biotin | 8I21-biotin |
| 7I13 | UL128/UL130/UL131A | 0 | 0 | 0 | 0 | 0 | 0 |
| 8C15 | UL128/UL130/UL131A | 100 | 100 | 100 | 100 | 100 | 0 |
| 8J16 | UL128/UL130/UL131A | 100 | 100 | 100 | 70 | 100 | 0 |
| 9I6 | UL128/UL130/UL131A | 100 | 100 | 100 | 100 | 100 | 0 |
| 6G4 | UL128/UL130/UL131A | 100 | 100 | 100 | 100 | 100 | 0 |
| 8I21 | gH/gL/UL128/UL130 | 0 | nd | nd | nd | 0 | 100 |
| 3G16 | gH | 0 | nd | nd | nd | 0 | 0 |

[1]Specificity as defined is Table 6.
[2]Competition below 100% may be due to partial overlap of epitopes or to steric hindrance or to lower affinity.

Based on the data in Table 7A, B, at least seven distinct antigenic sites can be distinguished on the hCMV complex formed by gH, gL, UL128 and UL130 (Table 8). Site 1 is present in UL128 and is defined by antibody 15D8. Sites 2 to 4 are formed by the combination of UL130 and UL131A and are defined by the antibodies 10F7 4I22, 8L13, 1F11 and 2F4 (site 2), by 4N10 and 5A2 (site 3), and by 10P3 (site 4), respectively. Sites 5 and 6 are formed by the combination of UL128, UL130 and UL131A and are defined by antibodies 2C12, 7B13, 8C15, 8J16, 9I6 and 6G4 (site 5) and by 7I13 (site 6), respectively. Finally, site 7 is formed by the combination of gH, gL, UL128 and UL130 and is defined by the antibody 8I21. Antibodies defining site 7 and site 3 partially competed with each other, suggesting that these sites may be close in the structure of the gH/gL/UL128-131A complex.

It is anticipated that neutralizing antibodies targeted to different epitopes on the same target can be used in combination to achieve robust neutralization of virus infection, as exemplified by 10F7 and 4N10 or by 8J16 and 7I13. Moreover, it is anticipated that neutralizing antibodies targeted to different target molecules or combinations of target molecules may be used together to achieve robust virus neutralization. As one example, Table 8 suggests that 15D8 and 10F7, 15D8 and 2C12, or 8J16 and 8I21 could be combined to bring about additive or synergic hCMV neutralization effects.

Figure 2:
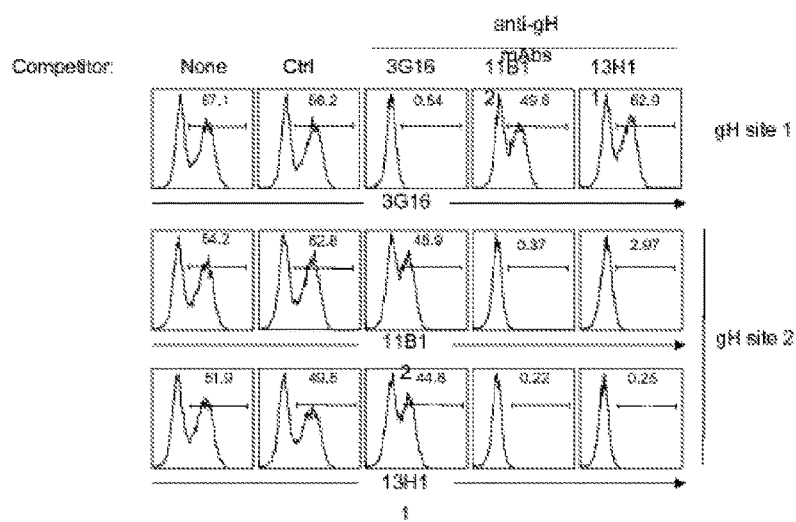
FIG. 2 shows cross-competition experiments in which HEK293T cells transfected with hCMV gH (A) or gB (B) gene were first incubated with an unlabeled competitor antibody followed by staining with a biotinylated anti-gH or anti-gB antibody.
Figure 2:
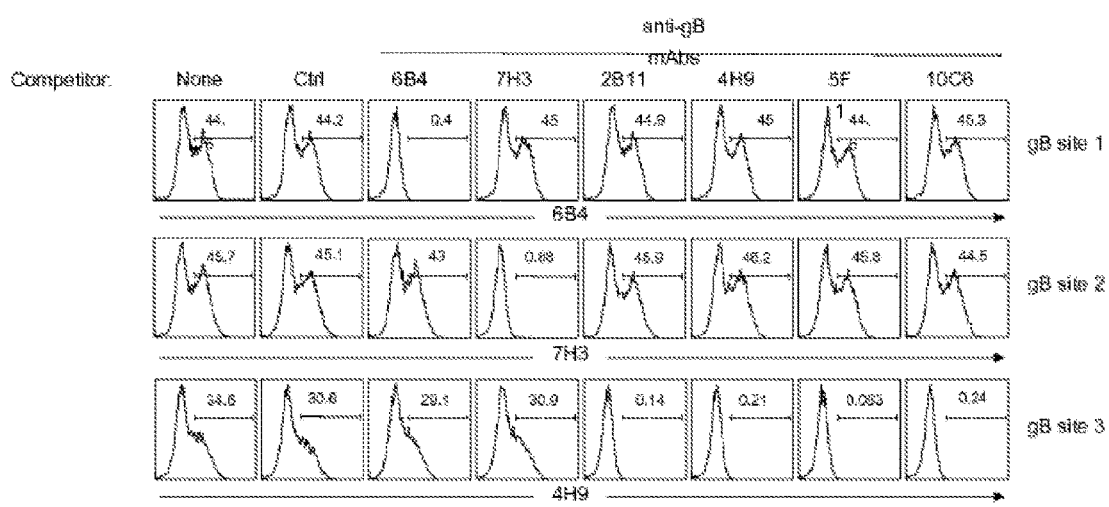

In a manner similar to what described in Table 7, HEK293T cells were transfected with a vector encoding full length gH to examine the cross-competition binding of the anti-gH antibodies. As can be seen in FIG. 2A and Table 9, at least two different binding sites were identified in the hCMV gH protein. The antibody 3G16 defines one site and the antibodies 11B12 and 13H11 define a second site. Finally, HEK293T cells were transfected with a vector encoding full length gB to examine the cross-competition binding of the anti-gB antibodies. As can be seen in FIG. 2B and Table 10, at least three different antigenic sites were identified in the hCMV gB protein. The antibody 6B4 defines one site, 7H3 defines a second site and the set of 10C6, 5F1, 4H9 and 2B11 define a third site. Antibody 6B4 (recognizing gB site 1) reacted by ELISA with the gB 69-78 peptide ($EC_{50}$ of 0.044 μg/ml). It is anticipated that antibodies that target different sites even on the same target molecule can be used in combination to achieve robust virus neutralization. It is anticipated that antibodies that target different sites even on the same target molecule can be used in combination to achieve robust virus neutralization.

TABLE 8

| Target antigen | Antigenic site | Antibodies defining the antigenic site |
|---|---|---|
| UL128 | 1 | 15D8 |
| UL130/UL131A | 2 | 10F7, 4I22, 8L13, 1F11, 2F4 |
| UL130/UL131A | 3 | 4N10, 5A2 |
| UL130/UL131A | 4 | 10P3 |
| UL128/UL130/UL131A | 5 | 2C12, 7B13, 8C15, 8J16, 9I6, 6G4 |
| UL128/UL130/UL131A | 6 | 7I13 |
| gH/gL/UL128/UL130 | 7 | 8I21 |

TABLE 9

| Competitor 20-fold excess | Specificity[1] | Inhibition of binding (%) of: | | | Antigenic site in gH |
|---|---|---|---|---|---|
| | | 3G16-biotin | 11B12-biotin | 13H11-biotin | |
| 3G16 | gH | 100 | 0 | 0 | 1 |
| 11B12 | gH | 0 | 100 | 100 | 2 |
| 13H11 | gH | 0 | 100 | 100 | 2 |

[1]As defined in Table 6.

TABLE 10

| Competitor 20-fold excess | Specificity[1] | Inhibition of binding (%) of: | | | | | | Antigenic site in gB |
|---|---|---|---|---|---|---|---|---|
| | | 7H3-biotin | 10C6-biotin | 5F1-biotin | 6B4-biotin | 4H9-biotin | 2B11-biotin | |
| 6B4 | gB | 0 | 0 | 0 | 100 | 0 | 0 | 1 |
| 7H3 | gB | 100 | 0 | 0 | 0 | 0 | 0 | 2 |
| 10C6 | gB | 0 | 100 | 100 | 0 | 100 | 100 | 3 |
| 5F1 | gB | 0 | 100 | 100 | 0 | 100 | 100 | 3 |

TABLE 10-continued

| Competitor | | Inhibition of binding (%) of: | | | | | | |
|---|---|---|---|---|---|---|---|---|
| 20-fold excess | Specificity[1] | 7H3-biotin | 10C6-biotin | 5F1-biotin | 6B4-biotin | 4H9-biotin | 2B11-biotin | Antigenic site in gB |
| 4H9 | gB | 0 | 100 | 100 | 0 | 100 | 100 | 3 |
| 2B11 | gB | 0 | 100 | 100 | 0 | 100 | 100 | 3 |

[1]As defined in Table 6.
2) Competition below 100% may be due to partial overlap of epitopes, to steric hindrance or to lower affinity.

To summarize, 15D8 binds to an epitope in UL128 that is distinct from the epitope recognized by 2C12, 7B13, 6G4 (all specific for a combination of UL128, UL130 and UL131A) and from the epitope recognized by 8I21 (specific for a combination of gH, gL, UL128 and UL130). In addition binding of 15D8 to its epitope is not inhibited by 4N10, 10F7, 10P3 and 1F11 (all specific for a combination of UL130 and UL131A).

4N10 binds to an epitope which requires expression of UL130 and UL131A and that is the same or largely overlapping to the epitopes recognized by 5A2 (specific for a combination of UL130 and UL131A) and 8I21 (specific for a combination of gH, gL, UL128 and UL130) but distinct from the epitopes recognized by 10F7, 4I22, 1F11, 2F4 (all specific for a combination of UL130 and UL131A), 2C12 and 6G4 (both specific for a combination of UL128, UL130 and UL131A). In addition binding of 4N10 to its epitope is not inhibited by 15D8 (specific for UL128).

10F7 binds to an epitope which requires expression of UL130 and UL131A that is the same or largely overlapping to the epitope(s) recognized by 4I22, 8L13, 1F11 and 2F4 but distinct from epitope(s) recognized by 4N10 and 5A2 (both specific for a combination of UL130 and UL131A) as well as distinct from epitopes recognized by 2C12 and 6G4 (both specific for a combination of UL128, UL130 and UL131A). In addition binding of 10F7 to its epitope is not inhibited by 15D8 (specific for UL128) or by 13H11 (specific for gH).

4I22 binds to an epitope which requires expression of UL130 and UL131A and that is the same or partially overlapping to epitope(s) recognized by 2F4, 1F11 and 10F7 but distinct from epitope(s) recognized by 4N10, 10P3 and 5A2 (all specific for a combination of UL130 and UL131A) as well as distinct from the epitopes recognized by 2C12, 8C15, 8J16, 9I6, 6G4 (all specific for a combination of UL128, UL130 and UL131A) and 8I21 (specific for a combination of gH, gL, UL128 and UL130. In addition binding of 4I22 to its epitope is not inhibited by the antibodies 15D8 (specific for UL128) or by 13H11 (specific for gH).

2C12 binds to an epitope which requires expression of hCMV UL128, UL130 and UL131A gene products and that is the same or largely overlapping to epitope(s) recognized by 7B13, 8C15, 8J16, 9I6 and 6G4 but distinct from the epitope recognized by 7I13 (all specific for a combination of UL128, UL130 and UL131A) and distinct from epitope(s) recognized by 15D8 (specific for UL128), 4N10, 10F7, 10P3, 4I22, 8L13, 1F11, 2F4, 5A2 (all specific for a combination of UL130 and UL131A) and 8I21 (specific for a combination of gH, gL, UL128 and UL130). In addition binding of 2C12 to its epitope is not inhibited by 3G16 (specific for gH).

8C15 binds to an epitope which requires expression of hCMV UL128, UL130 and UL131A gene products and that is the same or largely overlapping to epitope(s) recognized by 2C12, 7B13, 8J16, 9I6 and 6G4 but distinct from the epitope recognized by 7I13 (all specific for a combination of UL128, UL130 and UL131A).

8J16 binds to an epitope which requires expression of hCMV UL128, UL130 and UL131A gene products and that is the same or largely overlapping to epitope(s) recognized by 2C12, 7B13, 8C15, 9I6 and 6G4, but distinct from the epitope recognized by 7I13 (all specific for a combination of UL128, UL130 and UL131A) and from the epitope recognized by 4I22 (specific for a combination of UL130 and UL131A).

9I6 binds to an epitope which requires expression of hCMV UL128, UL130 and UL131A gene products and that is the same or largely overlapping to epitope(s) recognized by 2C12, 7B13, 8C15, 8J16 and 6G4 but distinct from the epitope recognized by 7I13 (all specific for a combination of UL128, UL130 and UL131A) and from the epitope(s) recognized by 2F4 and 5A2 (specific for a combination of UL130 and UL131A).

8I21 binds to an epitope which requires expression of hCMV gH, gL, UL128 and UL130 gene products and that may be partially overlapping to epitope(s) recognized by 4N10 and 5A2 (both specific for a combination of UL130 and UL131A) but distinct from epitopes recognized by 15D8 (specific UL128), 10F7, 10P3, 4I22, 1F11, 2F4 (all specific for a combination of UL130 and UL131A), 2C12, 7B13, 7I13, 8C15, 8J16, 9I6 and 6G4 (all specific for a combination of UL128, UL130 and UL131A). In addition binding of 8I21 to its epitope is not inhibited by 3G16 (specific for gH).

3G16 binds to an epitope in gH that is distinct from the epitope(s) recognized by 11B12 and 13H11 (both specific for gH).

11B12 binds to an epitope in gH that is the same or largely overlapping to the epitope recognized by 13H11 and distinct from the epitopes recognized by 3G16 (both specific for gH).

13H11 binds to an epitope in gH that is the same or largely overlapping to the epitope recognized by 11B12 and distinct from the epitopes recognized by 3G16 (both specific for gH).

6B4 recognizes an epitope in gB that is distinct from the epitope(s) recognized by 7H3, 4H9, 5F1, 10C6 and 2B11 (all specific for gB).

7H3 binds to an epitope in gB that is distinct from the epitope(s) recognized by 6B4, 7H3, 4H9, 5F1, 10C6 and 2B11 (all specific for gB).

10C6 binds to an epitope in gB that is the same or partially overlapping to the epitope(s) recognized by 5F1, 4H9 and 2B11, but distinct from the epitope(s) recognized by 7H3 and 6B4 (all specific for gB).

5F1 binds to an epitope in gB that is the same or largely overlapping to the epitope(s) recognized by 10C6, 4H9 and 2B11 but distinct from the epitope(s) recognized by 6B4 and 7H3 (all specific for gH).

4H9 binds to an epitope in gB that is the same or largely overlapping to the epitope(s) recognized by 5F1, 10C6 and 2B11, but distinct from the epitope(s) recognized by 6B4 and 7H3 (all specific for gH).

2B11 binds to an epitope in gB that is the same or largely overlapping to the epitope(s) recognized by 5F1, 10C6 and 4H9 but distinct from the epitope(s) recognized by 6B4 and 7H3 (all specific for gH).

Example 3: Breadth of Neutralizing Activity of Antibody 15D8

UL128 is the most conserved gene of the UL132-128 locus. However, sequences derived from several clinical isolates revealed the existence of 10 variants with one or more mutations when compared to the VR1814 sequence. We therefore investigated whether the binding of the UL128-specific antibody 15D8 would be affected by any of these mutations. To this aim, published amino acid sequences of variants of UL128 from clinical isolates (VR4603-M, VR4836-M, VR5001-1M, VR4254-M, VR4969-M, VR4313-M, VR4116-M, VR5235-T, VR5055-T, VR4168-A, VR1814-PCR) and laboratory strains (Towne, TB40/E, AD169, Merlin and Toledo) were aligned, and a gene was synthesized encoding a protein that includes all amino acid substitutions described as well as an additional mutation that we found to be generated at very high frequency in vitro upon PCR amplification (F33V). The nucleotide sequence of the synthetic gene was:

(SEQ ID NO: 371)
atgaacagcaaagacctgacgccgttcttgacgaccttgtggctgctatt ggaccacagccgcgtgccgcgggtacgcgcagaagaatgttgcgaattca taaacgtcaaccacccgccggaacgctgttacgatttcaaaatgtgcaat ctgttcaccgtcgcgctgcggtgtccggacggcgaagtctgctacagtcc cgagaaacggctgagattcgcgggatcgtcaccaccatgacccattcat tgacacgccaggtcatccacaacaaactgacgagctgcaactacaatccg ttatacctcgaagctgacgggcgaatacgctgcggcaaagtgagcgacaa ggcgcagtacctgctgggcgccgctggcagcgttccctatcgatggatca acctggaatacgacaagataacccggatcgtgggcctggatcagtacctg gagagcgttaagaaacacaaacggctggatgtgtgccgcgctaaatggg ctatatgctgcagtag.

Figure 3:
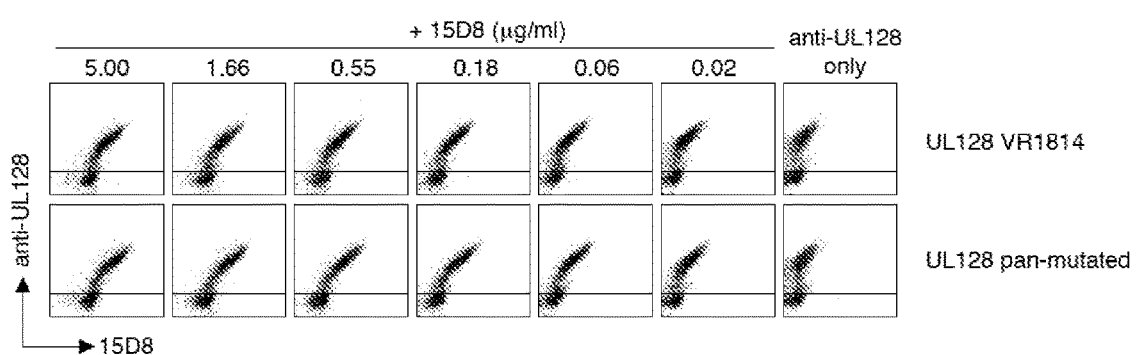
FIG. 3 shows staining of HEK293T cells expressing either the wild type VR1814 UL128 gene or a pan-mutated UL128 gene by human monoclonal antibody 15D8 and a non-competing anti-UL128 mouse monoclonal antibody. The pan-mutated UL128 gene contains substitutions of the wild type VR1814 sequence with known variants described in other clinical isolates and laboratory strains of hCMV.

HEK293T cells were transfected with the original UL128 from VR1814 or with the pan-mutated gene and stained with serial dilutions of 15D8 antibody. As shown in FIG. 3, the original and the pan-mutated UL128 protein were recognized by 15D8 with comparable efficiency (saturated staining at ~0.2 μg/ml). These findings indicate that 15D8 recognize a highly conserved epitope in the UL128 encoded protein.

All patents and publications referred to herein are expressly incorporated by reference in their entirety.

It should be noted that there are alternative ways of implementing the present invention and that various modifications can be made without departing from the scope and spirit of the invention. Accordingly, the present embodiments are to be considered as illustrative and not restrictive, and the invention is not to be limited to the details given herein, but may be modified within the scope and equivalents of the appended claims.

REFERENCES (THE CONTENTS OF WHICH ARE HEREBY INCORPORATED BY REFERENCE)

[1] Plachter et al. (1996) *Adv Virus Res* 46:195-261.
[2] Gerna et al. (2002) *J Med Virol* 66:335-339.
[3] Adler, B., L. Scrivano, Z. Ruzcics, B. Rupp, C. Sinzger, and U. Koszinowski. 2006. Role of human cytomegalovirus UL131A in cell type-specific virus entry and release. *J Gen Virol* 87:2451-2460.
[4] Gerna, G., E. Percivalle, D. Lilleri, L. Lozza, C. Fornara, G. Hahn, F. Baldanti, and M. G. Revello. 2005. Dendritic-cell infection by human cytomegalovirus is restricted to strains carrying functional UL131-128 genes and mediates efficient viral antigen presentation to CD8+ T cells. *J Gen Virol* 86:275-284.
[5] Hahn, G., M. G. Revello, M. Patrone, E. Percivalle, G. Campanini, A. Sarasini, M. Wagner, A. Gallina, G. Milanesi, U. Koszinowski, F. Baldanti, and G. Gerna. 2004. Human cytomegalovirus UL131-128 genes are indispensable for virus growth in endothelial cells and virus transfer to leukocytes. *J Virol* 78:10023-10033.
[6] Patrone, M., M. Secchi, L. Fiorina, M. Ierardi, G. Milanesi, and A. Gallina. 2005. Human cytomegalovirus UL130 protein promotes endothelial cell infection through a producer cell modification of the virion. *J Virol* 79:8361-8373.
[7] Wang, D., and T. Shenk. 2005. Human cytomegalovirus virion protein complex required for epithelial and endothelial cell tropism. *Proc Natl Acad Sci USA* 102: 18153-18158.
[8] Wang, D., and T. Shenk. 2005. Human cytomegalovirus UL131 open reading frame is required for epithelial cell tropism. *J Virol* 79:10330-10338.
[9] Nigro et al. 2005. Passive immunization during pregnancy for congenital cytomegalovirus infection. *N Engl J Med* 353:1350-1362.
[10] Borucki et al. 2004, A phase II, double-masked, randomized, placebo-controlled evaluation of a human monoclonal anti-Cytomegalovirus antibody (MSL-109) in combination with standard therapy versus standard therapy alone in the treatment of AIDS patients with Cytomegalovirus retinitis. *Antiviral Res* 64:103-111.
[11] McLean et al. 2005. Recognition of human cytomegalovirus by human primary immunoglobulins identifies an innate foundation to an adaptive immune response. *J Immunol,* 174:4768-4778.
[12] Lefranc et al. 2003. IMGT unique numbering for immunoglobulin and T cell receptor variable domains and Ig superfamily V-like domains. *Dev Comp Immunol.* 27(1):55-77.
[13] Lefranc et al. 1997. Unique database numbering system for immunogenetic analysis. *Immunology Today,* 18:509.
[14] Lefranc (1999) *The Immunologist,* 7:132-136.
[15] U.S. Pat. No. 3,766,162
[16] U.S. Pat. No. 3,791,932
[17] U.S. Pat. No. 3,817,837
[18] U.S. Pat. No. 4,233,402
[19] U.S. Pat. No. 4,676,980
[20] U.S. Pat. No. 4,831,175
[21] U.S. Pat. No. 5,595,721
[22] WO00/52031
[23] WO00/52473
[24] U.S. Pat. No. 4,766,106
[25] U.S. Pat. No. 4,179,337
[26] U.S. Pat. No. 4,495,285
[27] U.S. Pat. No. 4,609,546

[28] Knauf et al. (1988) *J. Bio. Chem.* 263:15064-15070
[29] Gabizon et al. (1982) *Cancer Research* 42:4734
[30] Cafiso (1981) *Biochem Biophys Acta* 649:129
[31] Szoka (1980) *Ann. Rev. Biophys. Eng.* 9:467
[32] Poznansky et al. (1980) *Drug Delivery Systems* (R. L. Juliano, ed., Oxford, N.Y.) pp. 253-315
[33] Poznansky (1984) *Pharm Revs* 36:277
[34] Kohler, G. and Milstein, C., 1975, *Nature* 256:495-497.
[35] Kozbar et al. 1983, *Immunology Today* 4:72.
[36] WO2004/076677
[37] Chapter 4 of *Kuby Immunology* (4th edition, 2000; ASIN: 0716733315
[38] Jones et al. *Biotechnol Prog* 2003, 19(1):163-8
[39] Cho et al. *Cytotechnology* 2001, 37:23-30
[40] Cho et al. *Biotechnol Prog* 2003, 19:229-32
[41] U.S. Pat. No. 5,807,715
[42] U.S. Pat. No. 6,300,104

The invention claimed is:

1. A vector comprising one or more nucleic acid molecules encoding a heavy chain variable region and/or light chain variable region of an antibody that binds to hCMV, wherein the heavy chain variable region is encoded by the nucleotide sequence SEQ ID NO: 63, and the light chain variable region is encoded by the nucleotide sequence SEQ ID NO: 64.

2. An isolated host cell comprising the vector of claim 1.

3. The isolated host cell of claim 2, wherein the host cell is a mammalian cell.

4. The isolated host cell of claim 3, wherein the mammalian cell is a CHO cell.

5. A method of producing an antibody that binds to hCMV, comprising expressing one or more nucleic acid molecules encoding the heavy and light chain variable regions of the antibody in a host cell, thereby producing the antibody, wherein the heavy chain variable region is encoded by the nucleotide sequence SEQ ID NO: 63, and the light chain variable region is encoded by the nucleotide sequence SEQ ID NO: 64.

6. A vector comprising one or more nucleic acid molecules encoding a heavy chain variable region and/or light chain variable region of an antibody that binds to hCMV, wherein the heavy chain variable region is encoded by the nucleotide sequence SEQ ID NO: 127, and the light chain variable region is encoded by the nucleotide sequence SEQ ID NO: 128.

* * * * *

SEQUENCE LISTING

```
<160> NUMBER OF SEQ ID NOS: 371

<210> SEQ ID NO 1
<211> LENGTH: 8
<212> TYPE: PRT
<213> ORGANISM: Homo sapiens

<400> SEQUENCE: 1

Gly Gly Thr Phe Ser Ser Tyr Val
1               5

<210> SEQ ID NO 2
<211> LENGTH: 8
<212> TYPE: PRT
<213> ORGANISM: Homo sapiens

<400> SEQUENCE: 2

Val Ile Pro Ile Phe Asp Thr Val
1               5

<210> SEQ ID NO 3
<211> LENGTH: 21
<212> TYPE: PRT
<213> ORGANISM: Homo sapiens

<400> SEQUENCE: 3

Ala Arg Gly Ile Leu Ala Tyr Cys Gly Gly Asp Cys Tyr Asn Thr Pro
1               5                   10                  15

Tyr Gly Met Asp Val
            20

<210> SEQ ID NO 4
<211> LENGTH: 6
<212> TYPE: PRT
<213> ORGANISM: Homo sapiens

<400> SEQUENCE: 4

Gln Ser Ile Ser Ser Trp
1               5

<210> SEQ ID NO 5
<211> LENGTH: 3
<212> TYPE: PRT
<213> ORGANISM: Homo sapiens

<400> SEQUENCE: 5

Lys Ala Ser
1

<210> SEQ ID NO 6
<211> LENGTH: 8
<212> TYPE: PRT
<213> ORGANISM: Homo sapiens

<400> SEQUENCE: 6
```

```
Gln Gln Tyr Asn Ser Ser Trp Thr
1               5
```

<210> SEQ ID NO 7
<211> LENGTH: 24
<212> TYPE: DNA
<213> ORGANISM: Homo sapiens

<400> SEQUENCE: 7
ggaggcacct tcagcagcta tgtt                                             24

<210> SEQ ID NO 8
<211> LENGTH: 24
<212> TYPE: DNA
<213> ORGANISM: Homo sapiens

<400> SEQUENCE: 8
gtcatcccta tctttgatac agta                                             24

<210> SEQ ID NO 9
<211> LENGTH: 63
<212> TYPE: DNA
<213> ORGANISM: Homo sapiens

<400> SEQUENCE: 9
gcgagaggaa ttctagcata ttgtggtggt gattgctata ataccccta cggtatggac       60 gtc                                                                    63

<210> SEQ ID NO 10
<211> LENGTH: 18
<212> TYPE: DNA
<213> ORGANISM: Homo sapiens

<400> SEQUENCE: 10
cagagtatta gtagctgg                                                    18

<210> SEQ ID NO 11
<211> LENGTH: 9
<212> TYPE: DNA
<213> ORGANISM: Homo sapiens

<400> SEQUENCE: 11 aaggcgtct                                                               9

<210> SEQ ID NO 12
<211> LENGTH: 24
<212> TYPE: DNA
<213> ORGANISM: Homo sapiens

<400> SEQUENCE: 12
caacagtata atagttcgtg gacg                                             24

<210> SEQ ID NO 13
<211> LENGTH: 128
<212> TYPE: PRT
<213> ORGANISM: Homo sapiens

<400> SEQUENCE: 13

```
Gln Val Gln Leu Val Gln Ser Gly Ala Glu Val Lys Lys Pro Gly Ser
1               5                   10                  15

Ser Val Arg Val Ser Cys Lys Ala Ser Gly Gly Thr Phe Ser Ser Tyr
            20                  25                  30
```

Val Ile Ile Trp Val Arg Gln Ala Pro Gly Gln Gly Leu Glu Trp Met
        35                  40                  45

Gly Gly Val Ile Pro Ile Phe Asp Thr Val Asn Tyr Ala Gln Lys Phe
 50                  55                  60

Gln Gly Arg Val Thr Ile Thr Ala Asp Glu Ser Thr Ser Thr Ala Tyr
65                  70                  75                  80

Met Glu Leu Ser Ser Leu Lys Ser Glu Asp Thr Ala Val Tyr Tyr Cys
                85                  90                  95

Ala Arg Gly Ile Leu Ala Tyr Cys Gly Gly Asp Cys Tyr Asn Thr Pro
            100                 105                 110

Tyr Gly Met Asp Val Trp Gly Gln Gly Thr Thr Val Thr Val Ser Ser
        115                 120                 125

<210> SEQ ID NO 14
<211> LENGTH: 106
<212> TYPE: PRT
<213> ORGANISM: Homo sapiens

<400> SEQUENCE: 14

Asp Ile Gln Met Thr Gln Ser Pro Ser Ile Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ile Gly Val Pro Ser Arg Ile Ser Gly
 50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Ser Trp Thr
                85                  90                  95

Phe Gly Gln Gly Thr Lys Val Glu Ile Lys
            100                 105

<210> SEQ ID NO 15
<211> LENGTH: 385
<212> TYPE: DNA
<213> ORGANISM: Homo sapiens

<400> SEQUENCE: 15
caggtgcagc tggtgcagtc tggggctgag gtgaagaagc ctgggtcctc ggtgagggtc    60
tcctgcaagg cttctggagg caccttcagc agctatgtta tcatctgggt gcgacaggcc   120
cctggacaag gtcttgagtg gatggggggg gtcatcccta tctttgatac agtaaattac   180
gcacagaagt tccagggcag agtcacgatt accgcggacg aatccacgag tactgcctac   240
atggagctga gcagcctgaa atctgaggac acggccgtat attactgtgc gagaggaatt   300
ctagcatatt gtggtggtga ttgctataat accccttacg gtatggacgt ctggggccaa   360
gggaccacgg tcaccgtctc ctcag                                         385

<210> SEQ ID NO 16
<211> LENGTH: 319
<212> TYPE: DNA
<213> ORGANISM: Homo sapiens

<400> SEQUENCE: 16
gacatccaga tgacccagtc tccttccatc ctgtctgcat ctgtaggaga cagagtcacc    60

```
atcacttgcc gggccagtca gagtattagt agctggttgg cctggtatca gcagaaacca        120
gggaaagccc caaaactcct aatctataag gcgtctagtt tagaaattgg ggtcccatca        180
aggatcagcg gcagtggatc tgggacagaa ttcactctca ccatcagcag cctgcagcct        240
gatgattttg caacttatta ctgccaacag tataatagtt cgtggacgtt cggccaaggg        300
acgaaggtgg aaatcaaac                                                    319
```

```
<210> SEQ ID NO 17
<211> LENGTH: 8
<212> TYPE: PRT
<213> ORGANISM: Homo sapiens

<400> SEQUENCE: 17

Gly Phe Thr Phe Gly Asp Tyr Ala
1               5

<210> SEQ ID NO 18
<211> LENGTH: 10
<212> TYPE: PRT
<213> ORGANISM: Homo sapiens

<400> SEQUENCE: 18

Ile Arg Ser Lys Ala Tyr Gly Gly Thr Thr
1               5                   10

<210> SEQ ID NO 19
<211> LENGTH: 18
<212> TYPE: PRT
<213> ORGANISM: Homo sapiens

<400> SEQUENCE: 19

Thr Arg Ala Ser Ser Leu Leu Trp Leu Leu Asn Pro Gln Pro Asn Phe
1               5                   10                  15

Asp Tyr

<210> SEQ ID NO 20
<211> LENGTH: 6
<212> TYPE: PRT
<213> ORGANISM: Homo sapiens

<400> SEQUENCE: 20

Asn Ile Gly Ser Asn Asn
1               5

<210> SEQ ID NO 21
<211> LENGTH: 3
<212> TYPE: PRT
<213> ORGANISM: Homo sapiens

<400> SEQUENCE: 21

Asp Asp Ser
1

<210> SEQ ID NO 22
<211> LENGTH: 11
<212> TYPE: PRT
<213> ORGANISM: Homo sapiens

<400> SEQUENCE: 22

Gln Val Trp Asp Ser Ser Ser Asp His Pro Val
1               5                   10
```

<210> SEQ ID NO 23
<211> LENGTH: 24
<212> TYPE: DNA
<213> ORGANISM: Homo sapiens

<400> SEQUENCE: 23
ggattcacct tggtgatta tgct                                    24

<210> SEQ ID NO 24
<211> LENGTH: 30
<212> TYPE: DNA
<213> ORGANISM: Homo sapiens

<400> SEQUENCE: 24
attagaagca aagcttatgg tgggacaaca                             30

<210> SEQ ID NO 25
<211> LENGTH: 54
<212> TYPE: DNA
<213> ORGANISM: Homo sapiens

<400> SEQUENCE: 25
actagagcat cttcattact atggttacta aaccctcaac ccaactttga ctac  54

<210> SEQ ID NO 26
<211> LENGTH: 18
<212> TYPE: DNA
<213> ORGANISM: Homo sapiens

<400> SEQUENCE: 26
aacattggaa gtaacaat                                          18

<210> SEQ ID NO 27
<211> LENGTH: 9
<212> TYPE: DNA
<213> ORGANISM: Homo sapiens

<400> SEQUENCE: 27 gatgatagc                                                     9

<210> SEQ ID NO 28
<211> LENGTH: 33
<212> TYPE: DNA
<213> ORGANISM: Homo sapiens

<400> SEQUENCE: 28
caggtgtggg atagtagtag tgatcatccg gta                         33

<210> SEQ ID NO 29
<211> LENGTH: 127
<212> TYPE: PRT
<213> ORGANISM: Homo sapiens

<400> SEQUENCE: 29

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Gly Asp Tyr
            20                  25                  30

Ala Met Ser Trp Phe Arg Gln Ala Pro Gly Lys Gly Leu Glu Trp Val
        35                  40                  45

Gly Phe Ile Arg Ser Lys Ala Tyr Gly Gly Thr Thr Glu Tyr Ala Ala
    50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Val Tyr
            85                  90                  95

Tyr Cys Thr Arg Ala Ser Ser Leu Leu Trp Leu Leu Asn Pro Gln Pro
        100                 105                 110

Asn Phe Asp Tyr Trp Gly Gln Gly Thr Leu Val Thr Val Ser Ser
    115                 120                 125

<210> SEQ ID NO 30
<211> LENGTH: 108
<212> TYPE: PRT
<213> ORGANISM: Homo sapiens

<400> SEQUENCE: 30

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Asn Asn Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
            85                  90                  95

Pro Val Phe Gly Gly Gly Thr Lys Leu Thr Val Leu
        100                 105

<210> SEQ ID NO 31
<211> LENGTH: 382
<212> TYPE: DNA
<213> ORGANISM: Homo sapiens

<400> SEQUENCE: 31
gaggtgcagc tggtggagtc tgggggaggc ttggtacagc cagggcggtc cctgagactc      60
tcctgtacag cttctggatt cacctttggt gattatgcta tgagctggtt ccgccaggct     120
ccagggaagg gctggagtg gtaggtttc attagaagca aagcttatgg tgggacaaca      180
gaatacgccg cgtctgtgaa aggcagattc accatctcaa gagatgattc aaaaagcatc     240
gcctatctgc aaatgaacag cctgaaaacc gaggacacag ccgtgtatta ctgtactaga     300
gcatcttcat tactatggtt actaaaccct caacccaact ttgactactg gggccaggga     360
accctggtca ccgtctcctc ag                                              382

<210> SEQ ID NO 32
<211> LENGTH: 325
<212> TYPE: DNA
<213> ORGANISM: Homo sapiens

<400> SEQUENCE: 32
tcctatgtgc tgactcagcc accctcggtg tcagtggccc caggacagac ggccaggatt      60
acctgtgggg gaaacaacat tggaagtaac aatgtgcact ggtaccagca gaagccaggc     120
caggcccctg tgctggtcgt ctatgatgat agcgaccggc cctcagggat ccctgagcga     180
ttctctggct ccaactctgg gaacacggcc accctgacca tcagcagggt cgaagccggg     240

```
gatgaggccg actattactg tcaggtgtgg gatagtagta gtgatcatcc ggtattcggc    300
ggagggacca agctgaccgt cctag                                          325
```

<210> SEQ ID NO 33
<211> LENGTH: 8
<212> TYPE: PRT
<213> ORGANISM: Homo sapiens

<400> SEQUENCE: 33

Gly Phe Thr Phe His Asn Tyr Arg
1               5

<210> SEQ ID NO 34
<211> LENGTH: 8
<212> TYPE: PRT
<213> ORGANISM: Homo sapiens

<400> SEQUENCE: 34

Ile Lys Gln Asp Gly Ser Glu Lys
1               5

<210> SEQ ID NO 35
<211> LENGTH: 19
<212> TYPE: PRT
<213> ORGANISM: Homo sapiens

<400> SEQUENCE: 35

Ala Arg Gly Glu Gly Tyr Thr Tyr Gly Val Val Tyr Ser Tyr Ser Ala
1               5                   10                  15

Met Asp Val

<210> SEQ ID NO 36
<211> LENGTH: 6
<212> TYPE: PRT
<213> ORGANISM: Homo sapiens

<400> SEQUENCE: 36

Val Leu Pro Asn Gln Tyr
1               5

<210> SEQ ID NO 37
<211> LENGTH: 3
<212> TYPE: PRT
<213> ORGANISM: Homo sapiens

<400> SEQUENCE: 37

Lys Asp Thr
1

<210> SEQ ID NO 38
<211> LENGTH: 11
<212> TYPE: PRT
<213> ORGANISM: Homo sapiens

<400> SEQUENCE: 38

Gln Ser Ala Asp Ser Ser Gly Ala Asp Tyr Val
1               5                   10

<210> SEQ ID NO 39
<211> LENGTH: 24
<212> TYPE: DNA
<213> ORGANISM: Homo sapiens

<400> SEQUENCE: 39
ggattcacct ttcataacta tcgc                                              24

<210> SEQ ID NO 40
<211> LENGTH: 24
<212> TYPE: DNA
<213> ORGANISM: Homo sapiens

<400> SEQUENCE: 40
ataaagcaag atggaagtga gaaa                                              24

<210> SEQ ID NO 41
<211> LENGTH: 57
<212> TYPE: DNA
<213> ORGANISM: Homo sapiens

<400> SEQUENCE: 41
gcgaggggtg aagggtacac ctatggtgtc gtctactcct attccgctat ggacgtc          57

<210> SEQ ID NO 42
<211> LENGTH: 18
<212> TYPE: DNA
<213> ORGANISM: Homo sapiens

<400> SEQUENCE: 42
gtattgccaa accaatat                                                     18

<210> SEQ ID NO 43
<211> LENGTH: 9
<212> TYPE: DNA
<213> ORGANISM: Homo sapiens

<400> SEQUENCE: 43 aaagacact                                                                9

<210> SEQ ID NO 44
<211> LENGTH: 33
<212> TYPE: DNA
<213> ORGANISM: Homo sapiens

<400> SEQUENCE: 44
caatcagcag acagcagtgg tgccgattat gtc                                    33

<210> SEQ ID NO 45
<211> LENGTH: 126
<212> TYPE: PRT
<213> ORGANISM: Homo sapiens

<400> SEQUENCE: 45

Glu Val Gln Leu Val Glu Ser Gly Gly Gly Leu Val Arg Pro Gly Gly
1               5                   10                  15

Ser Leu Arg Leu Ser Cys Ala Ala Ser Gly Phe Thr Phe His Asn Tyr
            20                  25                  30

Arg Met Asn Trp Val Arg Gln Ala Pro Gly Lys Gly Leu Glu Trp Val
        35                  40                  45

Ala Asn Ile Lys Gln Asp Gly Ser Glu Lys Ser Tyr Val Asp Ser Val
    50                  55                  60

Arg Gly Arg Phe Thr Thr Ser Arg Asp Asn Ser Lys Asn Ser Leu Tyr
65                  70                  75                  80

Leu Gln Ile Asn Ser Leu Arg Ala Glu Asp Thr Ala Val Tyr Tyr Cys
                85                  90                  95

Ala Arg Gly Glu Gly Tyr Thr Tyr Gly Val Val Tyr Ser Tyr Ser Ala
            100                 105                 110

Met Asp Val Trp Gly Gln Gly Thr Thr Val Ile Val Ser Ser
            115                 120                 125

<210> SEQ ID NO 46
<211> LENGTH: 108
<212> TYPE: PRT
<213> ORGANISM: Homo sapiens

<400> SEQUENCE: 46

Ser Tyr Glu Leu Thr Gln Pro Pro Ser Val Ser Val Ser Pro Gly Gln
1               5                   10                  15

Thr Ala Arg Ile Thr Cys Ser Gly Asn Val Leu Pro Asn Gln Tyr Ala
            20                  25                  30

Ser Trp Tyr Gln Gln Lys Pro Gly Gln Ala Pro Val Leu Val Ile Tyr
        35                  40                  45

Lys Asp Thr Glu Arg Pro Ser Gly Ile Pro Gly Arg Phe Ser Gly Ser
50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ser Gly Ala Asp
                85                  90                  95

Tyr Val Phe Gly Thr Gly Thr Lys Val Thr Val Leu
            100                 105

<210> SEQ ID NO 47
<211> LENGTH: 379
<212> TYPE: DNA
<213> ORGANISM: Homo sapiens

<400> SEQUENCE: 47
gaggtgcagc tggtagagtc tgggggaggc ttggtccggc ctggggggtc cctgagactc      60
tcatgtgcag cctctggatt caccttcat aactatcgca tgaactgggt ccgccaggct      120
ccagggaagg ggctggagtg ggtggccaac ataaagcaag atggaagtga gaaatcctat     180
gtggactctg tgaggggccg attcaccacc tccagagaca actccaagaa ttcactctat     240
ctgcaaatta acagcctgcg agccgaggac acggctgtct attactgtgc gaggggtgaa     300
gggtacacct atggtgtcgt ctactcctat tccgctatgg acgtctgggg ccaagggacc     360
acagtcatcg tctcctcag                                                  379

<210> SEQ ID NO 48
<211> LENGTH: 325
<212> TYPE: DNA
<213> ORGANISM: Homo sapiens

<400> SEQUENCE: 48
tcctatgagc tgacacagcc accctcggtg tcagtgtccc caggacagac ggccaggatc      60
acctgctctg gaaatgtatt gccaaaccaa tatgcttctt ggtaccagca gaagccaggc     120
caggcccctg tattggtgat atataaagac actgagaggc cctcagggat ccctgggcga     180
ttctctggct ccagctcagg gacgacagtc acgttgacca tcagtggagt ccaggcagag     240
gacgaggctg actattactg tcaatcagca gacagcagtg gtgccgatta tgtcttcgga     300
actgggacca aggtcaccgt cctag                                           325

-continued

```
<210> SEQ ID NO 49
<211> LENGTH: 8
<212> TYPE: PRT
<213> ORGANISM: Homo sapiens

<400> SEQUENCE: 49

Gly Phe Thr Phe Ser Ser Tyr Ala
1               5

<210> SEQ ID NO 50
<211> LENGTH: 8
<212> TYPE: PRT
<213> ORGANISM: Homo sapiens

<400> SEQUENCE: 50

Ile Ser Tyr Asp Gly Asp Asn Lys
1               5

<210> SEQ ID NO 51
<211> LENGTH: 19
<212> TYPE: PRT
<213> ORGANISM: Homo sapiens

<400> SEQUENCE: 51

Ala Arg Glu Glu Leu Val Gly Leu Met Pro Pro Tyr Tyr Asn Tyr Gly
1               5                   10                  15

Leu Asp Val

<210> SEQ ID NO 52
<211> LENGTH: 8
<212> TYPE: PRT
<213> ORGANISM: Homo sapiens

<400> SEQUENCE: 52

Asn Ser Asn Ile Gly Asn Asn Tyr
1               5

<210> SEQ ID NO 53
<211> LENGTH: 3
<212> TYPE: PRT
<213> ORGANISM: Homo sapiens

<400> SEQUENCE: 53

Asp Asn Asp
1

<210> SEQ ID NO 54
<211> LENGTH: 12
<212> TYPE: PRT
<213> ORGANISM: Homo sapiens

<400> SEQUENCE: 54

Glu Thr Trp Asp Thr Ser Leu Ser Ala Ala Val Val
1               5                   10

<210> SEQ ID NO 55
<211> LENGTH: 24
<212> TYPE: DNA
<213> ORGANISM: Homo sapiens

<400> SEQUENCE: 55
ggattcacct tcagttccta tgct                                          24

<210> SEQ ID NO 56
```

```
<211> LENGTH: 24
<212> TYPE: DNA
<213> ORGANISM: Homo sapiens

<400> SEQUENCE: 56
atttcatatg atggcgacaa caaa                                              24

<210> SEQ ID NO 57
<211> LENGTH: 57
<212> TYPE: DNA
<213> ORGANISM: Homo sapiens

<400> SEQUENCE: 57
gcgagagaag agttagtcgg gttgatgcct ccctattaca actacggatt ggacgtc          57

<210> SEQ ID NO 58
<211> LENGTH: 24
<212> TYPE: DNA
<213> ORGANISM: Homo sapiens

<400> SEQUENCE: 58
aactccaaca tcgggaataa ttat                                              24

<210> SEQ ID NO 59
<211> LENGTH: 9
<212> TYPE: DNA
<213> ORGANISM: Homo sapiens

<400> SEQUENCE: 59 gacaatgat                                                                9

<210> SEQ ID NO 60
<211> LENGTH: 36
<212> TYPE: DNA
<213> ORGANISM: Homo sapiens

<400> SEQUENCE: 60
gaaacatggg ataccagcct gagtgctgct gttgtc                                 36

<210> SEQ ID NO 61
<211> LENGTH: 126
<212> TYPE: PRT
<213> ORGANISM: Homo sapiens

<400> SEQUENCE: 61
```

Gln Val Gln Leu Val Glu Ser Gly Gly Val Val Gln Pro Gly Arg
1               5                   10                  15

Ser Leu Arg Leu Ser Cys Val Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Asp Asn Lys Tyr Ala Asp Ser Val
    50                  55                  60

Lys Gly Arg Phe Arg Ile Ser Arg Asp Thr Ser Lys Asn Thr Leu Tyr
65                  70                  75                  80

Leu Glu Met Asn Ser Leu Arg Ala Ala Asp Thr Ala Ile Tyr Tyr Cys
                85                  90                  95

Ala Arg Glu Glu Leu Val Gly Leu Met Pro Pro Tyr Tyr Asn Tyr Gly
            100                 105                 110

Leu Asp Val Trp Gly Gln Gly Thr Thr Val Thr Val Ser Ser
        115                 120                 125

<210> SEQ ID NO 62
<211> LENGTH: 111
<212> TYPE: PRT
<213> ORGANISM: Homo sapiens

<400> SEQUENCE: 62

Gln Ser Val Leu Thr Gln Pro Pro Ser Val Ser Ala Ala Pro Gly Gln
1               5                   10                  15
Lys Val Thr Ile Ser Cys Ser Gly Ser Asn Ser Asn Ile Gly Asn Asn
            20                  25                  30
Tyr Val Ser Trp Tyr Gln Gln Leu Pro Gly Arg Ala Pro Lys Leu Leu
        35                  40                  45
Ile Tyr Asp Asn Asp His Arg Pro Ser Gly Ile Pro Asp Arg Phe Ser
    50                  55                  60
Gly Ser Lys Ser Gly Thr Ser Ala Thr Leu Val Ile Thr Gly Leu Gln
65                  70                  75                  80
Thr Gly Asp Glu Ala Asp Tyr Tyr Cys Glu Thr Trp Asp Thr Ser Leu
                85                  90                  95
Ser Ala Ala Val Val Phe Gly Gly Gly Thr Lys Leu Thr Val Leu
            100                 105                 110

<210> SEQ ID NO 63
<211> LENGTH: 379
<212> TYPE: DNA
<213> ORGANISM: Homo sapiens

<400> SEQUENCE: 63
caggtgcagc tggtggagtc tgggggaggg gtggtccagc ctggggaggtc cctgagactc    60 tcctgtgtag cctctggatt caccttcagt tcctatgcta tgcactgggt ccgccaggct   120
ccaggcaagg gactggagtg gtggcagtt atttcatatg atggcgacaa caaattctac   180
gcagactccg tgaagggccg attcaggatc tccagagaca catccaagaa tacactgtat   240
ctggaaatga acagcctgag agctgcggac acggctatat attactgtgc gagagaagag   300
ttagtcgggt tgatgcctcc ctattacaac tacggattgg acgtctgggg ccaaggaacc   360
acggtcaccg tctcgtcag                                                 379

<210> SEQ ID NO 64
<211> LENGTH: 334
<212> TYPE: DNA
<213> ORGANISM: Homo sapiens

<400> SEQUENCE: 64
cagtctgtgt tgactcagcc gccctcagtg tctgcggccc caggacagaa ggtcaccatc    60
tcctgctctg gaagcaactc caacatcggg aataattatg tatcgtggta ccagcagctc   120
ccaggaagag ccccccaaact cctcatttat gacaatgatc accgaccctc agggattcct   180
gaccgattct ctggctccaa gtctggcacg tcagccaccc tggtcatcac cggactccag   240
actggggacg aggccgatta ttactgcgaa acatgggata ccagcctgag tgctgctgtt   300
gtcttcggcg gagggaccaa gctgaccgtc ctac                               334

<210> SEQ ID NO 65
<211> LENGTH: 10
<212> TYPE: PRT
<213> ORGANISM: Homo sapiens

<400> SEQUENCE: 65

```
<210> SEQ ID NO 66
<211> LENGTH: 7
<212> TYPE: PRT
<213> ORGANISM: Homo sapiens

<400> SEQUENCE: 66
```

Gly Phe Ser Leu Asn Thr Asn Gly Val Gly
1               5                   10

```
<210> SEQ ID NO 66
<211> LENGTH: 7
<212> TYPE: PRT
<213> ORGANISM: Homo sapiens

<400> SEQUENCE: 66
```

Ile Tyr Trp Asn Gly Asn Glu
1               5

```
<210> SEQ ID NO 67
<211> LENGTH: 17
<212> TYPE: PRT
<213> ORGANISM: Homo sapiens

<400> SEQUENCE: 67
```

Val His Trp Pro Gln Gly Leu Thr Thr Val Thr Arg Leu Ala Phe Asp
1               5                   10                  15

Ile

```
<210> SEQ ID NO 68
<211> LENGTH: 9
<212> TYPE: PRT
<213> ORGANISM: Homo sapiens

<400> SEQUENCE: 68
```

Thr Ser Asp Val Gly Arg Tyr Asn Phe
1               5

```
<210> SEQ ID NO 69
<211> LENGTH: 3
<212> TYPE: PRT
<213> ORGANISM: Homo sapiens

<400> SEQUENCE: 69
```

Asp Val Ser
1

```
<210> SEQ ID NO 70
<211> LENGTH: 12
<212> TYPE: PRT
<213> ORGANISM: Homo sapiens

<400> SEQUENCE: 70
```

Cys Ser Tyr Ala Gly Gly Asn Phe Phe Ser Tyr Val
1               5                   10

```
<210> SEQ ID NO 71
<211> LENGTH: 30
<212> TYPE: DNA
<213> ORGANISM: Homo sapiens

<400> SEQUENCE: 71
```
ggcttctcac tcaacactaa tggagtgggt                                      30

```
<210> SEQ ID NO 72
<211> LENGTH: 21
<212> TYPE: DNA
<213> ORGANISM: Homo sapiens

<400> SEQUENCE: 72
```
atttactgga atggtaatga g         21

<210> SEQ ID NO 73
<211> LENGTH: 51
<212> TYPE: DNA
<213> ORGANISM: Homo sapiens

<400> SEQUENCE: 73
gtacactggc cccaagggtt gactacggtg acaagacttg cttttgatat c         51

<210> SEQ ID NO 74
<211> LENGTH: 27
<212> TYPE: DNA
<213> ORGANISM: Homo sapiens

<400> SEQUENCE: 74
accagtgatg ttggtcgtta taacttt         27

<210> SEQ ID NO 75
<211> LENGTH: 9
<212> TYPE: DNA
<213> ORGANISM: Homo sapiens

<400> SEQUENCE: 75 gatgtcagt         9

<210> SEQ ID NO 76
<211> LENGTH: 36
<212> TYPE: DNA
<213> ORGANISM: Homo sapiens

<400> SEQUENCE: 76
tgctcatatg caggcggcaa ttttttctct tatgtc         36

<210> SEQ ID NO 77
<211> LENGTH: 125
<212> TYPE: PRT
<213> ORGANISM: Homo sapiens

<400> SEQUENCE: 77

Gln Ile Thr Leu Arg Glu Ser Gly Pro Thr Leu Val Lys Pro Thr Gln
1               5                   10                  15

Thr Leu Thr Leu Thr Cys Thr Phe Ser Gly Phe Ser Leu Asn Thr Asn
            20                  25                  30

Gly Val Gly Val Gly Trp Ile Arg Gln Pro Pro Gly Lys Ala Leu Glu
        35                  40                  45

Trp Leu Ala Leu Ile Tyr Trp Asn Gly Asn Glu Gly Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Val His Trp Pro Gln Gly Leu Thr Thr Val Thr Arg Leu Ala Phe
            100                 105                 110

Asp Ile Trp Gly Gln Gly Thr Met Val Thr Val Ser Ser
        115                 120                 125

<210> SEQ ID NO 78
<211> LENGTH: 112
<212> TYPE: PRT
<213> ORGANISM: Homo sapiens

<400> SEQUENCE: 78

Gln Ser Ala Leu Thr Gln Pro Arg Ser Val Ser Gly Ser Pro Gly Gln
1               5                   10                  15

Ser Val Thr Ile Ser Cys Thr Gly Thr Thr Ser Asp Val Gly Arg Tyr
            20                  25                  30

Asn Phe Val Ser Trp Tyr Gln Gln His Pro Gly Lys Ala Pro Lys Leu
        35                  40                  45

Leu Met Tyr Asp Val Ser Gln Arg Pro Ser Gly Val Pro Ser Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Val Phe Tyr Cys Cys Ser Tyr Ala Gly Gly
                85                  90                  95

Asn Phe Phe Ser Tyr Val Phe Gly Thr Gly Thr Lys Val Thr Val Leu
            100                 105                 110

<210> SEQ ID NO 79
<211> LENGTH: 376
<212> TYPE: DNA
<213> ORGANISM: Homo sapiens

<400> SEQUENCE: 79

```
cagatcacct tgagggagtc tggtcctacg ctggtgaaac ccacacagac cctcacgctg      60
acctgcacct tctctggctt ctcactcaac actaatggag tgggtgtggg ctggatccgt     120
cagcccccag gaaaggccct ggagtggctt gcactcattt actggaatgg taatgagggc     180
tacagcccct ctctgaaaag cagactcacc atcaccaagg acacctccaa aaaccaggtg     240
gtcctgacaa tgaccaacat ggaccctgtg acacagcca catattactg tgtacactgg      300
ccccaagggt tgactacggt gacaagactt gcttttgata tctggggcca agggactatg     360
gtcaccgtct cttcag                                                     376
```

<210> SEQ ID NO 80
<211> LENGTH: 337
<212> TYPE: DNA
<213> ORGANISM: Homo sapiens

<400> SEQUENCE: 80

```
cagtctgccc tgactcagcc tcgctcagtg tccgggtctc ctggacagtc agtcaccatc      60
tcctgcactg gaaccaccag tgatgttggt cgttataact ttgtctcctg gtaccaacaa     120
cacccaggca aagcccccaa actcctgatg tatgatgtca gtcagcggcc ctcaggggtc     180
cctagtcgct tctctggctc caagtctggc aacacggcct ccctgaccat ctctgggctc     240
caggctgagg atgaggctgt tttttactgc tgctcatatg caggcggcaa ttttttctct     300
tatgtcttcg gaactgggac caaggtcacc gtcctag                              337
```

<210> SEQ ID NO 81
<211> LENGTH: 8
<212> TYPE: PRT
<213> ORGANISM: Homo sapiens

<400> SEQUENCE: 81

Gly Gly Ser Ile Arg Ser Tyr Tyr
1               5

<210> SEQ ID NO 82

<211> LENGTH: 7
<212> TYPE: PRT
<213> ORGANISM: Homo sapiens

<400> SEQUENCE: 82

Ile Tyr Tyr Ser Gly Asn Thr
1               5

<210> SEQ ID NO 83
<211> LENGTH: 14
<212> TYPE: PRT
<213> ORGANISM: Homo sapiens

<400> SEQUENCE: 83

Ala Arg His Asp Val Ile Val Val Arg Gly Val Phe Asp Val
1               5                   10

<210> SEQ ID NO 84
<211> LENGTH: 9
<212> TYPE: PRT
<213> ORGANISM: Homo sapiens

<400> SEQUENCE: 84

Ser Ser Asp Ile Gly Thr Tyr Asn Leu
1               5

<210> SEQ ID NO 85
<211> LENGTH: 3
<212> TYPE: PRT
<213> ORGANISM: Homo sapiens

<400> SEQUENCE: 85

Asp Gly Ser
1

<210> SEQ ID NO 86
<211> LENGTH: 12
<212> TYPE: PRT
<213> ORGANISM: Homo sapiens

<400> SEQUENCE: 86

Cys Ser Tyr Ala Gly Thr Ser Asp Phe Phe Val Val
1               5                   10

<210> SEQ ID NO 87
<211> LENGTH: 24
<212> TYPE: DNA
<213> ORGANISM: Homo sapiens

<400> SEQUENCE: 87
ggtggctcca tccggagtta ctac                                          24

<210> SEQ ID NO 88
<211> LENGTH: 21
<212> TYPE: DNA
<213> ORGANISM: Homo sapiens

<400> SEQUENCE: 88
atctattaca gtgggaacac c                                             21

<210> SEQ ID NO 89
<211> LENGTH: 42
<212> TYPE: DNA
<213> ORGANISM: Homo sapiens

<400> SEQUENCE: 89
gcgagacatg atgtgatagt agtccgcggt gtctttgatg tc					42

<210> SEQ ID NO 90
<211> LENGTH: 27
<212> TYPE: DNA
<213> ORGANISM: Homo sapiens

<400> SEQUENCE: 90
agcagtgata ttggaactta taacctt					27

<210> SEQ ID NO 91
<211> LENGTH: 9
<212> TYPE: DNA
<213> ORGANISM: Homo sapiens

<400> SEQUENCE: 91 gatggcagt					9

<210> SEQ ID NO 92
<211> LENGTH: 36
<212> TYPE: DNA
<213> ORGANISM: Homo sapiens

<400> SEQUENCE: 92
tgctcatatg ctggtactag cgatttcttt gtggtt					36

<210> SEQ ID NO 93
<211> LENGTH: 120
<212> TYPE: PRT
<213> ORGANISM: Homo sapiens

<400> SEQUENCE: 93

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Arg Ser Tyr
            20                  25                  30

Tyr Trp Ser Trp Ile Arg Gln Pro Pro Gly Lys Gly Leu Glu Trp Ile
        35                  40                  45

Gly His Ile Tyr Tyr Ser Gly Asn Thr Asn Tyr Ser Pro Ser Leu Gln
    50                  55                  60

Ser Arg Val Thr Ile Ser Leu Asp Thr Pro Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg His Asp Val Ile Val Val Arg Gly Val Phe Asp Val Trp Gly Gln
            100                 105                 110

Gly Thr Val Val Thr Val Ser Ser
        115                 120

<210> SEQ ID NO 94
<211> LENGTH: 112
<212> TYPE: PRT
<213> ORGANISM: Homo sapiens

<400> SEQUENCE: 94

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Ile Gly Thr Tyr
            20                  25                  30

Asn Leu Val Ser Trp Tyr Gln Gln His Pro Gly Lys Ala Pro Lys Val
            35                  40                  45

Leu Ile Tyr Asp Gly Ser Lys Arg Pro Ser Gly Val Ser Ser Arg Phe
        50                  55                  60

Ser Ala Ser Lys Ser Gly Asn Thr Ala Ser Leu Thr Ile Ser Gly Leu
65                  70                  75                  80

Gln Ala Glu Asp Glu Thr Asp Tyr Tyr Cys Cys Ser Tyr Ala Gly Thr
                85                  90                  95

Ser Asp Phe Phe Val Val Phe Gly Gly Gly Thr Lys Leu Thr Val Leu
            100                 105                 110

```
<210> SEQ ID NO 95
<211> LENGTH: 361
<212> TYPE: DNA
<213> ORGANISM: Homo sapiens

<400> SEQUENCE: 95
caggtgcagc tgcaggagtc gggcccaggt ctggtgaagc cttcggagac cctgtccctc      60
acctgcactg tctctggtgg ctccatccgg agttactact ggagctggat ccggcagccc     120
ccagggaagg gactggagtg gattgggcac atctattaca gtgggaacac caactacagc     180
ccctccctcc agagtcgagt caccatatca ttagacacgc caagaaccca attctccctg     240
cggctgagct ctgtgaccgc cgcagacacg gccgtctatt actgtgcgag acatgatgtg     300
atagtagtcc gcggtgtctt tgatgtctgg ggccaaggga cagtggtcac cgtctcttca     360
g                                                                     361

<210> SEQ ID NO 96
<211> LENGTH: 337
<212> TYPE: DNA
<213> ORGANISM: Homo sapiens

<400> SEQUENCE: 96
cagtctgccc tgactcagcc tgcctccgtg tctgggtcac ctggacagtc gatcaccatc      60
tcctgcactg gaaccagcag tgatattgga acttataacc ttgtctcctg gtaccaacaa     120
cacccaggca aagcccccaa agtcctaatt tatgatggca gtaagcggcc ctcagggggtt    180 tctagtcgct tctctgcctc caagtctggc aacacggcct ccctgacaat ctctgggctc     240
caggctgagg acgagactga ttattactgc tgctcatatg ctggtactag cgatttcttt     300
gtggttttcg gcggagggac caagctgacc gtcctgg                              337

<210> SEQ ID NO 97
<211> LENGTH: 8
<212> TYPE: PRT
<213> ORGANISM: Homo sapiens

<400> SEQUENCE: 97
```

Gly Asp Thr Phe Pro Ala Tyr Trp
1               5

```
<210> SEQ ID NO 98
<211> LENGTH: 8
<212> TYPE: PRT
<213> ORGANISM: Homo sapiens

<400> SEQUENCE: 98
```

Ile Tyr Pro Ile Asp Ser Glu Thr
1               5

<210> SEQ ID NO 99
<211> LENGTH: 14
<212> TYPE: PRT
<213> ORGANISM: Homo sapiens

<400> SEQUENCE: 99

Ala Arg Gly Thr Ser Thr Gly Leu Arg Glu Ala Phe His Ile
1               5                   10

<210> SEQ ID NO 100
<211> LENGTH: 11
<212> TYPE: PRT
<213> ORGANISM: Homo sapiens

<400> SEQUENCE: 100

Gln Ser Leu Gly Tyr Ser Asp Gly Asn Thr Tyr
1               5                   10

<210> SEQ ID NO 101
<211> LENGTH: 3
<212> TYPE: PRT
<213> ORGANISM: Homo sapiens

<400> SEQUENCE: 101

Glu Val Ser
1

<210> SEQ ID NO 102
<211> LENGTH: 11
<212> TYPE: PRT
<213> ORGANISM: Homo sapiens

<400> SEQUENCE: 102

Met Gln Gly Thr His Trp Pro Pro Met Cys Ser
1               5                   10

<210> SEQ ID NO 103
<211> LENGTH: 24
<212> TYPE: DNA
<213> ORGANISM: Homo sapiens

<400> SEQUENCE: 103
ggagacactt tccccgccta ctgg                                       24

<210> SEQ ID NO 104
<211> LENGTH: 24
<212> TYPE: DNA
<213> ORGANISM: Homo sapiens

<400> SEQUENCE: 104
atctatccta ttgactctga gacc                                       24

<210> SEQ ID NO 105
<211> LENGTH: 42
<212> TYPE: DNA
<213> ORGANISM: Homo sapiens

<400> SEQUENCE: 105
gcccggggga caagtactgg cctcagagag gcttttcata tc                   42

<210> SEQ ID NO 106
<211> LENGTH: 33
<212> TYPE: DNA

<213> ORGANISM: Homo sapiens

<400> SEQUENCE: 106
caaagcctcg gatacagtga tggaaacacc tat 33

<210> SEQ ID NO 107
<211> LENGTH: 9
<212> TYPE: DNA
<213> ORGANISM: Homo sapiens

<400> SEQUENCE: 107 gaggtttct 9

<210> SEQ ID NO 108
<211> LENGTH: 33
<212> TYPE: DNA
<213> ORGANISM: Homo sapiens

<400> SEQUENCE: 108
atgcaaggta cacactggcc tcccatgtgc agt 33

<210> SEQ ID NO 109
<211> LENGTH: 121
<212> TYPE: PRT
<213> ORGANISM: Homo sapiens

<400> SEQUENCE: 109

Glu Val Gln Leu Val Gln Ser Gly Ala Glu Val Lys Lys Pro Gly Glu
1               5                   10                  15

Ser Leu Lys Ile Ser Cys Arg Glu Ser Gly Asp Thr Phe Pro Ala Tyr
            20                  25                  30

Trp Ile Ala Trp Val Arg Gln Met Pro Gly Lys Gly Leu Glu Trp Met
        35                  40                  45

Gly Ile Ile Tyr Pro Ile Asp Ser Glu Thr Thr Tyr Ser Pro Ser Phe
    50                  55                  60

Gln Gly Gln Val Thr Ile Ser Ala Asp Lys Ser Ile Asn Thr Ala Tyr
65                  70                  75                  80

Leu Gln Trp Ser Ser Leu Lys Ala Ser Asp Ser Ala Ile Tyr Tyr Cys
                85                  90                  95

Ala Arg Gly Thr Ser Thr Gly Leu Arg Glu Ala Phe His Ile Trp Gly
            100                 105                 110

Gln Gly Thr Met Val Thr Val Ser Ser
        115                 120

<210> SEQ ID NO 110
<211> LENGTH: 114
<212> TYPE: PRT
<213> ORGANISM: Homo sapiens

<400> SEQUENCE: 110

Asp Val Val Met Thr Gln Ser Pro Leu Ser Leu Ala Val Thr Leu Gly
1               5                   10                  15

Gln Pro Ala Tyr Ile Ser Cys Arg Ser Ser Gln Ser Leu Gly Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Glu Val Ser Asn Arg Asp Ser Gly Val Pro
    50                  55                  60

Asp Arg Phe Ser Gly Ser Gly Ser Gly Thr Asp Phe Thr Leu Lys Ile

```
              65                  70                  75                  80
Ser Arg Val Glu Ala Glu Asp Val Gly Thr Tyr Tyr Cys Met Gln Gly
                    85                  90                  95

Thr His Trp Pro Pro Met Cys Ser Phe Gly Gln Gly Thr Lys Leu Glu
            100                 105                 110

Ile Lys

<210> SEQ ID NO 111
<211> LENGTH: 364
<212> TYPE: DNA
<213> ORGANISM: Homo sapiens

<400> SEQUENCE: 111
gaggtgcagc tggtgcagtc tggagcagag gtgaaaaagc ccggggagtc tctgaagatc    60
tcctgtaggg aatctggaga cacttttccc gcctactgga tcgcctgggt gcgccagatg   120
cccgggaaag gcctggagtg gatgggaatt atctatccta ttgactctga gaccacatat   180
agcccgtcct tccaaggcca ggtcaccatt tcagccgaca gtccatcaa caccgcctac    240 ctgcagtgga gcagcctgaa ggcctcggac tccgccattt attactgtgc cggggggaca   300
agtactggcc tcagagaggc ttttcatatc tggggccaag gacaatggt caccgtctct    360 tcag                                                                364

<210> SEQ ID NO 112
<211> LENGTH: 343
<212> TYPE: DNA
<213> ORGANISM: Homo sapiens

<400> SEQUENCE: 112
gatgttgtga tgactcagtc tccactctcc ctggccgtca cccttggaca gccggcctac    60
atctcctgca ggtcaagtca aagcctcgga tacagtgatg aaacaccta tttgaattgg   120 tttcagcaga gaccaggcca atctcccagg cgcctaattt atgaggtttc taaccgggac   180
tctggggtcc cagacagatt cagcggcagt gggtcgggca ctgatttcac actgaaaatc   240
agcagggtgg aggctgagga tgttgggact tattactgca tgcaaggtac acactggcct   300
cccatgtgca gttttggcca ggggaccaag ttggagatca aac                     343

<210> SEQ ID NO 113
<211> LENGTH: 8
<212> TYPE: PRT
<213> ORGANISM: Homo sapiens

<400> SEQUENCE: 113

Gly Phe Thr Phe Ser Asn Tyr Gly
1               5

<210> SEQ ID NO 114
<211> LENGTH: 8
<212> TYPE: PRT
<213> ORGANISM: Homo sapiens

<400> SEQUENCE: 114

Ile Trp Asn Asp Gly Ser Lys Lys
1               5

<210> SEQ ID NO 115
<211> LENGTH: 19
<212> TYPE: PRT
<213> ORGANISM: Homo sapiens
```

<400> SEQUENCE: 115

Ala Arg Asp Glu Gly Val Gln Met Val Phe Ala Met Pro Asp Tyr Gly
1               5                   10                  15

Met Asp Val

<210> SEQ ID NO 116
<211> LENGTH: 6
<212> TYPE: PRT
<213> ORGANISM: Homo sapiens

<400> SEQUENCE: 116

Lys Leu Gly Asp Lys Phe
1               5

<210> SEQ ID NO 117
<211> LENGTH: 3
<212> TYPE: PRT
<213> ORGANISM: Homo sapiens

<400> SEQUENCE: 117

Gln Asp Ser
1

<210> SEQ ID NO 118
<211> LENGTH: 11
<212> TYPE: PRT
<213> ORGANISM: Homo sapiens

<400> SEQUENCE: 118

Gln Ala Trp Asp Ser Ser Thr Ala His Tyr Val
1               5                   10

<210> SEQ ID NO 119
<211> LENGTH: 24
<212> TYPE: DNA
<213> ORGANISM: Homo sapiens

<400> SEQUENCE: 119
ggattcacct tcagtaatta tggc                                    24

<210> SEQ ID NO 120
<211> LENGTH: 24
<212> TYPE: DNA
<213> ORGANISM: Homo sapiens

<400> SEQUENCE: 120
atatggaatg atggaagtaa gaaa                                    24

<210> SEQ ID NO 121
<211> LENGTH: 57
<212> TYPE: DNA
<213> ORGANISM: Homo sapiens

<400> SEQUENCE: 121
gcgagagatg aaggtgtaca aatggtgttc gccatgcctg actacggtat ggacgtc    57

<210> SEQ ID NO 122
<211> LENGTH: 18
<212> TYPE: DNA
<213> ORGANISM: Homo sapiens

<400> SEQUENCE: 122

```
aaattggggg ataaattc                                                         18
```

<210> SEQ ID NO 123
<211> LENGTH: 9
<212> TYPE: DNA
<213> ORGANISM: Homo sapiens

<400> SEQUENCE: 123

```
caagattcc                                                                    9
```

<210> SEQ ID NO 124
<211> LENGTH: 33
<212> TYPE: DNA
<213> ORGANISM: Homo sapiens

<400> SEQUENCE: 124

```
caggcgtggg acagcagcac tgcccattat gtc                                        33
```

<210> SEQ ID NO 125
<211> LENGTH: 126
<212> TYPE: PRT
<213> ORGANISM: Homo sapiens

<400> SEQUENCE: 125

Gln Val Gln Leu Leu Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Val Ile Trp Asn Asp Gly Ser Lys Lys Tyr Tyr Ala Glu Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Arg Asp Glu Gly Val Gln Met Val Phe Ala Met Pro Asp Tyr Gly
            100                 105                 110

Met Asp Val Trp Gly Gln Gly Thr Thr Val Thr Val Ser Ser
        115                 120                 125

<210> SEQ ID NO 126
<211> LENGTH: 108
<212> TYPE: PRT
<213> ORGANISM: Homo sapiens

<400> SEQUENCE: 126

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Phe Ala
            20                  25                  30

Cys Trp Tyr Gln Gln Arg Pro Gly Gln Ser Pro Ile Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Arg Gly Thr Gln Ala Met
65                  70                  75                  80

Asp Glu Ala Asp Tyr Tyr Cys Gln Ala Trp Asp Ser Ser Thr Ala His
                85                  90                  95

Tyr Val Phe Gly Thr Gly Thr Lys Val Thr Val Leu
            100                 105

<210> SEQ ID NO 127
<211> LENGTH: 379
<212> TYPE: DNA
<213> ORGANISM: Homo sapiens

<400> SEQUENCE: 127
caggtgcagt tgctggagtc tgggggaggc gtggtccagc ctgggaggtc cctgagactc     60
tcctgtgcag cgtctggatt caccttcagt aattatggca tgcactgggt ccgccaggct    120
ccaggcaagg ggctggagtg gtggcagtt atatggaatg atggaagtaa gaaatattat    180
gcagagtccg tgaagggccg gttcaccatc tccagagaca attccaagaa cacagtatat    240
ctacaaatga acagcctgag agccgaggac acggctgtgt attactgtgc gagagatgaa    300
ggtgtacaaa tggtgttcgc catgcctgac tacggtatgg acgtctgggg ccaggggacc    360
acggtcaccg tctcctcag                                                 379

<210> SEQ ID NO 128
<211> LENGTH: 325
<212> TYPE: DNA
<213> ORGANISM: Homo sapiens

<400> SEQUENCE: 128
tcctatgaac tgactcagcc accctcagtg tccgtgtccc caggacagac agccagcatc     60
acttgctctg gagataaatt ggggataaa ttcgcttgct ggtatcagca gaggccaggc    120
cagtctccta tactggtcat ctatcaagat tccaagcggc cctcagggat ccctgagcga    180
ttctctggct ccaactctgg gaacacagcc actctgacca tccgcgggac ccaggctatg    240
gatgaggctg actattactg tcaggcgtgg gacagcagca ctgcccatta tgtcttcgga    300
actgggacca aggtcaccgt ccttg                                          325

<210> SEQ ID NO 129
<211> LENGTH: 8
<212> TYPE: PRT
<213> ORGANISM: Homo sapiens

<400> SEQUENCE: 129

Gly Phe Ser Phe Ser Asn Tyr Gly
1               5

<210> SEQ ID NO 130
<211> LENGTH: 8
<212> TYPE: PRT
<213> ORGANISM: Homo sapiens

<400> SEQUENCE: 130

Ile Pro Ser Asp Gly Asn Tyr Gln
1               5

<210> SEQ ID NO 131
<211> LENGTH: 10
<212> TYPE: PRT
<213> ORGANISM: Homo sapiens

<400> SEQUENCE: 131

Ala His Leu Gly Gly Gly Leu Phe Asp Phe
1               5                   10

```
<210> SEQ ID NO 132
<211> LENGTH: 9
<212> TYPE: PRT
<213> ORGANISM: Homo sapiens

<400> SEQUENCE: 132

Ser Ser Asp Val Gly Gly Tyr Glu Phe
1               5

<210> SEQ ID NO 133
<211> LENGTH: 3
<212> TYPE: PRT
<213> ORGANISM: Homo sapiens

<400> SEQUENCE: 133

Asp Val Asp
1

<210> SEQ ID NO 134
<211> LENGTH: 8
<212> TYPE: PRT
<213> ORGANISM: Homo sapiens

<400> SEQUENCE: 134

Tyr Ser Ser Ala Asp Thr Trp Val
1               5

<210> SEQ ID NO 135
<211> LENGTH: 24
<212> TYPE: DNA
<213> ORGANISM: Homo sapiens

<400> SEQUENCE: 135
ggattctcct tcagtaatta tggc                                      24

<210> SEQ ID NO 136
<211> LENGTH: 24
<212> TYPE: DNA
<213> ORGANISM: Homo sapiens

<400> SEQUENCE: 136
ataccgtctg atggaaatta tcaa                                      24

<210> SEQ ID NO 137
<211> LENGTH: 30
<212> TYPE: DNA
<213> ORGANISM: Homo sapiens

<400> SEQUENCE: 137
gcccacctcg gggggggttt atttgacttc                                30

<210> SEQ ID NO 138
<211> LENGTH: 27
<212> TYPE: DNA
<213> ORGANISM: Homo sapiens

<400> SEQUENCE: 138
agcagtgatg ttggtggtta tgagttt                                   27

<210> SEQ ID NO 139
<211> LENGTH: 9
<212> TYPE: DNA
<213> ORGANISM: Homo sapiens
```

<400> SEQUENCE: 139 gatgtcgat                                                                                        9

<210> SEQ ID NO 140
<211> LENGTH: 24
<212> TYPE: DNA
<213> ORGANISM: Homo sapiens

<400> SEQUENCE: 140
tactcatctg cagacacctg ggtc                                                                      24

<210> SEQ ID NO 141
<211> LENGTH: 117
<212> TYPE: PRT
<213> ORGANISM: Homo sapiens

<400> SEQUENCE: 141

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Ser Phe Ser Asn Tyr
            20                  25                  30

Gly Met His Trp Val Arg Gln Ala Pro Gly Lys Gly Leu Glu Trp Val
        35                  40                  45

Ala Leu Ile Pro Ser Asp Gly Asn Tyr Gln Tyr Tyr Thr Asp Ser Val
    50                  55                  60

Lys Gly Arg Phe Thr Val Ser Arg Asp Asn Ser Arg Asn Thr Leu Tyr
65                  70                  75                  80

Leu Gln Met Lys Ser Leu Arg Ala Glu Asp Thr Ala Arg Tyr His Cys
                85                  90                  95

Ala His Leu Gly Gly Gly Leu Phe Asp Phe Trp Gly Gln Gly Thr Leu
            100                 105                 110

Val Thr Val Ser Ser
        115

<210> SEQ ID NO 142
<211> LENGTH: 108
<212> TYPE: PRT
<213> ORGANISM: Homo sapiens

<400> SEQUENCE: 142

Gln Ser Ala Leu Asn Gln Pro Arg Ser Val Ser Gly Ser Pro Gly Gln
1               5                   10                  15

Ser Val Ser Ile Ser Cys Thr Gly Ser Ser Ser Asp Val Gly Gly Tyr
            20                  25                  30

Glu Phe Val Ser Trp Tyr Gln His His Pro Gly Lys Ala Pro Lys Leu
        35                  40                  45

Ile Ile Tyr Asp Val Asp Lys Arg Pro Ser Gly Val Pro Asp Arg Phe
    50                  55                  60

Ser Gly Ser Arg Ser Gly Asp Thr Ala Ser Leu Thr Ile Ser Gly Leu
65                  70                  75                  80

Gln Ala Glu Asp Glu Ala Asp Tyr Tyr Cys Tyr Ser Ser Ala Asp Thr
                85                  90                  95

Trp Val Phe Gly Gly Gly Thr Lys Leu Thr Val Leu
            100                 105

<210> SEQ ID NO 143
<211> LENGTH: 352
<212> TYPE: DNA

<213> ORGANISM: Homo sapiens

<400> SEQUENCE: 143

```
caggtgcagc tggtggagtc tgggggaggc gtggtccagc ctggggggtc cctgagattg      60
tcctgtgcag cgtctggatt ctccttcagt aattatggca tgcactgggt ccgccaggct     120
ccaggcaagg ggctggagtg ggtggcactt ataccgtctg atggaaatta caatactat      180
acagactccg tgaagggccg attcaccgtc tccagagaca attccaggaa cacgttgtat     240
ctgcaaatga agagcctgag agctgaggac acggctagat atcattgtgc ccacctcggg     300
gggggtttat ttgacttctg ggccagggc accctggtca ccgtctcctc ag              352
```

<210> SEQ ID NO 144
<211> LENGTH: 325
<212> TYPE: DNA
<213> ORGANISM: Homo sapiens

<400> SEQUENCE: 144

```
cagtctgccc tgaatcagcc tcgctcagtg tccgggtctc ctggacagtc agtctccatc      60
tcctgcactg gctccagcag tgatgttggt ggttatgagt ttgtctcctg gtaccaacac     120
cacccaggca aagcccccaa actcataatt tatgatgtcg ataagcggcc ctcaggggtc     180
cctgatcgct tctctggctc caggtctggc gacacggcct ccctgaccat ctctgggctc     240
caggctgagg atgaggctga ttattactgc tactcatctg cagacacctg ggtcttcggc     300
ggagggacca agctcactgt cctag                                            325
```

<210> SEQ ID NO 145
<211> LENGTH: 8
<212> TYPE: PRT
<213> ORGANISM: Homo sapiens

<400> SEQUENCE: 145

Gly Gly Phe Thr Ser Ser Tyr Tyr
1               5

<210> SEQ ID NO 146
<211> LENGTH: 7
<212> TYPE: PRT
<213> ORGANISM: Homo sapiens

<400> SEQUENCE: 146

Val Tyr Tyr Gly Glu Ser Thr
1               5

<210> SEQ ID NO 147
<211> LENGTH: 11
<212> TYPE: PRT
<213> ORGANISM: Homo sapiens

<400> SEQUENCE: 147

Ala Arg Glu Val Asp Lys Arg Gly Phe Asp Tyr
1               5                   10

<210> SEQ ID NO 148
<211> LENGTH: 7
<212> TYPE: PRT
<213> ORGANISM: Homo sapiens

<400> SEQUENCE: 148

Gln Ser Val Ser Gly Gly Tyr
1               5

```
<210> SEQ ID NO 149
<211> LENGTH: 3
<212> TYPE: PRT
<213> ORGANISM: Homo sapiens

<400> SEQUENCE: 149

Gly Ala Ser
1

<210> SEQ ID NO 150
<211> LENGTH: 9
<212> TYPE: PRT
<213> ORGANISM: Homo sapiens

<400> SEQUENCE: 150

Gln Gln Tyr Gly Arg Thr Pro Leu Thr
1               5

<210> SEQ ID NO 151
<211> LENGTH: 24
<212> TYPE: DNA
<213> ORGANISM: Homo sapiens

<400> SEQUENCE: 151
ggtggcttca ccagtagtta ttat                                      24

<210> SEQ ID NO 152
<211> LENGTH: 21
<212> TYPE: DNA
<213> ORGANISM: Homo sapiens

<400> SEQUENCE: 152
gtgtattacg gtgaaagtac c                                         21

<210> SEQ ID NO 153
<211> LENGTH: 33
<212> TYPE: DNA
<213> ORGANISM: Homo sapiens

<400> SEQUENCE: 153
gcgagagaag tggataaacg gggctttgac tac                            33

<210> SEQ ID NO 154
<211> LENGTH: 21
<212> TYPE: DNA
<213> ORGANISM: Homo sapiens

<400> SEQUENCE: 154
cagagtgtta gcggcggtta c                                         21

<210> SEQ ID NO 155
<211> LENGTH: 9
<212> TYPE: DNA
<213> ORGANISM: Homo sapiens

<400> SEQUENCE: 155 ggtgcatcc                                                        9

<210> SEQ ID NO 156
<211> LENGTH: 27
<212> TYPE: DNA
<213> ORGANISM: Homo sapiens
```

<400> SEQUENCE: 156
cagcagtatg gtaggacacc gctcact                                          27

<210> SEQ ID NO 157
<211> LENGTH: 117
<212> TYPE: PRT
<213> ORGANISM: Homo sapiens

<400> SEQUENCE: 157

Gln Val Gln Leu Gln Glu Ser Gly Pro Gly Leu Val Lys Pro Ser Glu
1               5                   10                  15

Thr Leu Ser Leu Thr Cys Ser Val Ser Gly Gly Phe Thr Ser Ser Tyr
            20                  25                  30

Tyr Trp Ser Trp Ile Arg Gln Ala Pro Gly Lys Gly Leu Glu Trp Ile
        35                  40                  45

Gly Tyr Val Tyr Tyr Gly Glu Ser Thr Asp Tyr Asn Pro Ser Leu Lys
    50                  55                  60

Ser Arg Ala Thr Ile Ser Ile Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Val Asp Lys Arg Gly Phe Asp Tyr Trp Gly Gln Gly Ala Leu
            100                 105                 110

Val Thr Val Ser Ser
        115

<210> SEQ ID NO 158
<211> LENGTH: 108
<212> TYPE: PRT
<213> ORGANISM: Homo sapiens

<400> SEQUENCE: 158

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Gly Gly
            20                  25                  30

Tyr Leu Ala Trp Tyr Gln Gln Glu Pro Gly Gln Ala Pro Arg Leu Val
        35                  40                  45

Ile Tyr Gly Ala Ser Ser Arg Ala Thr Gly Ile Pro Asp Arg Phe Ser
    50                  55                  60

Ala Ser Gly Ser Gly Thr Asp Phe Thr Leu Thr Ile Thr Arg Leu Glu
65                  70                  75                  80

Pro Glu Asp Phe Ala Val Tyr Tyr Cys Gln Gln Tyr Gly Arg Thr Pro
                85                  90                  95

Leu Thr Phe Gly Gly Gly Thr Lys Val Glu Ile Lys
            100                 105

<210> SEQ ID NO 159
<211> LENGTH: 352
<212> TYPE: DNA
<213> ORGANISM: Homo sapiens

<400> SEQUENCE: 159
caggtgcagc tgcaggagtc gggcccagga ctggtgaagc cttcggagac cctgtccctc      60
acctgcagtg tctctggtgg cttcaccagt agtyattatt ggagttggat ccggcaggcc     120
cccgggaagg gactggagtg gattggctat gtgtattacg gtgaaagtac cgattacaac     180

```
ccctccctca agagtcgagc caccatatca atagacacgt ccaagaacca attctccctg      240
aagctgagct ctgtgaccgc tgcggacacg gccgtctatt attgtgcgag agaagtggat      300
aaacggggct tgactactg gggccaggga gccctggtca ccgtctcctc ag               352

<210> SEQ ID NO 160
<211> LENGTH: 325
<212> TYPE: DNA
<213> ORGANISM: Homo sapiens

<400> SEQUENCE: 160
gaaattgtgt tgacgcagtc tccaggcacc ctatctttgt ctccagggga aagagccacc       60
ctctcctgca gggccagtca gagtgttagc ggcggttact tagcctggta ccagcaggaa      120
cctggccagg ctcccaggct cgtcatctat ggtgcatcca gcagggccac tggcatccca      180
gacaggttca gtgccagtgg gtctgggaca gacttcactc tcaccatcac cagactggag      240
ccagaagatt ttgcagtgta ttactgtcag cagtatggta ggacaccgct cactttcggc      300
ggagggacca aggtggagat caaac                                            325

<210> SEQ ID NO 161
<211> LENGTH: 8
<212> TYPE: PRT
<213> ORGANISM: Homo sapiens

<400> SEQUENCE: 161

Ile Ser Tyr Asp Ala Ser Ser Lys
1               5

<210> SEQ ID NO 162
<211> LENGTH: 17
<212> TYPE: PRT
<213> ORGANISM: Homo sapiens

<400> SEQUENCE: 162

Ala Lys Ala Leu Arg Tyr Leu Asp Trp Phe Leu Ser Asp Pro Phe Asp
1               5                   10                  15

Tyr

<210> SEQ ID NO 163
<211> LENGTH: 7
<212> TYPE: PRT
<213> ORGANISM: Homo sapiens

<400> SEQUENCE: 163

Gln Ser Val Ser Ser Asp Phe
1               5

<210> SEQ ID NO 164
<211> LENGTH: 8
<212> TYPE: PRT
<213> ORGANISM: Homo sapiens

<400> SEQUENCE: 164

Gln Gln Tyr Ala Ala Ser Pro Pro
1               5

<210> SEQ ID NO 165
<211> LENGTH: 24
<212> TYPE: DNA
<213> ORGANISM: Homo sapiens

<400> SEQUENCE: 165
```

```
ggattcacct tcagtaacta tggc                                          24

<210> SEQ ID NO 166
<211> LENGTH: 24
<212> TYPE: DNA
<213> ORGANISM: Homo sapiens

<400> SEQUENCE: 166
atatcttatg atgcaagtag taaa                                          24

<210> SEQ ID NO 167
<211> LENGTH: 51
<212> TYPE: DNA
<213> ORGANISM: Homo sapiens

<400> SEQUENCE: 167
gcgaaagccc tacgatatct tgactggttc ctctcggacc ccttcgacta c            51

<210> SEQ ID NO 168
<211> LENGTH: 21
<212> TYPE: DNA
<213> ORGANISM: Homo sapiens

<400> SEQUENCE: 168
cagagtgtta gtagcgactt c                                             21

<210> SEQ ID NO 169
<211> LENGTH: 24
<212> TYPE: DNA
<213> ORGANISM: Homo sapiens

<400> SEQUENCE: 169
cagcagtatg ctgcctcacc gccc                                          24

<210> SEQ ID NO 170
<211> LENGTH: 124
<212> TYPE: PRT
<213> ORGANISM: Homo sapiens

<400> SEQUENCE: 170

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Gly Pro Gly Lys Gly Leu Glu Trp Val
        35                  40                  45

Ala Val Ile Ser Tyr Asp Ala Ser Ser Lys Tyr Tyr Thr Asp Ser Val
    50                  55                  60

Gln Gly Arg Phe Thr Ile Ser Arg Asp Asn Ser Lys Asn Thr Leu Phe
65                  70                  75                  80

Leu Gln Met Asn Ser Leu Arg Gly Glu Asp Thr Ala Val Tyr Tyr Cys
                85                  90                  95

Ala Lys Ala Leu Arg Tyr Leu Asp Trp Phe Leu Ser Asp Pro Phe Asp
            100                 105                 110

Tyr Trp Gly Gln Gly Thr Leu Val Thr Val Ser Ser
        115                 120

<210> SEQ ID NO 171
<211> LENGTH: 107
<212> TYPE: PRT
```

<213> ORGANISM: Homo sapiens

<400> SEQUENCE: 171

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asp
            20                  25                  30

Phe Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ala Ala Ser Pro
                85                  90                  95

Pro Phe Gly Gln Gly Thr Arg Leu Glu Ile Lys
            100                 105

<210> SEQ ID NO 172
<211> LENGTH: 373
<212> TYPE: DNA
<213> ORGANISM: Homo sapiens

<400> SEQUENCE: 172
caggtgcaac tggtggagtc tgggggaggc gtggtccagc ctggagggtc cctcagactc      60
tcctgtgcag cctctggatt caccttcagt aactatggca tgcactgggt ccgccagggt     120
ccaggcaagg ggctggagtg ggtggcagtt atatcttatg atgcaagtag taaatactat     180
acagactccg tgcagggccg attcaccatc tccagagaca attccaagaa cacactgttt     240
ctgcaaatga acagcctgag aggtgaagac acggctgtgt attactgtgc gaaagcccta     300
cgatatcttg actggttcct ctcggacccc ttcgactact ggggccaggg aaccctggtc     360
accgtctcct cag                                                        373

<210> SEQ ID NO 173
<211> LENGTH: 322
<212> TYPE: DNA
<213> ORGANISM: Homo sapiens

<400> SEQUENCE: 173
gaaattgtgt tgacgcagtc tccaggcacc ctgtctttgt ctccagggga aagagccacc      60
ctctcctgca gggccagtca gagtgttagt agcgacttct tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag ccgactggag     240
cctgaagatt ttgcagtcta ttactgtcag cagtatgctg cctcaccgcc cttcggccaa     300
gggacacgac tggagattaa ac                                              322

<210> SEQ ID NO 174
<211> LENGTH: 8
<212> TYPE: PRT
<213> ORGANISM: Homo sapiens

<400> SEQUENCE: 174

Gly Phe Thr Phe Ser Ser Asp Gly
1               5

```
<210> SEQ ID NO 175
<211> LENGTH: 8
<212> TYPE: PRT
<213> ORGANISM: Homo sapiens

<400> SEQUENCE: 175

Ile Ser Ser Asp Gly Ser Thr Pro
1               5

<210> SEQ ID NO 176
<211> LENGTH: 15
<212> TYPE: PRT
<213> ORGANISM: Homo sapiens

<400> SEQUENCE: 176

Ala Lys Asp Trp Ala Leu Phe Arg Trp Leu Arg Thr Phe Asp His
1               5                   10                  15

<210> SEQ ID NO 177
<211> LENGTH: 6
<212> TYPE: PRT
<213> ORGANISM: Homo sapiens

<400> SEQUENCE: 177

Gln Ser Val Gly Ile Asn
1               5

<210> SEQ ID NO 178
<211> LENGTH: 10
<212> TYPE: PRT
<213> ORGANISM: Homo sapiens

<400> SEQUENCE: 178

Gln Gln Tyr Asn Asp Trp Pro Pro Trp Thr
1               5                   10

<210> SEQ ID NO 179
<211> LENGTH: 24
<212> TYPE: DNA
<213> ORGANISM: Homo sapiens

<400> SEQUENCE: 179
ggattcacct tcagtagcga cggc                                          24

<210> SEQ ID NO 180
<211> LENGTH: 24
<212> TYPE: DNA
<213> ORGANISM: Homo sapiens

<400> SEQUENCE: 180
atatcatctg acggaagtac tcca                                          24

<210> SEQ ID NO 181
<211> LENGTH: 45
<212> TYPE: DNA
<213> ORGANISM: Homo sapiens

<400> SEQUENCE: 181
gccaaagatt gggcattatt tcggtggcta cgaacctttg atcat                   45

<210> SEQ ID NO 182
<211> LENGTH: 18
<212> TYPE: DNA
<213> ORGANISM: Homo sapiens
```

```
<400> SEQUENCE: 182
cagagtgttg gcatcaat                                                18

<210> SEQ ID NO 183
<211> LENGTH: 30
<212> TYPE: DNA
<213> ORGANISM: Homo sapiens

<400> SEQUENCE: 183
caacaatata atgactggcc tccgtggacg                                   30

<210> SEQ ID NO 184
<211> LENGTH: 122
<212> TYPE: PRT
<213> ORGANISM: Homo sapiens

<400> SEQUENCE: 184
```

Leu Val Glu Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Asp
            20                  25                  30

Gly Met His Trp Val Arg Gln Ser Pro Gly Arg Gly Leu Glu Trp Val
        35                  40                  45

Ala Phe Ile Ser Ser Asp Gly Ser Thr Pro Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Met Tyr Phe Cys
                85                  90                  95

Ala Lys Asp Trp Ala Leu Phe Arg Trp Leu Arg Thr Phe Asp His Trp
            100                 105                 110

Gly Gln Gly Thr Leu Val Thr Val Ser Ser
        115                 120

```
<210> SEQ ID NO 185
<211> LENGTH: 108
<212> TYPE: PRT
<213> ORGANISM: Homo sapiens

<400> SEQUENCE: 185
```

Glu Thr Val Met Thr Gln Ser Pro Ala Thr Leu Ser Val Ser Pro Gly
1               5                   10                  15

Gly Arg Ala Thr Leu Ser Cys Arg Ala Ser Gln Ser Val Gly Ile Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Ser Gly Phe Pro Ala Arg Phe Ser Gly
    50                  55                  60

Ser Gly Ser Gly Thr Glu Phe Thr Leu Thr Ile Thr Ser Leu Gln Ser
65                  70                  75                  80

Glu Asp Phe Ala Val Tyr Tyr Cys Gln Gln Tyr Asn Asp Trp Pro Pro
                85                  90                  95

Trp Thr Phe Gly Gln Gly Thr Lys Val Glu Ile Lys
            100                 105

```
<210> SEQ ID NO 186
<211> LENGTH: 367
<212> TYPE: DNA
```

<213> ORGANISM: Homo sapiens

<400> SEQUENCE: 186

```
ctggtggaac tggtggagtc tgggggaggc gtggtccagc ctgggaggtc cctgagactc    60
tcctgtgcag cctctggatt caccttcagt agcgacggca tgcactgggt ccgccagagt   120
ccaggcaggg ggctggaatg ggtggccttt atatcatctg acggaagtac tccatactat   180
gctgactccg tgaagggccg attcaccatc tccagagaca attccaagaa cacactgtat   240
ctgcaaatga acagcctcag agctgaggac acggctatgt acttctgtgc aaagattgg    300
gcattatttc ggtggctacg aacctttgat cattggggcc agggaaccct ggtcaccgtc   360
tcctcag                                                              367
```

<210> SEQ ID NO 187
<211> LENGTH: 325
<212> TYPE: DNA
<213> ORGANISM: Homo sapiens

<400> SEQUENCE: 187

```
gaaacggtga tgacgcagtc tccagccacc ctgtctgtgt ctcctggggg aagagccacc    60
ctctcctgca gggccagtca gagtgttggc atcaatttag cctggtacca gcagaaacct   120
ggccaggctc ccaggctcct catctatggt gcatccacca gggcctctgg tttcccagcc   180
aggttcagtg gcagtgggtc tgggacagag ttcactctca ccatcaccag cctgcagtct   240
gaagattttg cagtctatta ctgtcaacaa tataatgact ggcctccgtg acgttcggc    300
caagggacca aggtggagat caaac                                          325
```

<210> SEQ ID NO 188
<211> LENGTH: 8
<212> TYPE: PRT
<213> ORGANISM: Homo sapiens

<400> SEQUENCE: 188

Gly Tyr Ser Phe Thr Asn Tyr Trp
1               5

<210> SEQ ID NO 189
<211> LENGTH: 8
<212> TYPE: PRT
<213> ORGANISM: Homo sapiens

<400> SEQUENCE: 189

Ile Tyr Pro Gly Asp Ser Asp Ile
1               5

<210> SEQ ID NO 190
<211> LENGTH: 12
<212> TYPE: PRT
<213> ORGANISM: Homo sapiens

<400> SEQUENCE: 190

Ala Arg His Ala Ile Arg Gly Asp Gly Phe Asp Tyr
1               5                   10

<210> SEQ ID NO 191
<211> LENGTH: 6
<212> TYPE: PRT
<213> ORGANISM: Homo sapiens

<400> SEQUENCE: 191

```
Lys Leu Gly Glu Lys Tyr
1               5
```

<210> SEQ ID NO 192
<211> LENGTH: 3
<212> TYPE: PRT
<213> ORGANISM: Homo sapiens

<400> SEQUENCE: 192

```
Gln Asp Thr
1
```

<210> SEQ ID NO 193
<211> LENGTH: 9
<212> TYPE: PRT
<213> ORGANISM: Homo sapiens

<400> SEQUENCE: 193

```
Gln Ala Trp Asp Thr Asn Thr Val Ile
1               5
```

<210> SEQ ID NO 194
<211> LENGTH: 24
<212> TYPE: DNA
<213> ORGANISM: Homo sapiens

<400> SEQUENCE: 194
ggatacagct ttaccaacta ctgg                                    24

<210> SEQ ID NO 195
<211> LENGTH: 24
<212> TYPE: DNA
<213> ORGANISM: Homo sapiens

<400> SEQUENCE: 195
atctatcctg gtgactctga tatc                                    24

<210> SEQ ID NO 196
<211> LENGTH: 36
<212> TYPE: DNA
<213> ORGANISM: Homo sapiens

<400> SEQUENCE: 196
gcgagacatg caatacgagg agatgggttt gactac                        36

<210> SEQ ID NO 197
<211> LENGTH: 18
<212> TYPE: DNA
<213> ORGANISM: Homo sapiens

<400> SEQUENCE: 197
aaattggggg aaaaatac                                           18

<210> SEQ ID NO 198
<211> LENGTH: 9
<212> TYPE: DNA
<213> ORGANISM: Homo sapiens

<400> SEQUENCE: 198 caagatacg                                                     9

<210> SEQ ID NO 199
<211> LENGTH: 27
<212> TYPE: DNA

<213> ORGANISM: Homo sapiens

<400> SEQUENCE: 199
caggcgtggg acaccaacac tgtgata 27

<210> SEQ ID NO 200
<211> LENGTH: 119
<212> TYPE: PRT
<213> ORGANISM: Homo sapiens

<400> SEQUENCE: 200

Glu Val Gln Leu Val Gln Ser Gly Ala Glu Val Lys Lys Pro Gly Glu
1               5                   10                  15

Ser Leu Lys Ile Ser Cys Gln Ala Ser Gly Tyr Ser Phe Thr Asn Tyr
            20                  25                  30

Trp Ile Ala Trp Val Arg Gln Met Pro Gly Lys Gly Leu Glu Trp Met
        35                  40                  45

Gly Ile Ile Tyr Pro Gly Asp Ser Asp Ile Lys Tyr Ser Pro Ser Phe
    50                  55                  60

Arg Gly Gln Val Thr Ile Ser Ala Asp Lys Ser Ile Ser Asn Ala Phe
65                  70                  75                  80

Leu Gln Trp Arg Ser Leu Arg Ala Ser Asp Thr Ala Met Tyr Tyr Cys
                85                  90                  95

Ala Arg His Ala Ile Arg Gly Asp Gly Phe Asp Tyr Trp Gly Gln Gly
            100                 105                 110

Thr Leu Val Thr Val Ser Ser
        115

<210> SEQ ID NO 201
<211> LENGTH: 106
<212> TYPE: PRT
<213> ORGANISM: Homo sapiens

<400> SEQUENCE: 201

Ser Tyr Glu Leu Thr Gln Pro Pro Ser Val Ser Val Ser Pro Gly Gln
1               5                   10                  15

Thr Ala Thr Ile Thr Cys Ser Gly Asp Lys Leu Gly Glu Lys Tyr Ala
            20                  25                  30

Cys Trp Tyr Gln Gln Lys Pro Gly Gln Ser Pro Val Leu Val Met Tyr
        35                  40                  45

Gln Asp Thr Lys Arg Pro Ser Gly Ile Pro Glu Arg Phe Ser Gly Ser
    50                  55                  60

Asn Ser Gly Asn Thr Ala Thr Leu Thr Ile Ser Gly Thr Arg Ala Met
65                  70                  75                  80

Asp Glu Ala Asp Tyr Tyr Cys Gln Ala Trp Asp Thr Asn Thr Val Ile
                85                  90                  95

Phe Gly Gly Gly Thr Lys Leu Thr Val Leu
            100                 105

<210> SEQ ID NO 202
<211> LENGTH: 358
<212> TYPE: DNA
<213> ORGANISM: Homo sapiens

<400> SEQUENCE: 202
gaggtgcagc tggtgcagtc tggagcagaa gtgaaaaagc cggggagtc tctgaagatc      60 tcctgtcagg cttctggata cagctttacc aactactgga tcgcctgggt gcgccagatg    120

```
cccgggaaag gcctggagtg gatgggcatc atctatcctg gtgactctga tatcaaatac    180
agcccgtcct tccgaggcca ggtcaccatc tcagccgaca agtccatcag taatgccttc    240
ctccagtggc gaagcctgag ggcctcggac accgccatgt attactgtgc gagacatgca    300
atacgaggag atgggtttga ctactggggc cagggaaccc tggtcaccgt ctcctcag     358

<210> SEQ ID NO 203
<211> LENGTH: 319
<212> TYPE: DNA
<213> ORGANISM: Homo sapiens

<400> SEQUENCE: 203
tcctatgagc tgactcagcc accctcagtg tccgtgtccc caggacagac agccaccatc     60
acctgctctg gagataaatt gggggaaaaa tacgcttgct ggtatcagca gaagccaggc    120
cagtcccctg ttttggtcat gtatcaagat acgaagcggc cctcagggat ccctgagcga    180
ttctctggct ccaactctgg gaacacagcc actctgacca tcagcgggac ccgggctatg    240
gatgaagctg actattactg tcaggcgtgg gacaccaaca ctgtgatatt cggcggaggg    300
accaagctga ccgtcctag                                                319

<210> SEQ ID NO 204
<211> LENGTH: 8
<212> TYPE: PRT
<213> ORGANISM: Homo sapiens

<400> SEQUENCE: 204

Ile Tyr Pro Gly Asp Ser Asp Thr
1               5

<210> SEQ ID NO 205
<211> LENGTH: 12
<212> TYPE: PRT
<213> ORGANISM: Homo sapiens

<400> SEQUENCE: 205

Gly Arg His Ala Ile Arg Gly Asp Gly Phe Asp Tyr
1               5                   10

<210> SEQ ID NO 206
<211> LENGTH: 24
<212> TYPE: DNA
<213> ORGANISM: Homo sapiens

<400> SEQUENCE: 206
atctatcctg gtgactctga tacc                                           24

<210> SEQ ID NO 207
<211> LENGTH: 36
<212> TYPE: DNA
<213> ORGANISM: Homo sapiens

<400> SEQUENCE: 207
gggagacatg caatacgagg agatgggttt gactac                              36

<210> SEQ ID NO 208
<211> LENGTH: 119
<212> TYPE: PRT
<213> ORGANISM: Homo sapiens

<400> SEQUENCE: 208

Glu Val Gln Leu Val Gln Ser Gly Ala Glu Val Lys Lys Pro Gly Glu
```

```
            1               5                   10                  15
Ser Leu Lys Ile Ser Cys Gln Ala Ser Gly Tyr Ser Phe Thr Asn Tyr
            20                  25                  30

Trp Ile Ala Trp Val Arg Gln Met Pro Gly Lys Gly Leu Glu Trp Met
            35                  40                  45

Gly Ile Ile Tyr Pro Gly Asp Ser Asp Thr Lys Tyr Ser Pro Ser Phe
            50                  55                  60

Arg Gly Gln Val Thr Ile Ser Ala Asp Lys Ser Ile Ser Thr Ala Phe
65                  70                  75                  80

Leu Gln Trp Arg Ser Leu Arg Ala Ser Asp Thr Ala Met Tyr Tyr Cys
            85                  90                  95

Gly Arg His Ala Ile Arg Gly Asp Gly Phe Asp Tyr Trp Gly Gln Gly
            100                 105                 110

Thr Leu Val Thr Val Ser Ser
            115
```

<210> SEQ ID NO 209
<211> LENGTH: 358
<212> TYPE: DNA
<213> ORGANISM: Homo sapiens

<400> SEQUENCE: 209

```
gaggtgcagc tggtgcagtc tggagcagaa gtgaaaaagc ccggggagtc tctgaagatc    60
tcctgtcagg cttctggata cagctttacc aactactgga tcgcctgggt gcgccagatg   120
cccgggaaag cctggagtg atgggcatc atctatcctg gtgactctga taccaaatac    180
agcccgtcct tccgaggcca ggtcaccatc tcagccgaca gtccatcag tactgccttc    240
ctccagtggc gaagcctgag ggcctcggac accgccatgt attactgtgg agacatgca    300
atacgaggag atgggtttga ctactggggc cagggaaccc tggtcaccgt ctcctcag    358
```

<210> SEQ ID NO 210
<211> LENGTH: 12
<212> TYPE: PRT
<213> ORGANISM: Homo sapiens

<400> SEQUENCE: 210

```
Glu Arg His Ala Ile Arg Gly Asp Gly Phe Asp Tyr
1               5                   10
```

<210> SEQ ID NO 211
<211> LENGTH: 36
<212> TYPE: DNA
<213> ORGANISM: Homo sapiens

<400> SEQUENCE: 211

```
gagagacatg caatacgagg agatgggttt gactac                              36
```

<210> SEQ ID NO 212
<211> LENGTH: 119
<212> TYPE: PRT
<213> ORGANISM: Homo sapiens

<400> SEQUENCE: 212

```
Glu Val Gln Leu Val Gln Ser Gly Ala Glu Val Lys Lys Pro Gly Glu
1               5                   10                  15

Ser Leu Lys Ile Ser Cys Gln Ala Ser Gly Tyr Ser Phe Thr Asn Tyr
            20                  25                  30

Trp Ile Ala Trp Val Arg Gln Met Pro Gly Lys Gly Leu Glu Trp Met
```

```
                35                  40                  45
Gly Ile Ile Tyr Pro Gly Asp Ser Asp Thr Lys Tyr Ser Pro Ser Phe
         50                  55                  60
Arg Gly Gln Val Thr Ile Ser Ala Asp Lys Ser Ile Ser Thr Ala Phe
65                  70                  75                  80
Leu Gln Trp Arg Ser Leu Arg Ala Ser Asp Thr Ala Met Tyr Tyr Cys
                 85                  90                  95
Glu Arg His Ala Ile Arg Gly Asp Gly Phe Asp Tyr Trp Gly Gln Gly
            100                 105                 110
Thr Leu Val Thr Val Ser Ser
            115

<210> SEQ ID NO 213
<211> LENGTH: 106
<212> TYPE: PRT
<213> ORGANISM: Homo sapiens

<400> SEQUENCE: 213

Ser Tyr Val Leu Thr Gln Pro Pro Ser Val Ser Val Ser Pro Gly Gln
1               5                  10                  15
Thr Ala Thr Ile Thr Cys Ser Gly Asp Lys Leu Gly Glu Lys Tyr Ala
            20                  25                  30
Cys Trp Tyr Gln Gln Lys Pro Gly Gln Ser Pro Val Leu Val Met Tyr
         35                  40                  45
Gln Asp Thr Lys Arg Pro Ser Gly Ile Pro Glu Arg Phe Ser Gly Ser
     50                  55                  60
Asn Ser Gly Asn Thr Ala Thr Leu Thr Ile Ser Gly Thr Arg Ala Met
65                  70                  75                  80
Asp Glu Ala Asp Tyr Tyr Cys Gln Ala Trp Asp Thr Asn Thr Val Ile
                 85                  90                  95
Phe Gly Gly Gly Thr Lys Leu Thr Val Leu
            100                 105

<210> SEQ ID NO 214
<211> LENGTH: 358
<212> TYPE: DNA
<213> ORGANISM: Homo sapiens

<400> SEQUENCE: 214
gaggtgcagc tggtgcagtc tggagcagaa gtgaaaaagc cggggagtc tctgaagatc      60 tcctgtcagg cttctggata cagctttacc aactactgga tcgcctgggt gcgccagatg    120
cccgggaaag gcctggagtg gatgggcatc atctatcctg gtgactctga taccaaatac    180
agcccgtcct tccgaggcca ggtcaccatc tcagccgaca gtccatcag tactgccttc     240 ctccagtggc gaagcctgag ggcctcggac accgccatgt attactgtga gagacatgca    300
atacgaggag atgggtttga ctactggggc cagggaaccc tggtcaccgt ctcctcag      358

<210> SEQ ID NO 215
<211> LENGTH: 319
<212> TYPE: DNA
<213> ORGANISM: Homo sapiens

<400> SEQUENCE: 215
tcctatgtcc tgactcagcc accctcagtg tccgtgtccc caggacagac agccaccatc     60
acctgctctg gagataaaatt gggggaaaaa tacgcttgct ggtatcagca gaagccaggc   120 cagtccccctg ttttggtcat gtatcaagat acgaagcggc cctcagggat ccctgagcga   180
```

```
ttctctggct ccaactctgg gaacacagcc actctgacca tcagcgggac ccgggctatg    240
gatgaagctg actattactg tcaggcgtgg gacaccaaca ctgtgatatt cggcggaggg    300
accaagctga ccgtcctag                                                 319
```

<210> SEQ ID NO 216
<211> LENGTH: 8
<212> TYPE: PRT
<213> ORGANISM: Homo sapiens

<400> SEQUENCE: 216

Gly Tyr Thr Phe Thr Asn Tyr Tyr
1               5

<210> SEQ ID NO 217
<211> LENGTH: 8
<212> TYPE: PRT
<213> ORGANISM: Homo sapiens

<400> SEQUENCE: 217

Ile His Pro Ser Ser Gly Gly Thr
1               5

<210> SEQ ID NO 218
<211> LENGTH: 16
<212> TYPE: PRT
<213> ORGANISM: Homo sapiens

<400> SEQUENCE: 218

Gly Arg Ala Phe Arg Ile Leu Gly Leu Ser Asp Val Phe Val Asn Asp
1               5                   10                  15

<210> SEQ ID NO 219
<211> LENGTH: 6
<212> TYPE: PRT
<213> ORGANISM: Homo sapiens

<400> SEQUENCE: 219

Gln Gly Ile Asn Asn Tyr
1               5

<210> SEQ ID NO 220
<211> LENGTH: 3
<212> TYPE: PRT
<213> ORGANISM: Homo sapiens

<400> SEQUENCE: 220

Ala Ala Ser
1

<210> SEQ ID NO 221
<211> LENGTH: 9
<212> TYPE: PRT
<213> ORGANISM: Homo sapiens

<400> SEQUENCE: 221

Gln Lys Tyr Asn Ser Ala Pro Phe Thr
1               5

<210> SEQ ID NO 222
<211> LENGTH: 24
<212> TYPE: DNA
<213> ORGANISM: Homo sapiens -continued

<400> SEQUENCE: 222
ggatacacct tcaccaacta ctat                                          24

<210> SEQ ID NO 223
<211> LENGTH: 24
<212> TYPE: DNA
<213> ORGANISM: Homo sapiens

<400> SEQUENCE: 223 atccaccta gtagtggtgg caca                                           24

<210> SEQ ID NO 224
<211> LENGTH: 48
<212> TYPE: DNA
<213> ORGANISM: Homo sapiens

<400> SEQUENCE: 224
gggagagcct ttcggatctt gggactttcg gatgtctttg ttaatgac                48

<210> SEQ ID NO 225
<211> LENGTH: 18
<212> TYPE: DNA
<213> ORGANISM: Homo sapiens

<400> SEQUENCE: 225
cagggcatta acaattat                                                 18

<210> SEQ ID NO 226
<211> LENGTH: 9
<212> TYPE: DNA
<213> ORGANISM: Homo sapiens

<400> SEQUENCE: 226 gctgcatcc                                                            9

<210> SEQ ID NO 227
<211> LENGTH: 27
<212> TYPE: DNA
<213> ORGANISM: Homo sapiens

<400> SEQUENCE: 227
caaaagtata acagtgcccc cttcact                                       27

<210> SEQ ID NO 228
<211> LENGTH: 123
<212> TYPE: PRT
<213> ORGANISM: Homo sapiens

<400> SEQUENCE: 228

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Ile His Trp Val Arg Gln Ala Pro Gly Gln Gly Leu Glu Trp Met
        35                  40                  45

Gly Ile Ile His Pro Ser Ser Gly Gly Thr Ser Tyr Ala Gln Lys Phe
    50                  55                  60

Gln Gly Arg Val Thr Met Thr Arg Asp Thr Ser Thr Ser Thr Val Ser
65                  70                  75                  80

Met Asp Leu Ser Ser Leu Arg Ser Glu Asp Thr Ala Val Tyr Tyr Cys
                85                  90                  95

Gly Arg Ala Phe Arg Ile Leu Gly Leu Ser Asp Val Phe Val Asn Asp
            100                 105                 110

Trp Gly Gln Gly Thr Val Val Thr Val Ser Ser
        115                 120

<210> SEQ ID NO 229
<211> LENGTH: 107
<212> TYPE: PRT
<213> ORGANISM: Homo sapiens

<400> SEQUENCE: 229

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Asn Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Ala Phe Thr Leu Thr Ile Leu Ser Leu Gln Pro
65                  70                  75                  80

Glu Asp Val Ala Thr Tyr Tyr Cys Gln Lys Tyr Asn Ser Ala Pro Phe
                85                  90                  95

Thr Phe Gly Pro Gly Thr Lys Val Asp Ile Lys
            100                 105

<210> SEQ ID NO 230
<211> LENGTH: 370
<212> TYPE: DNA
<213> ORGANISM: Homo sapiens

<400> SEQUENCE: 230
caggtgcagt tggtgcagtc tggggctgag gtgaagaagc tggggcctc agtgaaggtt      60 tcctgcaagg catctggata caccttcacc aactactata tacactgggt gcgacaggcc     120
cctggacaag gacttgagtg gatgggaata atccacccta gtagtggtgg cacaagctac    180
gcacagaagt tccagggcag agtcaccatg accagggaca cgtccacgag cacagtttcc    240
atggacctga gcagcctgag atctgaagac acggccgtat attactgtgg gagagccttt    300
cggatcttgg gactttcgga tgtctttgtt aatgactggg gccagggaac tgtggtcacc    360
gtctcctcag                                                           370

<210> SEQ ID NO 231
<211> LENGTH: 322
<212> TYPE: DNA
<213> ORGANISM: Homo sapiens

<400> SEQUENCE: 231
gacatccaga tgacccagtc tccatcctcc ctgtctgcat ctgtaggaga cagagtcacc      60
atcacttgcc gggcgagtca gggcattaac aattatttag cctggtatca gcagaaacca    120
gggaaagttc ctaagctcct gatctatgct gcatccacat tgcaatcagg ggtcccatct    180
cggttcagtg gcagtggatc tgggacagct ttcaccctca ccatcctcag cctgcagcct    240
gaagatgttg caacttatta ctgtcaaaag tataacagtg ccccttcac tttcggccct    300 gggaccaaag tggacatcaa ac                                              322

<210> SEQ ID NO 232
<211> LENGTH: 8
<212> TYPE: PRT
<213> ORGANISM: Homo sapiens

<400> SEQUENCE: 232

Gly Phe Thr Phe Thr Ser Ser Ala
1               5

<210> SEQ ID NO 233
<211> LENGTH: 8
<212> TYPE: PRT
<213> ORGANISM: Homo sapiens

<400> SEQUENCE: 233

Ile Val Leu Gly Ser Gly Asn Thr
1               5

<210> SEQ ID NO 234
<211> LENGTH: 14
<212> TYPE: PRT
<213> ORGANISM: Homo sapiens

<400> SEQUENCE: 234

Ala Ala Asp Arg Gly Arg Gly Gly Tyr Asn Val Tyr Thr Tyr
1               5                   10

<210> SEQ ID NO 235
<211> LENGTH: 7
<212> TYPE: PRT
<213> ORGANISM: Homo sapiens

<400> SEQUENCE: 235

Gln Thr Ile Ser Asn Thr Tyr
1               5

<210> SEQ ID NO 236
<211> LENGTH: 9
<212> TYPE: PRT
<213> ORGANISM: Homo sapiens

<400> SEQUENCE: 236

Gln Gln Asn Gly Gln Ser Pro Trp Thr
1               5

<210> SEQ ID NO 237
<211> LENGTH: 24
<212> TYPE: DNA
<213> ORGANISM: Homo sapiens

<400> SEQUENCE: 237
ggattcacct ttactagctc tgct                                          24

<210> SEQ ID NO 238
<211> LENGTH: 24
<212> TYPE: DNA
<213> ORGANISM: Homo sapiens

<400> SEQUENCE: 238
atcgtccttg gcagcggtaa caca                                          24

<210> SEQ ID NO 239
<211> LENGTH: 42
<212> TYPE: DNA
<213> ORGANISM: Homo sapiens

<400> SEQUENCE: 239
gcggcagata ggggtagagg tggatacaat gtatacactt ac                              42

<210> SEQ ID NO 240
<211> LENGTH: 21
<212> TYPE: DNA
<213> ORGANISM: Homo sapiens

<400> SEQUENCE: 240
cagactatta gtaacaccta c                                                     21

<210> SEQ ID NO 241
<211> LENGTH: 27
<212> TYPE: DNA
<213> ORGANISM: Homo sapiens

<400> SEQUENCE: 241
cagcagaatg gtcagtcacc ttggacg                                               27

<210> SEQ ID NO 242
<211> LENGTH: 121
<212> TYPE: PRT
<213> ORGANISM: Homo sapiens

<400> SEQUENCE: 242

Gln Met Gln Leu Val Gln Ser Gly Pro Gln Val Lys Lys Pro Gly Thr
1               5                   10                  15

Ser Val Lys Val Ser Cys Lys Ala Ser Gly Phe Thr Phe Thr Ser Ser
            20                  25                  30

Ala Met Gln Trp Val Arg Gln Ala Arg Gly Gln Arg Pro Glu Trp Ile
        35                  40                  45

Gly Trp Ile Val Leu Gly Ser Gly Asn Thr Asn Tyr Ala Gln Lys Phe
    50                  55                  60

Gln Glu Arg Val Thr Leu Thr Arg Asp Met Ser Thr Ala Thr Ala Tyr
65                  70                  75                  80

Met Glu Leu Ser Ser Leu Arg Ser Glu Asp Thr Ala Val Tyr Tyr Cys
                85                  90                  95

Ala Ala Asp Arg Gly Arg Gly Gly Tyr Asn Val Tyr Thr Tyr Trp Gly
            100                 105                 110

Gln Gly Thr Leu Val Ala Val Ser Ser
        115                 120

<210> SEQ ID NO 243
<211> LENGTH: 108
<212> TYPE: PRT
<213> ORGANISM: Homo sapiens

<400> SEQUENCE: 243

Glu Ile Val Met Thr Gln Ser Pro Gly Thr Leu Ser Leu Ser Pro Gly
1               5                   10                  15

Glu Arg Ala Thr Leu Ser Cys Arg Ala Ser Gln Thr Ile Ser Asn Thr
            20                  25                  30

Tyr Val Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Arg Arg Leu Glu
65                  70                  75                  80

Pro Glu Asp Phe Ala Val Tyr Tyr Cys Gln Gln Asn Gly Gln Ser Pro
            85                  90                  95

Trp Thr Phe Gly Gln Gly Thr Asn Val Glu Ile Lys
            100                 105

<210> SEQ ID NO 244
<211> LENGTH: 364
<212> TYPE: DNA
<213> ORGANISM: Homo sapiens

<400> SEQUENCE: 244
caaatgcagc tggtgcagtc tgggcctcaa gtgaagaagc ctgggacctc agtgaaggtc        60
tcctgcaagg cttctggatt cacctttact agctctgcta tgcagtgggt gcggcaggct      120
cgtggacagc gccctgagtg gataggatgg atcgtccttg gcagcggtaa cacaaactac      180
gcacagaagt tccaggaaag agtcaccctt accagggaca tgtccactgc tacagcctac      240
atggaactga gcagcctgag atccgaggac acggccgtgt attactgtgc ggcagatagg      300
ggtagaggtg gatacaatgt atacacttac tggggccagg ggaccctggt cgccgtctcc      360
tcag                                                                   364

<210> SEQ ID NO 245
<211> LENGTH: 325
<212> TYPE: DNA
<213> ORGANISM: Homo sapiens

<400> SEQUENCE: 245
gaaattgtga tgacgcagtc tccaggcacc ctgtctttgt ctccagggga aagagccacc        60
ctctcctgca gggccagtca gactattagt aacacctacg tggcctggta ccagcagaaa      120
cctggccagg ctcccaggct cctcatctat ggtgcatcca gcagggccac tggcatccca      180
gacaggttca gtggcagtgg gtctgggaca gacttcactc tcaccatccg cagactggag      240
cctgaagatt ttgcagtgta ttactgtcag cagaatggtc agtcaccttg gacgttcggc      300
caagggacca acgtggaaat caaac                                             325

<210> SEQ ID NO 246
<211> LENGTH: 8
<212> TYPE: PRT
<213> ORGANISM: Homo sapiens

<400> SEQUENCE: 246

Gly Tyr Thr Phe Thr Gly Tyr Tyr
1               5

<210> SEQ ID NO 247
<211> LENGTH: 8
<212> TYPE: PRT
<213> ORGANISM: Homo sapiens

<400> SEQUENCE: 247

Ile Asn Pro Met Thr Gly Ala Thr
1               5

<210> SEQ ID NO 248
<211> LENGTH: 18
<212> TYPE: PRT
<213> ORGANISM: Homo sapiens

<400> SEQUENCE: 248

Ala Arg Gly Gly Pro Thr Ser Thr Arg Ile Thr Gly Lys Arg His Phe
1               5                   10                  15

Asp Leu

<210> SEQ ID NO 249
<211> LENGTH: 9
<212> TYPE: PRT
<213> ORGANISM: Homo sapiens

<400> SEQUENCE: 249

Ile Ser Asp Val Gly Ala Tyr Asn Ser
1               5

<210> SEQ ID NO 250
<211> LENGTH: 3
<212> TYPE: PRT
<213> ORGANISM: Homo sapiens

<400> SEQUENCE: 250

Asp Val Thr
1

<210> SEQ ID NO 251
<211> LENGTH: 10
<212> TYPE: PRT
<213> ORGANISM: Homo sapiens

<400> SEQUENCE: 251

Ser Ser Tyr Thr Thr Ser Asp Thr Tyr Val
1               5                   10

<210> SEQ ID NO 252
<211> LENGTH: 24
<212> TYPE: DNA
<213> ORGANISM: Homo sapiens

<400> SEQUENCE: 252
ggatacacct tcaccggcta ctat                                    24

<210> SEQ ID NO 253
<211> LENGTH: 24
<212> TYPE: DNA
<213> ORGANISM: Homo sapiens

<400> SEQUENCE: 253
atcaacccta tgactggagc caca                                    24

<210> SEQ ID NO 254
<211> LENGTH: 54
<212> TYPE: DNA
<213> ORGANISM: Homo sapiens

<400> SEQUENCE: 254
gcgagaggag gtcctaccag tacccgaata acagggaaac ggcacttcga tctc   54

<210> SEQ ID NO 255
<211> LENGTH: 27
<212> TYPE: DNA
<213> ORGANISM: Homo sapiens

<400> SEQUENCE: 255
atcagtgacg ttggtgctta taactct                                 27

<210> SEQ ID NO 256
<211> LENGTH: 9
<212> TYPE: DNA
<213> ORGANISM: Homo sapiens

<400> SEQUENCE: 256 gacgtcact                                                                  9

<210> SEQ ID NO 257
<211> LENGTH: 30
<212> TYPE: DNA
<213> ORGANISM: Homo sapiens

<400> SEQUENCE: 257
agctcatata caaccagtga cacttatgtc                                          30

<210> SEQ ID NO 258
<211> LENGTH: 125
<212> TYPE: PRT
<213> ORGANISM: Homo sapiens

<400> SEQUENCE: 258

Arg Ala Gln Leu Val Gln Ser Ala Ala Glu Met Lys Asn Pro Gly Ala
1               5                   10                  15

Ser Val Lys Val Ser Cys Glu Ala Ser Gly Tyr Thr Phe Thr Gly Tyr
            20                  25                  30

Tyr Val His Trp Met Arg Gln Ala Pro Gly Gln Gly Leu Glu Trp Met
        35                  40                  45

Gly Trp Ile Asn Pro Met Thr Gly Ala Thr Lys Ser Pro Gln Lys Phe
    50                  55                  60

Gln Gly Arg Val Thr Met Thr Arg Asp Thr Ser Thr Ala Thr His
65                  70                  75                  80

Ile Glu Leu Thr Arg Leu Arg Ser Asp Asp Ser Ala Val Phe Phe Cys
                85                  90                  95

Ala Arg Gly Gly Pro Thr Ser Thr Arg Ile Thr Gly Lys Arg His Phe
            100                 105                 110

Asp Leu Trp Gly Arg Gly Thr Leu Ile Thr Val Ala Ser
        115                 120                 125

<210> SEQ ID NO 259
<211> LENGTH: 110
<212> TYPE: PRT
<213> ORGANISM: Homo sapiens

<400> SEQUENCE: 259

Gln Ser Ala Leu Thr Gln Pro Ala Ser Val Ser Gly Ser Pro Gly Glu
1               5                   10                  15

Ser Ile Thr Ile Ser Cys Thr Gly Thr Ile Ser Asp Val Gly Ala Tyr
            20                  25                  30

Asn Ser Val Ser Trp Tyr Gln Gln His Ser Gly Thr Ala Pro Glu Leu
        35                  40                  45

Ile Ile Tyr Asp Val Thr Asn Arg Pro Ala Gly Val Ser Ser Arg Phe
    50                  55                  60

Ser Gly Ser Lys Ser Gly Asn Thr Ala Ser Leu Thr Ile Ser Trp Leu
65                  70                  75                  80

Gln Ser Glu Asp Glu Ala Glu Tyr Tyr Cys Ser Ser Tyr Thr Thr Ser
                85                  90                  95

Asp Thr Tyr Val Phe Gly Ser Gly Thr Gln Val Thr Val Leu
            100                 105                 110

<210> SEQ ID NO 260
<211> LENGTH: 376
<212> TYPE: DNA
<213> ORGANISM: Homo sapiens

<400> SEQUENCE: 260

```
cgggcgcagt tggtgcagtc tgcggctgag atgaagaacc ctggggcctc agtgaaggtc      60
tcctgcgagg cttctggata caccttcacc ggctactatg tacactggat gcgacaggcc     120
cccggacaag gactagagtg gatgggatgg atcaaccctg actggagc acaaagtct        180
ccacagaagt tcagggcag gtcaccatg accaggaca cttccaccac cgcaaccca         240
atagaactga ctaggctgag atctgacgac agtgccgtct ttttctgtgc gagaggaggt     300
cctaccagta cccgaataac agggaaacgg cacttcgatc tctggggccg cggcaccctg     360
atcactgtcg cctcag                                                     376
```

<210> SEQ ID NO 261
<211> LENGTH: 331
<212> TYPE: DNA
<213> ORGANISM: Homo sapiens

<400> SEQUENCE: 261

```
cagtctgccc tgactcagcc tgcctccgtg tctgggtctc ctggagagtc gatcaccatc      60
tcctgcactg gaaccatcag tgacgttggt gcttataact ctgtctcctg gtaccaacaa    120
cactcaggca cagcccccga actcatcatt tatgacgtca ctaatcggcc cgcagggtt     180
tcgagtcgct tctctggctc caagtctggc aacacggcct ccctgaccat ctcttggctc    240
cagtctgagg acgaggctga atattattgc agctcatata accagtga cacttatgtc      300
ttcggaagtg ggacccaagt caccgtccta a                                   331
```

<210> SEQ ID NO 262
<211> LENGTH: 8
<212> TYPE: PRT
<213> ORGANISM: Homo sapiens

<400> SEQUENCE: 262

Gly Phe Thr Val Ser Thr Thr Tyr
1               5

<210> SEQ ID NO 263
<211> LENGTH: 12
<212> TYPE: PRT
<213> ORGANISM: Homo sapiens

<400> SEQUENCE: 263

Ile His Thr Gly Gly Ile Phe Gly Val Gly Gly Thr
1               5                   10

<210> SEQ ID NO 264
<211> LENGTH: 13
<212> TYPE: PRT
<213> ORGANISM: Homo sapiens

<400> SEQUENCE: 264

Ala Arg Glu His Arg Gly Thr Ile Asp Ala Phe Asp Ala
1               5                   10

<210> SEQ ID NO 265
<211> LENGTH: 6

<212> TYPE: PRT
<213> ORGANISM: Homo sapiens

<400> SEQUENCE: 265

Gln Asn Ile Arg Asn Tyr
1               5

<210> SEQ ID NO 266
<211> LENGTH: 3
<212> TYPE: PRT
<213> ORGANISM: Homo sapiens

<400> SEQUENCE: 266

Thr Thr Ser
1

<210> SEQ ID NO 267
<211> LENGTH: 8
<212> TYPE: PRT
<213> ORGANISM: Homo sapiens

<400> SEQUENCE: 267

Gln Gln Ser Tyr Asp Gly Trp Thr
1               5

<210> SEQ ID NO 268
<211> LENGTH: 24
<212> TYPE: DNA
<213> ORGANISM: Homo sapiens

<400> SEQUENCE: 268
ggattcaccg tcagtaccac ctac                                          24

<210> SEQ ID NO 269
<211> LENGTH: 36
<212> TYPE: DNA
<213> ORGANISM: Homo sapiens

<400> SEQUENCE: 269
attcataccg gtggcatttt tggcgttggc ggtaca                             36

<210> SEQ ID NO 270
<211> LENGTH: 39
<212> TYPE: DNA
<213> ORGANISM: Homo sapiens

<400> SEQUENCE: 270
gcgagggaac atcggggaac tatcgatgct tttgatgcc                          39

<210> SEQ ID NO 271
<211> LENGTH: 18
<212> TYPE: DNA
<213> ORGANISM: Homo sapiens

<400> SEQUENCE: 271
cagaacattc gaaattat                                                 18

<210> SEQ ID NO 272
<211> LENGTH: 9
<212> TYPE: DNA
<213> ORGANISM: Homo sapiens

<400> SEQUENCE: 272 actacatcc                                                            9

<210> SEQ ID NO 273
<211> LENGTH: 24
<212> TYPE: DNA
<213> ORGANISM: Homo sapiens

<400> SEQUENCE: 273
caacagagtt acgatgggtg gacg    24

<210> SEQ ID NO 274
<211> LENGTH: 124
<212> TYPE: PRT
<213> ORGANISM: Homo sapiens

<400> SEQUENCE: 274

Glu Val Arg Leu Glu Glu Ser Gly Gly Gly Leu Val Gln Pro Gly Gly
1               5                   10                  15

Ser Leu Arg Leu Ser Cys Ala Ala Ser Gly Phe Thr Val Ser Thr Thr
            20                  25                  30

Tyr Met Ala Trp Val Arg Gln Ala Pro Gly Lys Gly Leu Glu Trp Val
        35                  40                  45

Ser Leu Ile His Thr Gly Gly Ile Phe Gly Val Gly Gly Thr Ser Tyr
    50                  55                  60

Ala Asp Ser Val Lys Gly Arg Phe Thr Ile Ser Arg Asp Thr Ser Lys
65                  70                  75                  80

Asn Thr Val Ser Leu Gln Met Ser Ser Leu Arg Val Glu Asp Thr Ala
                85                  90                  95

Ile Tyr Phe Cys Ala Arg Glu His Arg Gly Thr Ile Asp Ala Phe Asp
            100                 105                 110

Ala Trp Gly Gln Gly Thr Val Val Ile Val Ser Ser
        115                 120

<210> SEQ ID NO 275
<211> LENGTH: 106
<212> TYPE: PRT
<213> ORGANISM: Homo sapiens

<400> SEQUENCE: 275

Asp Ile His Met Thr Gln Ser Pro Ser Ser Leu Ser Ala Ser Val Gly
1               5                   10                  15

Asp Arg Val Thr Ile Thr Cys Arg Ala Ser Gln Asn Ile Arg Asn Tyr
            20                  25                  30

Leu Asn Trp Tyr Gln His Lys Pro Gly Lys Ala Pro Lys Leu Leu Ile
        35                  40                  45

Tyr Thr Thr Ser Arg Leu Gln Ser Gly Val Pro Ser Arg Phe Ser Gly
    50                  55                  60

Ser Gly Ser Gly Thr Asp Phe Thr Leu Thr Val Asn Ser Leu Gln Pro
65                  70                  75                  80

Glu Asp Phe Ala Ser Tyr Tyr Cys Gln Gln Ser Tyr Asp Gly Trp Thr
                85                  90                  95

Phe Gly Gln Gly Thr Lys Val Glu Met Lys
            100                 105

<210> SEQ ID NO 276
<211> LENGTH: 373
<212> TYPE: DNA
<213> ORGANISM: Homo sapiens

<400> SEQUENCE: 276

```
gaggtgcgac tggaggagtc tggggggaggc ttggtccagc ctgggggggtc cctgagactc      60 tcctgtgcag cctctggatt caccgtcagt accacctaca tggcctgggt ccgccaggct     120
ccagggaagg ggctggaatg ggtctcactt attcataccg gtggcatttt tggcgttggc     180
ggtacatcct acgcagactc cgtgaagggc agattcacca tctccagaga cacttccaag     240
aacacagtgt ctcttcaaat gagcagcctg agagtcgagg acacggccat ctatttctgt     300
gcgagggaac atcggggaac tatcgatgct tttgatgcct ggggccaagg gacagtggtc     360
atcgtctctt cag                                                         373
```

```
<210> SEQ ID NO 277
<211> LENGTH: 319
<212> TYPE: DNA
<213> ORGANISM: Homo sapiens

<400> SEQUENCE: 277
```

```
gacatccaca tgacccagtc tccatcctcc ctgtctgcat ctgttggaga cagagtcacc      60
atcacttgcc gggcaagtca gaacattcga aattatttaa attggtatca acataaacca     120
gggaaagccc ctaaactcct gatctatact acatcccgtc tgcaaagtgg ggtcccatca     180
aggttcagtg gcagtggatc tgggacagat ttcactctca ccgtcaacag cctgcaacca     240
gaagactttg caagttacta ctgtcaacag agttacgatg ggtggacgtt cggccagggg     300
accaaggtgg aaatgaaac                                                   319
```

```
<210> SEQ ID NO 278
<211> LENGTH: 8
<212> TYPE: PRT
<213> ORGANISM: Homo sapiens

<400> SEQUENCE: 278

Gly Phe Thr Phe Ser Ser Tyr Glu
1               5
```

```
<210> SEQ ID NO 279
<211> LENGTH: 8
<212> TYPE: PRT
<213> ORGANISM: Homo sapiens

<400> SEQUENCE: 279

Ile Asp Phe Thr Gly Ser Thr Ile
1               5
```

```
<210> SEQ ID NO 280
<211> LENGTH: 16
<212> TYPE: PRT
<213> ORGANISM: Homo sapiens

<400> SEQUENCE: 280

Val Arg Asp Ala Gly Arg Trp Gly Thr Ser Trp Tyr Tyr Phe Asp Tyr
1               5                   10                  15
```

```
<210> SEQ ID NO 281
<211> LENGTH: 9
<212> TYPE: PRT
<213> ORGANISM: Homo sapiens

<400> SEQUENCE: 281

Ser Ser Asn Ile Gly Ala Gly Tyr Asp
1               5
```

```
<210> SEQ ID NO 282
<211> LENGTH: 3
<212> TYPE: PRT
<213> ORGANISM: Homo sapiens

<400> SEQUENCE: 282

Gly Asn Asn
1

<210> SEQ ID NO 283
<211> LENGTH: 11
<212> TYPE: PRT
<213> ORGANISM: Homo sapiens

<400> SEQUENCE: 283

Gln Ser Tyr Asp Ser Ser Leu Asn Gly Trp Val
1               5                   10

<210> SEQ ID NO 284
<211> LENGTH: 24
<212> TYPE: DNA
<213> ORGANISM: Homo sapiens

<400> SEQUENCE: 284
ggattcactt tcagtagcta tgag                                          24

<210> SEQ ID NO 285
<211> LENGTH: 24
<212> TYPE: DNA
<213> ORGANISM: Homo sapiens

<400> SEQUENCE: 285
attgatttta ctggctcaac catc                                          24

<210> SEQ ID NO 286
<211> LENGTH: 48
<212> TYPE: DNA
<213> ORGANISM: Homo sapiens

<400> SEQUENCE: 286
gtgagagatg cgggccgttg gggcaccagt tggtactact ttgactat                48

<210> SEQ ID NO 287
<211> LENGTH: 27
<212> TYPE: DNA
<213> ORGANISM: Homo sapiens

<400> SEQUENCE: 287
agctccaaca tcggggcagg ttatgat                                       27

<210> SEQ ID NO 288
<211> LENGTH: 9
<212> TYPE: DNA
<213> ORGANISM: Homo sapiens

<400> SEQUENCE: 288 ggtaacaac                                                            9

<210> SEQ ID NO 289
<211> LENGTH: 33
<212> TYPE: DNA
<213> ORGANISM: Homo sapiens

<400> SEQUENCE: 289
```
cagtcgtatg acagcagcct gaatggttgg gtg         33

<210> SEQ ID NO 290
<211> LENGTH: 123
<212> TYPE: PRT
<213> ORGANISM: Homo sapiens

<400> SEQUENCE: 290

Ala Val Gln Leu Val Glu Ser Gly Gly Gly Leu Ala Gln Pro Gly Arg
1               5                   10                  15

Ser Leu Arg Leu Ser Cys Lys Val Ser Gly Phe Thr Phe Ser Ser Tyr
            20                  25                  30

Glu Met Asn Trp Val Arg Gln Ala Pro Gly Lys Gly Leu Glu Trp Ile
        35                  40                  45

Ala Tyr Ile Asp Phe Thr Gly Ser Thr Ile Tyr Tyr Ala Asp Ser Val
    50                  55                  60

Lys Gly Arg Phe Thr Ile Ser Arg Asp Thr Ala Arg Asn Ser Leu Tyr
65                  70                  75                  80

Leu Gln Met Asn Lys Leu Arg Val Glu Asp Thr Ala Val Tyr Tyr Cys
                85                  90                  95

Val Arg Asp Ala Gly Arg Trp Gly Thr Ser Trp Tyr Tyr Phe Asp Tyr
            100                 105                 110

Trp Gly Gln Gly Thr Leu Val Thr Val Ser Ser
        115                 120

<210> SEQ ID NO 291
<211> LENGTH: 111
<212> TYPE: PRT
<213> ORGANISM: Homo sapiens

<400> SEQUENCE: 291

Gln Ser Val Leu Thr Gln Pro Pro Ser Val Ser Gly Ala Pro Gly Gln
1               5                   10                  15

Arg Val Thr Ile Ser Cys Thr Gly Leu Ser Ser Asn Ile Gly Ala Gly
            20                  25                  30

Tyr Asp Ile His Trp Tyr Gln Gln Ile Pro Gly Lys Ala Pro Lys Leu
        35                  40                  45

Leu Ile Tyr Gly Asn Asn Asn Arg Pro Ser Gly Val Pro Asp Arg Phe
    50                  55                  60

Ser Gly Ser Lys Ser Gly Thr Ser Val Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Asn Gly Trp Val Phe Gly Gly Gly Thr Arg Leu Thr Val Leu
            100                 105                 110

<210> SEQ ID NO 292
<211> LENGTH: 370
<212> TYPE: DNA
<213> ORGANISM: Homo sapiens

<400> SEQUENCE: 292
gcggtgcagc tggtggagtc tgggggcggc ttggcacagc ctggacggtc cctgaggctc    60
tcgtgtaaag tgtctggatt cactttcagt agctatgaga tgaactgggt ccgccaggct   120
ccagggaagg gcctgagtg gattgcatac attgatttta ctggctcaac catctactac   180
gcagactctg tgaagggacg attcaccatt tccagagaca ccgccaggaa ctcactctat   240

```
ctgcagatga acaaattgag agtcgaggac acggctgttt attactgtgt gagagatgcg    300
ggccgttggg gcaccagttg gtactacttt gactattggg gccagggaac cctggtcacc    360
gtctcctcag                                                            370
```

<210> SEQ ID NO 293
<211> LENGTH: 334
<212> TYPE: DNA
<213> ORGANISM: Homo sapiens

<400> SEQUENCE: 293

```
cagtctgtgc tgacgcagcc gccctcagtg tctggggccc cagggcagag ggtcaccatc     60
tcctgcactg ggctcagctc aacatcgggg gcaggttatg atatacactg gtatcagcag    120
attccaggaa aagcccccaa actcctcatc tatggtaaca acaatcggcc ctcaggggtc    180
cctgaccgat tctctggctc taagtctggc acctcagtct ccctggccat cactgggctc    240
caggctgagg atgaggctga ttattactgc cagtcgtatg acagcagcct gaatggttgg    300
gtgttcggcg gagggaccag gttgaccgtc ctaa                                 334
```

<210> SEQ ID NO 294
<211> LENGTH: 123
<212> TYPE: PRT
<213> ORGANISM: Homo sapiens

<400> SEQUENCE: 294

```
Ala Val Gln Leu Val Glu Ser Gly Gly Asp Leu Ala Gln Pro Gly Arg
1               5                   10                  15

Ser Leu Arg Leu Ser Cys Lys Val Ser Gly Phe Thr Phe Ser Ser Tyr
            20                  25                  30

Glu Met Asn Trp Val Arg Gln Ala Pro Gly Lys Gly Leu Glu Trp Ile
        35                  40                  45

Ala Tyr Ile Asp Phe Thr Gly Ser Thr Ile Tyr Ala Asp Ser Val
    50                  55                  60

Lys Gly Arg Phe Thr Ile Ser Arg Asp Thr Ala Arg Asn Ser Leu Tyr
65                  70                  75                  80

Leu Gln Met Asn Lys Leu Arg Val Glu Asp Thr Ala Val Tyr Tyr Cys
                85                  90                  95

Val Arg Asp Ala Gly Arg Trp Gly Thr Ser Trp Tyr Tyr Phe Asp Tyr
            100                 105                 110

Trp Gly Gln Gly Thr Leu Val Thr Val Ser Ser
        115                 120
```

<210> SEQ ID NO 295
<211> LENGTH: 370
<212> TYPE: DNA
<213> ORGANISM: Homo sapiens

<400> SEQUENCE: 295

```
gcggtgcagc tggtggagtc tgggggcgac ttggcacagc ctggacggtc cctgaggctc     60
tcgtgtaaag tgtctggatt cactttcagt agctatgaga tgaactgggt ccgccaggct    120
ccagggaagg ggctggagtg gattgcatac attgatttta ctggctcaac catctactac    180
gcagactctg tgaagggacg attcaccatt tccagagaca ccgccaggaa ctcactctat    240
ctgcagatga acaaattgag agtcgaggac acggctgttt attactgtgt gagagatgcg    300
ggccgttggg gcaccagttg gtactacttt gactattggg gccagggaac cctggtcacc    360
```

```
gtctcctcag                                                           370
```

<210> SEQ ID NO 296
<211> LENGTH: 8
<212> TYPE: PRT
<213> ORGANISM: Homo sapiens

<400> SEQUENCE: 296

Gly Phe Thr Phe Ser Ser His Glu
1               5

<210> SEQ ID NO 297
<211> LENGTH: 8
<212> TYPE: PRT
<213> ORGANISM: Homo sapiens

<400> SEQUENCE: 297

Ile Asp Phe Thr Gly Ser Ile Ile
1               5

<210> SEQ ID NO 298
<211> LENGTH: 16
<212> TYPE: PRT
<213> ORGANISM: Homo sapiens

<400> SEQUENCE: 298

Ala Arg Asp Gly Gly Arg Trp Gly Thr Ser Trp Tyr Tyr Phe Asp Tyr
1               5                   10                  15

<210> SEQ ID NO 299
<211> LENGTH: 9
<212> TYPE: PRT
<213> ORGANISM: Homo sapiens

<400> SEQUENCE: 299

Ser Ser Asn Phe Gly Ala Gly Tyr Asp
1               5

<210> SEQ ID NO 300
<211> LENGTH: 2
<212> TYPE: PRT
<213> ORGANISM: Homo sapiens

<400> SEQUENCE: 300

Gly Ser
1

<210> SEQ ID NO 301
<211> LENGTH: 11
<212> TYPE: PRT
<213> ORGANISM: Homo sapiens

<400> SEQUENCE: 301

Gln Ser Tyr Asp Ser Ser Leu Ser Ala Trp Val
1               5                   10

<210> SEQ ID NO 302
<211> LENGTH: 24
<212> TYPE: DNA
<213> ORGANISM: Homo sapiens

<400> SEQUENCE: 302

```
ggattcacct tcagttctca tgag                                           24
```

```
<210> SEQ ID NO 303
<211> LENGTH: 24
<212> TYPE: DNA
<213> ORGANISM: Homo sapiens

<400> SEQUENCE: 303
attgatttta ctggcagtat tata                                          24

<210> SEQ ID NO 304
<211> LENGTH: 48
<212> TYPE: DNA
<213> ORGANISM: Homo sapiens

<400> SEQUENCE: 304
gcgagagatg ggggtcgttg gggcaccagt tggtactact ttgactac                48

<210> SEQ ID NO 305
<211> LENGTH: 27
<212> TYPE: DNA
<213> ORGANISM: Homo sapiens

<400> SEQUENCE: 305
agttccaact tcggggcagg ttatgat                                       27

<210> SEQ ID NO 306
<211> LENGTH: 6
<212> TYPE: DNA
<213> ORGANISM: Homo sapiens

<400> SEQUENCE: 306 ggtagc                                                               6

<210> SEQ ID NO 307
<211> LENGTH: 33
<212> TYPE: DNA
<213> ORGANISM: Homo sapiens

<400> SEQUENCE: 307
cagtcctatg acagcagcct gagcgcttgg gtg                                33

<210> SEQ ID NO 308
<211> LENGTH: 123
<212> TYPE: PRT
<213> ORGANISM: Homo sapiens

<400> SEQUENCE: 308
```

Ala Val Gln Leu Val Glu Ser Gly Gly Gly Leu Val Arg Pro Gly Gly
1               5                   10                  15

Ser Leu Arg Leu Ser Cys Ala Ala Ser Gly Phe Thr Phe Ser Ser His
            20                  25                  30

Glu Met His Trp Val Arg Gln Ala Pro Gly Lys Gly Leu Glu Trp Leu
        35                  40                  45

Ser Tyr Ile Asp Phe Thr Gly Ser Ile Ile Tyr Ala Asp Ser Val
    50                  55                  60

Arg Gly Arg Phe Thr Ile Ser Arg Asp Asn Thr Lys Lys Ser Leu Phe
65                  70                  75                  80

Leu Gln Met Asn Ser Leu Arg Asp Glu Asp Thr Ala Leu Tyr Tyr Cys
                85                  90                  95

Ala Arg Asp Gly Gly Arg Trp Gly Thr Ser Trp Tyr Tyr Phe Asp Tyr
            100                 105                 110

Trp Gly Gln Gly Val Leu Val Thr Val Ser Ser

<210> SEQ ID NO 309
<211> LENGTH: 110
<212> TYPE: PRT
<213> ORGANISM: Homo sapiens

<400> SEQUENCE: 309

Gln Ser Val Leu Thr Gln Pro Pro Ser Val Ser Gly Ala Pro Gly Gln
1               5                   10                  15
Arg Val Thr Ile Thr Cys Thr Gly Ser Ser Ser Asn Phe Gly Ala Gly
            20                  25                  30
Tyr Asp Gly His Trp Tyr Gln Gln Leu Pro Gly Thr Ala Pro Lys Leu
        35                  40                  45
Leu Ile Tyr Gly Ser Asn Arg Pro Ser Gly Val Pro Asp Arg Phe Ser
    50                  55                  60
Gly Ser Lys Ser Gly Thr Ser Val Ser Leu Ala Ile Thr Gly Leu Gln
65                  70                  75                  80
Ala Asp Asp Glu Ala Asp Tyr Tyr Cys Gln Ser Tyr Asp Ser Ser Leu
                85                  90                  95
Ser Ala Trp Val Phe Gly Gly Gly Thr Lys Leu Thr Val Leu
            100                 105                 110

<210> SEQ ID NO 310
<211> LENGTH: 370
<212> TYPE: DNA
<213> ORGANISM: Homo sapiens

<400> SEQUENCE: 310
gcggtgcagc tggtggagtc tgggggaggc ttggtacggc ctggagggtc cctgagactc      60
tcctgtgcag cctctggatt caccttcagt tctcatgaga tgcactgggt ccgccaggct     120
ccagggaagg ggctggaatg gctttcatac attgatttta ctgcagtat tatatactac     180 gcagactctg tgaggggtcg gttcaccatc tccagagaca acaccaaaaa gtcactgttt     240
ctgcaaatga acagcctgag agacgaggat acggctcttt attactgtgc gagagatggg     300
ggtcgttggg gcaccagttg gtactacttt gactactggg gccagggagt cctggtcacc     360
gtctcctcag                                                            370

<210> SEQ ID NO 311
<211> LENGTH: 331
<212> TYPE: DNA
<213> ORGANISM: Homo sapiens

<400> SEQUENCE: 311
cagtctgtgc tgacgcagcc gccctcagtg tctggggccc cagggcagag ggtcaccata      60
acctgcactg ggagcagttc aacttcgggg caggttatg atggacactg gtaccagcaa     120
cttccaggaa cagccccca actcctcatc tatggtagca atcggccctc aggggtccct     180
gaccgattct ctggctccaa gtctggcacc tcagtctccc tggccatcac tgggctccag     240
gctgacgatg aggctgatta ttactgccag tcctatgaca gcagcctgag cgcttgggtg     300
ttcggcggag ggaccaagct gaccgtccta c                                    331

<210> SEQ ID NO 312
<211> LENGTH: 8
<212> TYPE: PRT
<213> ORGANISM: Homo sapiens

```
<400> SEQUENCE: 312

Ile Asp Phe Thr Gly Ser Ser Ile
1               5

<210> SEQ ID NO 313
<211> LENGTH: 24
<212> TYPE: DNA
<213> ORGANISM: Homo sapiens

<400> SEQUENCE: 313
attgatttta ctggcagtag tata                                              24

<210> SEQ ID NO 314
<211> LENGTH: 123
<212> TYPE: PRT
<213> ORGANISM: Homo sapiens

<400> SEQUENCE: 314

Ala Val Gln Leu Val Glu Ser Gly Gly Gly Leu Val Arg Pro Gly Gly
1               5                   10                  15

Ser Leu Arg Leu Ser Cys Ala Ala Ser Gly Phe Thr Phe Ser Ser His
            20                  25                  30

Glu Met His Trp Val Arg Gln Ala Pro Gly Lys Gly Leu Glu Trp Leu
        35                  40                  45

Ser Tyr Ile Asp Phe Thr Gly Ser Ser Ile Tyr Tyr Ala Asp Ser Val
    50                  55                  60

Arg Gly Arg Phe Thr Ile Ser Arg Asp Asn Thr Lys Lys Ser Leu Phe
65                  70                  75                  80

Leu Gln Met Asn Ser Leu Arg Asp Glu Asp Thr Ala Leu Tyr Tyr Cys
                85                  90                  95

Ala Arg Asp Gly Gly Arg Trp Gly Thr Ser Trp Tyr Tyr Phe Asp Tyr
            100                 105                 110

Trp Gly Gln Gly Val Leu Val Thr Val Ser Ser
        115                 120

<210> SEQ ID NO 315
<211> LENGTH: 370
<212> TYPE: DNA
<213> ORGANISM: Homo sapiens

<400> SEQUENCE: 315
gcggtgcagc tggtggagtc tgggggaggc ttggtacggc ctggagggtc cctgagactc     60
tcctgtgcag cctctggatt caccttcagt tctcatgaga tgcactgggt ccgccaggct    120
ccagggaagg ggctggaatg gctttcatac attgatttta ctggcagtag tatatactac    180
gcagactctg tgaggggtcg gttcaccatc tccagagaca ataccaaaaa gtcactgttt    240
ctgcaaatga acagcctgag agacgaggat acggctcttt attactgtgc gagagatggg    300
ggtcgttggg gcaccagttg gtactacttt gactactggg gccaggagtc cctggtcacc    360
gtctcctcag                                                          370

<210> SEQ ID NO 316
<211> LENGTH: 8
<212> TYPE: PRT
<213> ORGANISM: Homo sapiens

<400> SEQUENCE: 316

Gly Tyr Thr Phe Thr Asp Tyr Tyr
1               5
```

<210> SEQ ID NO 317
<211> LENGTH: 8
<212> TYPE: PRT
<213> ORGANISM: Homo sapiens

<400> SEQUENCE: 317

Phe Asn Pro Asn Ser Gly Gly Thr
1               5

<210> SEQ ID NO 318
<211> LENGTH: 23
<212> TYPE: PRT
<213> ORGANISM: Homo sapiens

<400> SEQUENCE: 318

Ala Lys Asp Ser Ala Lys Thr Ala Ser Ala Tyr Tyr Gly Leu Asn Phe
1               5                   10                  15

Phe Tyr Tyr Gly Met Asp Val
            20

<210> SEQ ID NO 319
<211> LENGTH: 8
<212> TYPE: PRT
<213> ORGANISM: Homo sapiens

<400> SEQUENCE: 319

Ser Ser Asn Ile Gly Lys Asn Tyr
1               5

<210> SEQ ID NO 320
<211> LENGTH: 3
<212> TYPE: PRT
<213> ORGANISM: Homo sapiens

<400> SEQUENCE: 320

Lys Asn Asn
1

<210> SEQ ID NO 321
<211> LENGTH: 11
<212> TYPE: PRT
<213> ORGANISM: Homo sapiens

<400> SEQUENCE: 321

Ser Ala Trp Asp Gly Ser Leu Ser Arg Pro Leu
1               5                   10

<210> SEQ ID NO 322
<211> LENGTH: 24
<212> TYPE: DNA
<213> ORGANISM: Homo sapiens

<400> SEQUENCE: 322
ggatacacct tcaccgacta ctat                                          24

<210> SEQ ID NO 323
<211> LENGTH: 24
<212> TYPE: DNA
<213> ORGANISM: Homo sapiens

<400> SEQUENCE: 323
ttcaacccta acagtggtgg caca                                          24

<210> SEQ ID NO 324
<211> LENGTH: 69
<212> TYPE: DNA
<213> ORGANISM: Homo sapiens

<400> SEQUENCE: 324
gcgaaagatt ccgcgaaaac tgcgagtgct tattatggac tgaacttctt ctactacggt    60
atggacgtc                                                            69

<210> SEQ ID NO 325
<211> LENGTH: 24
<212> TYPE: DNA
<213> ORGANISM: Homo sapiens

<400> SEQUENCE: 325
agttccaaca tcggaaagaa ttat                                           24

<210> SEQ ID NO 326
<211> LENGTH: 9
<212> TYPE: DNA
<213> ORGANISM: Homo sapiens

<400> SEQUENCE: 326 aagaataat                                                            9

<210> SEQ ID NO 327
<211> LENGTH: 33
<212> TYPE: DNA
<213> ORGANISM: Homo sapiens

<400> SEQUENCE: 327
tcagcgtggg atggcagcct gagtcgtcca cta                                 33

<210> SEQ ID NO 328
<211> LENGTH: 130
<212> TYPE: PRT
<213> ORGANISM: Homo sapiens

<400> SEQUENCE: 328

Gln Val Gln Leu Val Gln Ser Gly Ala Glu Val Lys Asn Pro Gly Ala
1               5                   10                  15

Ser Val Lys Val Ser Cys Lys Ala Ser Gly Tyr Thr Phe Thr Asp Tyr
            20                  25                  30

Tyr Ile His Trp Val Arg Gln Ala Pro Gly Gln Gly Leu Glu Trp Met
        35                  40                  45

Gly Trp Phe Asn Pro Asn Ser Gly Gly Thr Asn Phe Val Gln Asn Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Met Tyr Tyr Cys
                85                  90                  95

Ala Lys Asp Ser Ala Lys Thr Ala Ser Ala Tyr Tyr Gly Leu Asn Phe
            100                 105                 110

Phe Tyr Tyr Gly Met Asp Val Trp Gly Gln Gly Thr Thr Val Thr Val
        115                 120                 125

Ser Ser
    130

<210> SEQ ID NO 329

```
<211> LENGTH: 110
<212> TYPE: PRT
<213> ORGANISM: Homo sapiens

<400> SEQUENCE: 329

Gln Ser Val Leu Ser Gln Pro Pro Ser Ala Ser Gly Thr Pro Gly Gln
1               5                   10                  15

Arg Val Thr Ile Ser Cys Ser Gly Ser Ser Asn Ile Gly Lys Asn
                20                  25                  30

Tyr Val Tyr Trp Tyr Gln Gln Val Pro Gly Thr Ala Pro Lys Leu Leu
            35                  40                  45

Met Phe Lys Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ser Ala Trp Asp Gly Ser Leu
                85                  90                  95

Ser Arg Pro Leu Phe Gly Gly Gly Thr Lys Val Thr Val Leu
            100                 105                 110

<210> SEQ ID NO 330
<211> LENGTH: 391
<212> TYPE: DNA
<213> ORGANISM: Homo sapiens

<400> SEQUENCE: 330
caggtgcagc tggtgcagtc tggggctgaa gtgaagaacc ctggggcctc agtgaaggtc      60
tcctgcaagg cttctggata caccttcacc gactactata tacactgggt gcgacaggcc     120
cctggacaag gacttgagtg gatgggctgg ttcaaccccta acagtggtgg cacaaacttt    180
gtacagaact ttcagggcag ggtcaccatg accagggaca cgtccatcag cacagcctac    240
atggagctca gcaggctgag atctgacgac acggccatgt attactgtgc gaaagattcc    300
gcgaaaactg cgagtgctta ttatggactg aacttcttct actacggtat ggacgtctgg    360
ggccaaggga ccacggtcac cgtctcctca g                                    391

<210> SEQ ID NO 331
<211> LENGTH: 331
<212> TYPE: DNA
<213> ORGANISM: Homo sapiens

<400> SEQUENCE: 331
cagtctgtac tgagtcagcc accctcagca tctgggaccc ccgggcagag ggtcaccatc      60
tcttgttctg gaagcagttc caacatcgga agaattatg tatattggta ccagcaggtc     120
ccaggaacgg ccccccaaact cctcatgttt aagaataatc agcgaccctc aggggtccct    180
gaccgattct ctggctccaa gtctggcacc tctgcctccc tggccatcag tgggctccgg    240
tccgaggatg aggctgatta ttattgttca gcgtgggatg gcagcctgag tcgtccacta    300
ttcggcggag ggaccaaggt gaccgtccta g                                    331

<210> SEQ ID NO 332
<211> LENGTH: 23
<212> TYPE: PRT
<213> ORGANISM: Homo sapiens

<400> SEQUENCE: 332

Ala Arg Asp Ser Ala Lys Thr Ala Ser Ala Tyr Tyr Gly Leu Asn Phe
1               5                   10                  15
```

Phe Tyr Tyr Gly Met Asp Val
            20

<210> SEQ ID NO 333
<211> LENGTH: 69
<212> TYPE: DNA
<213> ORGANISM: Homo sapiens

<400> SEQUENCE: 333
gcgagagatt ccgcgaaaac tgcgagtgct tattatggac tgaacttctt ctactacggt      60
atggacgtc                                                              69

<210> SEQ ID NO 334
<211> LENGTH: 130
<212> TYPE: PRT
<213> ORGANISM: Homo sapiens

<400> SEQUENCE: 334

Gln Val Gln Leu Val Gln Ser Gly Ala Glu Val Lys Asn Pro Gly Ala
1               5                   10                  15

Ser Val Lys Val Ser Cys Lys Ala Ser Gly Tyr Thr Phe Thr Asp Tyr
            20                  25                  30

Tyr Ile His Trp Val Arg Gln Ala Pro Gly Gln Gly Leu Glu Trp Met
        35                  40                  45

Gly Trp Phe Asn Pro Asn Ser Gly Gly Thr Asn Phe Val Gln Asn Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Met Tyr Tyr Cys
                85                  90                  95

Ala Arg Asp Ser Ala Lys Thr Ala Ser Ala Tyr Tyr Gly Leu Asn Phe
            100                 105                 110

Phe Tyr Tyr Gly Met Asp Val Trp Gly Gln Gly Thr Thr Val Thr Val
        115                 120                 125

Ser Ser
    130

<210> SEQ ID NO 335
<211> LENGTH: 391
<212> TYPE: DNA
<213> ORGANISM: Homo sapiens

<400> SEQUENCE: 335
caggtgcagc tggtgcagtc tggggctgaa gtgaagaacc ctggggcctc agtgaaggtc      60
tcctgcaagg cttctggata caccttcacc gactactata tacactgggt gcgacaggcc     120
cctggacaag gacttgagtg gatgggctgg ttcaaccctc acagtggtgg cacaaacttt     180
gtacagaact tcagggcag gtcaccatg accaggaca cgtccatcag cacagcctac     240
atggagctca gcaggctgag atctgacgac acggccatgt attactgtgc gagagattcc     300
gcgaaaactg cgagtgctta ttatggactg aacttcttct actacggtat ggacgtctgg     360
ggccaaggga ccacggtcac cgtctcctca g                                    391

<210> SEQ ID NO 336
<211> LENGTH: 8
<212> TYPE: PRT
<213> ORGANISM: Homo sapiens

```
<400> SEQUENCE: 336

Gly Phe Arg Phe Asn Glu Phe Asn
1               5

<210> SEQ ID NO 337
<211> LENGTH: 8
<212> TYPE: PRT
<213> ORGANISM: Homo sapiens

<400> SEQUENCE: 337

Ile Ser Ile Asp Gly Arg His Lys
1               5

<210> SEQ ID NO 338
<211> LENGTH: 16
<212> TYPE: PRT
<213> ORGANISM: Homo sapiens

<400> SEQUENCE: 338

Val Thr Asp Gly Lys Ala Val Asp Gly Phe Ser Gly Ile Leu Glu Phe
1               5                   10                  15

<210> SEQ ID NO 339
<211> LENGTH: 6
<212> TYPE: PRT
<213> ORGANISM: Homo sapiens

<400> SEQUENCE: 339

Gln Ser Val Gly Gly Tyr
1               5

<210> SEQ ID NO 340
<211> LENGTH: 3
<212> TYPE: PRT
<213> ORGANISM: Homo sapiens

<400> SEQUENCE: 340

Asp Ala Ser
1

<210> SEQ ID NO 341
<211> LENGTH: 10
<212> TYPE: PRT
<213> ORGANISM: Homo sapiens

<400> SEQUENCE: 341

Gln Gln Arg Asn Asn Trp Pro Pro Leu Thr
1               5                   10

<210> SEQ ID NO 342
<211> LENGTH: 24
<212> TYPE: DNA
<213> ORGANISM: Homo sapiens

<400> SEQUENCE: 342
ggattcaggt tcaatgaatt taat                                          24

<210> SEQ ID NO 343
<211> LENGTH: 24
<212> TYPE: DNA
<213> ORGANISM: Homo sapiens

<400> SEQUENCE: 343
atctcaattg atgggagaca caaa                                          24
```

<210> SEQ ID NO 344
<211> LENGTH: 48
<212> TYPE: DNA
<213> ORGANISM: Homo sapiens

<400> SEQUENCE: 344
gtgacagatg ggaaagcagt ggatgggttt tccggaattt tagagttc             48

<210> SEQ ID NO 345
<211> LENGTH: 18
<212> TYPE: DNA
<213> ORGANISM: Homo sapiens

<400> SEQUENCE: 345
cagagtgttg gcggctac                                              18

<210> SEQ ID NO 346
<211> LENGTH: 9
<212> TYPE: DNA
<213> ORGANISM: Homo sapiens

<400> SEQUENCE: 346 gatgcatcc                                                         9

<210> SEQ ID NO 347
<211> LENGTH: 30
<212> TYPE: DNA
<213> ORGANISM: Homo sapiens

<400> SEQUENCE: 347
cagcagcgta acaactggcc accactcact                                 30

<210> SEQ ID NO 348
<211> LENGTH: 123
<212> TYPE: PRT
<213> ORGANISM: Homo sapiens

<400> SEQUENCE: 348

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Arg Phe Asn Glu Phe
            20                  25                  30

Asn Met His Trp Val Arg Gln Ala Pro Gly Lys Gly Leu Glu Trp Val
        35                  40                  45

Ala Val Ile Ser Ile Asp Gly Arg His Lys Tyr Asn Ala Asp Ser Val
    50                  55                  60

Glu Gly Arg Phe Thr Ile Ser Arg Asp Asn Ser Arg Asn Thr Leu Tyr
65                  70                  75                  80

Leu Gln Met Asn Ser Leu Arg Val Glu Asp Thr Ala Leu Tyr Tyr Cys
                85                  90                  95

Val Thr Asp Gly Lys Ala Val Asp Gly Phe Ser Gly Ile Leu Glu Phe
            100                 105                 110

Trp Gly Gln Gly Thr Pro Val Thr Val Ser Thr
        115                 120

<210> SEQ ID NO 349
<211> LENGTH: 108
<212> TYPE: PRT
<213> ORGANISM: Homo sapiens

<400> SEQUENCE: 349

Glu Ile Val Leu Thr Gln Ser Pro Ala Thr Leu Ser Leu Ser Pro Gly
1               5                   10                  15

Glu Arg Ala Thr Leu Ser Cys Trp Ala Ser Gln Ser Val Gly Gly Tyr
            20                  25                  30

Leu Ala Trp Tyr Gln Lys Pro Gly Gln Ala Pro Arg Leu Leu Ile
        35                  40                  45

Tyr Asp Ala Ser Ile Arg Ala Thr Gly Ile Pro Ala Arg Phe Ser Gly
    50                  55                  60

Ser Gly Ser Gly Thr His Phe Thr Leu Thr Ile Asn Ser Leu Glu Pro
65                  70                  75                  80

Glu Asp Phe Ala Val Tyr Tyr Cys Gln Gln Arg Asn Asn Trp Pro Pro
                85                  90                  95

Leu Thr Phe Gly Gly Gly Thr Lys Val Glu Ile Lys
            100                 105

<210> SEQ ID NO 350
<211> LENGTH: 370
<212> TYPE: DNA
<213> ORGANISM: Homo sapiens

<400> SEQUENCE: 350

```
caggtgcaac tggtggagtc tgggggaggc gtggtccagc ctggggaggtc cctgagactc    60
tcctgtgcag cctctggatt caggttcaat gaatttaata tgcactgggt ccgccaggct   120
ccaggcaagg gcctggagtg ggtggcagtt atctcaattg atgggagaca caaatacaac   180
gcagactccg tgagggccg attcaccatc tccagagaca attccagaaa cactctttat   240
ctgcaaatga acagcctgag agttgaggac acggctcttt attactgtgt gacagatggg   300
aaagcagtgg atgggttttc cggaatttta gagttctggg gccagggaac cccagtcacc   360
gtctccacag                                                          370
```

<210> SEQ ID NO 351
<211> LENGTH: 325
<212> TYPE: DNA
<213> ORGANISM: Homo sapiens

<400> SEQUENCE: 351

```
gaaattgtgt tgacacagtc tccggccacc ctgtctttgt ctccagggga gagagccacc    60
ctctcctgct gggccagtca gagtgttggc ggctacttag cctggtacca acaaaaacct   120
ggccaggctc ccaggctcct catctatgat gcatccatca gggccactgg catcccagcc   180
aggttcagtg gcagtgggtc tgggacacac ttcactctca ccatcaatag cctcgagcct   240
gaagattttg ccgtttatta ctgtcagcag cgtaacaact ggccaccact cactttcggc   300
ggagggacca aggtggagat caaac                                         325
```

<210> SEQ ID NO 352
<211> LENGTH: 8
<212> TYPE: PRT
<213> ORGANISM: Homo sapiens

<400> SEQUENCE: 352

Gly Phe Ser Phe Ser Asn Phe Glu
1               5

<210> SEQ ID NO 353
<211> LENGTH: 24

```
<212> TYPE: DNA
<213> ORGANISM: Homo sapiens

<400> SEQUENCE: 353
ggattcagtt tcagtaactt tgag                                           24

<210> SEQ ID NO 354
<211> LENGTH: 24
<212> TYPE: DNA
<213> ORGANISM: Homo sapiens

<400> SEQUENCE: 354
attgatttta ctggctctac catc                                           24

<210> SEQ ID NO 355
<211> LENGTH: 48
<212> TYPE: DNA
<213> ORGANISM: Homo sapiens

<400> SEQUENCE: 355
gtgagagatg cgggccgttg gggcaccagt tggtactatt ttgactat                 48

<210> SEQ ID NO 356
<211> LENGTH: 33
<212> TYPE: DNA
<213> ORGANISM: Homo sapiens

<400> SEQUENCE: 356
cagtcatatg acagcagcct gaatggttgg gtg                                 33

<210> SEQ ID NO 357
<211> LENGTH: 123
<212> TYPE: PRT
<213> ORGANISM: Homo sapiens

<400> SEQUENCE: 357

Ala Val Gln Leu Val Glu Ser Gly Gly Gly Leu Ala Gln Pro Gly Arg
1               5                   10                  15

Ser Leu Arg Leu Ser Cys Lys Val Ser Gly Phe Ser Phe Ser Asn Phe
            20                  25                  30

Glu Met Asn Trp Val Arg Gln Ala Pro Gly Lys Gly Leu Glu Trp Ile
        35                  40                  45

Ala Tyr Ile Asp Phe Thr Gly Ser Thr Ile Tyr Tyr Ser Asp Ser Val
    50                  55                  60

Lys Gly Arg Phe Thr Ile Ser Arg Asp Thr Ala Arg Asn Ser Leu Tyr
65                  70                  75                  80

Leu Gln Met Asn Lys Leu Arg Val Glu Asp Thr Ala Val Tyr Tyr Cys
                85                  90                  95

Val Arg Asp Ala Gly Arg Trp Gly Thr Ser Trp Tyr Tyr Phe Asp Tyr
            100                 105                 110

Trp Gly Gln Gly Thr Leu Val Thr Val Ser Ser
        115                 120

<210> SEQ ID NO 358
<211> LENGTH: 370
<212> TYPE: DNA
<213> ORGANISM: Homo sapiens

<400> SEQUENCE: 358
gcggtgcagc tggtggaatc cggggggcggc ttggcacagc ctggacggtc cctgaggctc    60
```

```
tcgtgtaaag tgtccggatt cagtttcagt aactttgaga tgaactgggt ccgccaggct    120
ccagggaagg ggctggagtg gattgcatat attgatttta ctggctctac catctactac    180
tcagactctg tgaagggacg gtttaccatt tccagagaca ccgccaggaa ctcactctat    240
ctgcagatga acaaattgag agtcgaggac acggctgttt attactgtgt gagagatgcg    300
ggccgttggg gcaccagttg gtactatttt gactattggg gccagggcac cctggtcacc    360
gtctcctcag                                                           370
```

<210> SEQ ID NO 359
<211> LENGTH: 334
<212> TYPE: DNA
<213> ORGANISM: Homo sapiens

<400> SEQUENCE: 359

```
cagtctgtgc tgacgcagcc gccctcagtg tctggggccc cagggcagag ggtcaccatc    60
tcctgcactg ggctcagctc aacatcgggg caggttatg atatacactg gtatcagcag    120
attccaggaa aagcccccaa actcctcatc tatggtaaca caatcggcc tcagggggtc    180 cctgaccgat tctctggctc taagtctggc acctcagtct ccctggccat cactgggctc    240
caggctgagg atgaggctga ttattactgc agtcatatg acagcagcct gaatggttgg    300
gtgttcggcg gagggaccag gttgaccgtc ctaa                                334
```

<210> SEQ ID NO 360
<211> LENGTH: 8
<212> TYPE: PRT
<213> ORGANISM: Homo sapiens

<400> SEQUENCE: 360

Gly Phe Thr Phe Gly Ser Tyr Glu
1               5

<210> SEQ ID NO 361
<211> LENGTH: 11
<212> TYPE: PRT
<213> ORGANISM: Homo sapiens

<400> SEQUENCE: 361

Gln Ser Tyr Asp Asn Ser Leu Asn Gly Trp Val
1               5                   10

<210> SEQ ID NO 362
<211> LENGTH: 24
<212> TYPE: DNA
<213> ORGANISM: Homo sapiens

<400> SEQUENCE: 362

```
ggattcacct tcggaagcta tgaa                                            24
```

<210> SEQ ID NO 363
<211> LENGTH: 24
<212> TYPE: DNA
<213> ORGANISM: Homo sapiens

<400> SEQUENCE: 363

```
attgacttta ctggttcaac catc                                            24
```

<210> SEQ ID NO 364
<211> LENGTH: 48
<212> TYPE: DNA
<213> ORGANISM: Homo sapiens

<400> SEQUENCE: 364
gtgagagatg cgggccgctg gggcaccagt tggtattact ttgactat                48

<210> SEQ ID NO 365
<211> LENGTH: 9
<212> TYPE: DNA
<213> ORGANISM: Homo sapiens

<400> SEQUENCE: 365 ggcaacaac                9

<210> SEQ ID NO 366
<211> LENGTH: 33
<212> TYPE: DNA
<213> ORGANISM: Homo sapiens

<400> SEQUENCE: 366
cagtcctatg acaacagcct gaatggttgg gtg                33

<210> SEQ ID NO 367
<211> LENGTH: 123
<212> TYPE: PRT
<213> ORGANISM: Homo sapiens

<400> SEQUENCE: 367

Ala Val Arg Leu Val Glu Ser Gly Gly Gly Leu Ala Gln Pro Gly Arg
1               5                   10                  15

Ser Leu Arg Leu Ser Cys Gln Val Ser Gly Phe Thr Phe Gly Ser Tyr
            20                  25                  30

Glu Met Asn Trp Val Arg Gln Ala Pro Gly Lys Gly Leu Glu Trp Ile
        35                  40                  45

Ala Tyr Ile Asp Phe Thr Gly Ser Thr Ile Tyr Tyr Ala Asp Ser Val
    50                  55                  60

Lys Gly Arg Phe Thr Ile Ser Arg Asn Thr Ala Arg Asn Ser Leu Tyr
65                  70                  75                  80

Leu Gln Met Asn Ser Leu Arg Val Glu Asp Thr Ala Val Tyr Tyr Cys
                85                  90                  95

Val Arg Asp Ala Gly Arg Trp Gly Thr Ser Trp Tyr Tyr Phe Asp Tyr
            100                 105                 110

Trp Gly Gln Gly Thr Arg Val Thr Val Ser Pro
        115                 120

<210> SEQ ID NO 368
<211> LENGTH: 111
<212> TYPE: PRT
<213> ORGANISM: Homo sapiens

<400> SEQUENCE: 368

Gln Ser Val Leu Thr Gln Pro Pro Ser Val Ser Gly Ala Pro Gly Gln
1               5                   10                  15

Arg Val Thr Ile Ser Cys Thr Gly Ile Ser Ser Asn Ile Gly Ala Gly
            20                  25                  30

Tyr Asp Ile His Trp Tyr Gln Gln Ile Pro Gly Lys Ala Pro Lys Leu
        35                  40                  45

Leu Val Tyr Gly Asn Asn Asn Arg Pro Ser Gly Val Pro Asp Arg Phe
    50                  55                  60

Ser Gly Ser Lys Ser Gly Thr Ser Val Ser Leu Ala Ile Thr Gly Leu
65                  70                  75                  80

```
Gln Val Glu Asp Glu Ala Asp Tyr Tyr Cys Gln Ser Tyr Asp Asn Ser
             85                  90                  95

Leu Asn Gly Trp Val Phe Gly Gly Gly Thr Arg Leu Thr Val Leu
            100                 105                 110

<210> SEQ ID NO 369
<211> LENGTH: 370
<212> TYPE: DNA
<213> ORGANISM: Homo sapiens

<400> SEQUENCE: 369
gcggtgcggc tggtggagtc tgggggaggc ttggcacagc ctggacggtc cctgagactc     60
tcgtgtcaag tgtctggatt caccttcgga agctatgaaa tgaactgggt ccgccaggct    120
cccggcaagg gactggagtg gattgcctac attgacttta ctggttcaac catctactac    180
gcagactctg tgaagggccg attcaccata tccagaaaca ccgccaggaa ctcactctat    240
ctgcagatga acagcctgag agtcgaggac acggctgttt attactgtgt gagagatgcg    300
ggccgctggg gcaccagttg gtattacttt gactattggg gccaaggaac ccgggtcacc    360
gtctccccag                                                           370

<210> SEQ ID NO 370
<211> LENGTH: 334
<212> TYPE: DNA
<213> ORGANISM: Homo sapiens

<400> SEQUENCE: 370
cagtctgtgc tgacgcagcc gccctcagtg tctggggccc cagggcagag ggtcaccatc     60
tcctgcactg ggatcagctc caacatcggg gcaggttatg atatacactg gtatcagcag    120
attccaggaa aagcccccaa actcctcgtc tatggcaaca caatcggcc ctcaggagtc     180 cctgaccgat tctctggctc taagtctggc acctcagtct ccctggccat cactgggctc    240
caggttgagg atgaggctga ttattactgc cagtcctatg acaacagcct gaatggttgg    300
gtgttcggcg gagggaccag gttgaccgtc ctaa                                334

<210> SEQ ID NO 371
<211> LENGTH: 516
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 371
atgaacagca aagacctgac gccgttcttg acgaccttgt ggctgctatt ggaccacagc     60
cgcgtgccgc gggtacgcgc agaagaatgt tgcgaattca taaacgtcaa ccacccgccg    120
gaacgctgtt acgatttcaa aatgtgcaat ctgttcaccg tcgcgctgcg cgtgtccggac    180 ggcgaagtct gctacagtcc cgagaaaacg gctgagattc gcgggatcgt caccaccatg    240
acccattcat tgacacgcca ggtcatccac aacaaactga cgagctgcaa ctacaatccg    300
ttatacctcg aagctgacgg gcgaatacgc tgcggcaaag tgagcgacaa ggcgcagtac    360
ctgctgggcg ccgctggcag cgttccctat cgatggatca acctggaata cgacaagata    420
acccggatcg tgggcctgga tcagtacctg agagcgttaa agaaacacaa acggctggat    480
gtgtgccgcg ctaaaatggg ctatatgctg cagtag                              516
```